(12) United States Patent
Drmanac et al.

(10) Patent No.: US 9,524,369 B2
(45) Date of Patent: Dec. 20, 2016

(54) PROCESSING AND ANALYSIS OF COMPLEX NUCLEIC ACID SEQUENCE DATA

(75) Inventors: Radoje Drmanac, Los Altos Hills, CA (US); Brock A. Peters, San Francisco, CA (US); Bahram Ghaffarzadeh Kermani, Los Altos, CA (US)

(73) Assignee: Complete Genomics, Inc., Mountain View, CA (US)

( * ) Notice: Subject to any disclaimer, the term of this patent is extended or adjusted under 35 U.S.C. 154(b) by 890 days.

(21) Appl. No.: 13/447,087

(22) Filed: Apr. 13, 2012

(65) Prior Publication Data
US 2013/0124100 A1 May 16, 2013
US 2015/0379192 A9 Dec. 31, 2015

Related U.S. Application Data

(63) Continuation-in-part of application No. 12/816,365, filed on Jun. 15, 2010, now Pat. No. 8,592,150.

(60) Provisional application No. 61/187,162, filed on Jun. 15, 2009, provisional application No. 61/546,516, filed on Oct. 12, 2011, provisional application No. 61/527,428, filed on Aug. 25, 2011, provisional application No. 61/517,196, filed on Apr. 14, 2011.

(51) Int. Cl.
G01N 33/50 (2006.01)
G06F 19/22 (2011.01)
C12Q 1/68 (2006.01)

(52) U.S. Cl.
CPC ............ *G06F 19/22* (2013.01); *C12Q 1/6869* (2013.01)

(58) Field of Classification Search
None
See application file for complete search history.

(56) References Cited

U.S. PATENT DOCUMENTS

| | | |
|---|---|---|
| 4,719,179 A | 1/1988 | Barany |
| 4,883,750 A | 11/1989 | Whiteley et al. |
| 5,091,302 A | 2/1992 | Newman et al. |
| 5,124,246 A | 6/1992 | Urdea et al. |
| 5,143,854 A | 9/1992 | Pirrung et al. |
| 5,202,231 A | 4/1993 | Drmanac et al. |
| 5,354,668 A | 10/1994 | Auerbach |
| 5,403,708 A | 4/1995 | Brennan et al. |
| 5,426,180 A | 6/1995 | Kool |
| 5,427,930 A | 6/1995 | Birkenmeyer et al. |
| 5,474,796 A | 12/1995 | Brennan |
| 5,492,806 A | 2/1996 | Drmanac et al. |
| 5,508,169 A | 4/1996 | Deugau et al. |
| 5,525,464 A | 6/1996 | Drmanac et al. |
| 5,632,957 A | 5/1997 | Heller et al. |
| 5,641,658 A | 6/1997 | Adams et al. |
| 5,648,245 A | 7/1997 | Fire et al. |
| 5,710,000 A | 1/1998 | Sapolsky et al. |
| 5,714,320 A | 2/1998 | Kool |
| 5,728,524 A | 3/1998 | Sibson |
| 5,744,305 A | 4/1998 | Fodor et al. |
| 5,800,992 A | 9/1998 | Fodor et al. |
| 5,854,033 A | 12/1998 | Lizardi |
| 5,866,337 A | 2/1999 | Schon |
| 5,871,921 A | 2/1999 | Landegren et al. |
| 5,888,737 A | 3/1999 | DuBridge et al. |
| 5,994,068 A | 11/1999 | Guilfoyle et al. |
| 6,004,755 A | 12/1999 | Wang |
| 6,013,445 A | 1/2000 | Albrecht et al. |
| 6,045,994 A | 4/2000 | Zabeau et al. |
| 6,077,668 A | 6/2000 | Kool |
| 6,096,880 A | 8/2000 | Kool |
| 6,124,120 A | 9/2000 | Lizardi |
| 6,136,537 A | 10/2000 | Macevicz |
| 6,143,495 A | 11/2000 | Lizardi et al. |
| 6,143,527 A | 11/2000 | Pachuk et al. |
| 6,210,891 B1 | 4/2001 | Nyren et al. |
| 6,210,894 B1 | 4/2001 | Brennan |
| 6,218,152 B1 | 4/2001 | Auerbach |
| 6,221,603 B1 | 4/2001 | Mahtani |
| 6,255,469 B1 | 7/2001 | Seeman et al. |
| 6,258,539 B1 | 7/2001 | Hunkapiller et al. |
| 6,261,808 B1 | 7/2001 | Auerbach |
| 6,270,320 B1 | 8/2001 | Heyder et al. |
| 6,270,961 B1 | 8/2001 | Drmanac |
| 6,274,320 B1 | 8/2001 | Rothberg et al. |
| 6,274,351 B1 | 8/2001 | Peponnet |
| 6,284,497 B1 | 9/2001 | Sabanayagam et al. |
| 6,287,824 B1 | 9/2001 | Lizardi |
| 6,291,183 B1 | 9/2001 | Pirrung et al. |

(Continued)

FOREIGN PATENT DOCUMENTS

| | | |
|---|---|---|
| JP | 4-262799 A | 9/1992 |
| JP | 4-304900 A | 10/1992 |

(Continued)

OTHER PUBLICATIONS

Zerbino et al. ("Velvet: algorithms for de novo short read assembly using de Bruijn graphs," Genome Research; May 2008 published online Mar. 18, 2008, vol. 18, No. 5; pp. 821-829).*
Advisory Action in U.S. Appl. No. 13/017,244 mailed Oct. 17, 2013.
Notice of Allowance in U.S. Appl. No. 13/954,778 mailed Oct. 21, 2013.
Non-Final Office Action in U.S. Appl. No. 13/962,893 mailed Oct. 22, 2013.
Non-Final Office Action in U.S. Appl. No. 13/975,215 mailed Oct. 23, 2013.
Interview Summary in U.S. Appl. No. 13/017,244 mailed Oct. 25, 2013.
Non-Final Office Action in U.S. Appl. No. 13/975,215 mailed Nov. 12, 2013.

(Continued)

*Primary Examiner* — Jason Sims
(74) *Attorney, Agent, or Firm* — Kilpatrick Townsend & Stockton LLP

(57) ABSTRACT

The present invention is directed to logic for analysis of nucleic acid sequence data that employs algorithms that lead to a substantial improvement in sequence accuracy and that can be used to phase sequence variations, e.g., in connection with the use of the long fragment read (LFR) process.

39 Claims, 21 Drawing Sheets

(56) References Cited

U.S. PATENT DOCUMENTS

| | | | |
|---|---|---|---|
| 6,297,006 B1 | 10/2001 | Drmanac et al. |
| 6,297,016 B1 | 10/2001 | Egholm et al. |
| 6,306,597 B1 | 10/2001 | Macevicz |
| 6,309,824 B1 | 10/2001 | Drmanac |
| 6,316,229 B1 | 11/2001 | Lizardi et al. |
| 6,329,150 B1 | 12/2001 | Lizardi et al. |
| 6,344,329 B1 | 2/2002 | Lizardi |
| 6,346,413 B1 | 2/2002 | Fodor et al. |
| 6,355,419 B1 | 3/2002 | Alfenito |
| 6,355,432 B1 | 3/2002 | Fodor et al. |
| 6,401,267 B1 | 6/2002 | Drmanac |
| 6,403,320 B1 | 6/2002 | Read et al. |
| 6,413,722 B1 | 7/2002 | Arnold et al. |
| 6,432,360 B1 | 8/2002 | Church |
| 6,472,156 B1 | 10/2002 | Wittwer et al. |
| 6,491,871 B1 | 12/2002 | Fodor et al. |
| 6,492,806 B2 | 12/2002 | Shirai |
| 6,500,620 B2 | 12/2002 | Yu et al. |
| 6,514,768 B1 | 2/2003 | Guire et al. |
| 6,534,293 B1 | 3/2003 | Barany |
| 6,558,928 B1 | 5/2003 | Landegren |
| 6,573,369 B2 | 6/2003 | Henderson et al. |
| 6,576,448 B2 | 6/2003 | Weissman et al. |
| 6,589,726 B1 | 7/2003 | Butler et al. |
| 6,610,481 B2 | 8/2003 | Koch |
| 6,610,492 B1 | 8/2003 | Stanton, Jr. et al. |
| 6,620,584 B1 | 9/2003 | Chee et al. |
| 6,632,609 B2 | 10/2003 | Lizardi |
| 6,653,077 B1 | 11/2003 | Brenner |
| 6,660,229 B2 | 12/2003 | Cantor et al. |
| 6,783,943 B2 | 8/2004 | Christian et al. |
| 6,787,308 B2 | 9/2004 | Balasubramanian et al. |
| 6,812,005 B2 | 11/2004 | Fan et al. |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,890,741 B2 | 5/2005 | Fan et al. |
| 6,913,884 B2 | 7/2005 | Stuelpngnagel et al. |
| 6,975,943 B2 | 12/2005 | Gibbs et al. |
| 6,977,153 B2 | 12/2005 | Kumar et al. |
| 6,998,228 B2 | 2/2006 | Henderson et al. |
| 7,011,945 B2 | 3/2006 | Qiao |
| 7,064,197 B1 | 6/2006 | Rabbani et al. |
| 7,074,600 B2 | 7/2006 | Dean et al. |
| 7,083,929 B2 | 8/2006 | Wong |
| 7,232,656 B2 | 6/2007 | Balasubramanian et al. |
| 7,244,559 B2 | 7/2007 | Rothberg et al. |
| 7,264,929 B2 | 9/2007 | Rothberg et al. |
| 7,276,720 B2 | 10/2007 | Ulmer |
| 7,297,778 B2 | 11/2007 | Matsuzaki et al. |
| 7,384,737 B2 | 6/2008 | Barnes |
| 7,544,473 B2 | 6/2009 | Brenner |
| 7,565,346 B2 * | 7/2009 | Fan et al. |
| 7,709,197 B2 | 5/2010 | Drmanac |
| 7,807,375 B2 | 10/2010 | Cantor et al. |
| 7,897,344 B2 | 3/2011 | Dahl et al. |
| 7,901,891 B2 | 3/2011 | Drmanac |
| 2002/0004204 A1 | 1/2002 | O'Keefe |
| 2002/0012930 A1 | 1/2002 | Rothberg et al. |
| 2002/0025532 A1 | 2/2002 | Huang et al. |
| 2002/0055100 A1 | 5/2002 | Kawashima et al. |
| 2002/0076716 A1 | 6/2002 | Sabanayagam et al. |
| 2002/0197621 A1 | 12/2002 | Drmanac |
| 2003/0068629 A1 | 4/2003 | Rothberg et al. |
| 2003/0092007 A1 | 5/2003 | Gibbs et al. |
| 2003/0100006 A1 | 5/2003 | Senapathy |
| 2003/0148313 A1 | 8/2003 | Strathmann |
| 2004/0002090 A1 | 1/2004 | Mayer et al. |
| 2004/0029165 A1 | 2/2004 | Wong |
| 2004/0229221 A1 | 11/2004 | Schon |
| 2004/0241730 A1 | 12/2004 | Yakhini et al. |
| 2004/0248144 A1 | 12/2004 | Mir |
| 2004/0248161 A1 | 12/2004 | Rothberg et al. |
| 2004/0259118 A1 | 12/2004 | Macevicz |
| 2005/0019776 A1 | 1/2005 | Callow et al. |
| 2005/0037356 A1 | 2/2005 | Gullberg et al. |
| 2005/0042633 A1 | 2/2005 | Williams |
| 2005/0042649 A1 | 2/2005 | Balasubramanian et al. |
| 2005/0100939 A1 | 5/2005 | Namsaraev et al. |
| 2005/0130173 A1 | 6/2005 | Leamon et al. |
| 2005/0191656 A1 | 9/2005 | Drmanac et al. |
| 2005/0202489 A1 | 9/2005 | Cho et al. |
| 2005/0214840 A1 | 9/2005 | Chen |
| 2005/0244863 A1 | 11/2005 | Mir |
| 2006/0012793 A1 | 1/2006 | Harris |
| 2006/0024681 A1 | 2/2006 | Smith et al. |
| 2006/0024711 A1 | 2/2006 | Lapidus et al. |
| 2006/0073506 A1 | 4/2006 | Christians et al. |
| 2006/0223097 A1 | 10/2006 | Sapolsky et al. |
| 2006/0223122 A1 | 10/2006 | Fogo et al. |
| 2006/0234234 A1 | 10/2006 | Van Dongen et al. |
| 2006/0246453 A1 | 11/2006 | Kato et al. |
| 2007/0015182 A1 | 1/2007 | Abarzua |
| 2007/0037152 A1 | 2/2007 | Drmanac |
| 2007/0037197 A1 | 2/2007 | Young et al. |
| 2007/0042401 A1 | 2/2007 | Morgan et al. |
| 2007/0054311 A1 | 3/2007 | Kamberov et al. |
| 2007/0072208 A1 | 3/2007 | Drmanac |
| 2007/0099208 A1 | 5/2007 | Drmanac et al. |
| 2008/0051294 A1 | 2/2008 | Gormley et al. |
| 2008/0234136 A1 | 9/2008 | Drmanac et al. |
| 2008/0318796 A1 | 12/2008 | Drmanac et al. |
| 2009/0005252 A1 | 1/2009 | Drmanac et al. |
| 2009/0005259 A1 | 1/2009 | Drmanac et al. |
| 2009/0011416 A1 | 1/2009 | Drmanac et al. |
| 2009/0011943 A1 | 1/2009 | Drmanac et al. |
| 2009/0036316 A1 | 2/2009 | Drmanac |
| 2009/0099041 A1 | 4/2009 | Church et al. |
| 2009/0118488 A1 | 5/2009 | Drmanac et al. |
| 2009/0125246 A1 | 5/2009 | Ruiz Laza |
| 2009/0137404 A1 | 5/2009 | Drmanac et al. |
| 2009/0137414 A1 | 5/2009 | Drmanac et al. |
| 2009/0155781 A1 | 6/2009 | Drmanac et al. |
| 2009/0264299 A1 | 10/2009 | Drmanac et al. |
| 2010/0112590 A1 | 5/2010 | Lo et al. |
| 2010/0199155 A1 | 8/2010 | Kermani et al. |
| 2010/0279883 A1 | 11/2010 | Sampas et al. |
| 2011/0033854 A1 * | 2/2011 | Drmanac et al. ............... 435/6 |
| 2011/0105353 A1 | 5/2011 | Lo et al. |
| 2011/0319281 A1 | 12/2011 | Drmanac |
| 2013/0035248 A1 | 2/2013 | Icenhour |
| 2013/0040344 A1 | 2/2013 | Ju |
| 2013/0040843 A1 | 2/2013 | Von Toerne et al. |
| 2013/0040847 A1 | 2/2013 | Thrippleton et al. |
| 2013/0059740 A1 | 3/2013 | Drmanac et al. |

FOREIGN PATENT DOCUMENTS

| | | |
|---|---|---|
| WO | 95/09248 A1 | 4/1995 |
| WO | 01/09384 A2 | 2/2001 |
| WO | 01/62982 A2 | 8/2001 |
| WO | 02/061143 A2 | 8/2002 |
| WO | 02/074988 A2 | 9/2002 |
| WO | 02/103046 A2 | 12/2002 |
| WO | 03/012119 A2 | 2/2003 |
| WO | 03/040391 A2 | 5/2003 |
| WO | 03/102231 A1 | 12/2003 |
| WO | 2004/072294 A2 | 8/2004 |
| WO | 2004/076683 A2 | 9/2004 |
| WO | 2005/040425 A2 | 5/2005 |
| WO | 2005/047523 A2 | 5/2005 |
| WO | 2005/078130 A1 | 8/2005 |
| WO | 2005/080605 A2 | 9/2005 |
| WO | 2005/082098 A2 | 9/2005 |
| WO | 2005/093094 A2 | 10/2005 |
| WO | 2005/116262 A1 | 12/2005 |
| WO | 2006/007207 A2 | 1/2006 |
| WO | 2006/040549 A2 | 4/2006 |
| WO | 2006/055521 A2 | 5/2006 |
| WO | 2006/073504 A2 | 7/2006 |
| WO | 2006/084132 A2 | 8/2006 |
| WO | 2006/138257 A2 | 12/2006 |
| WO | 2007/014397 A2 | 2/2007 |
| WO | 2007/025124 A1 | 3/2007 |

(56) References Cited

FOREIGN PATENT DOCUMENTS

| WO | 2007/044245 A2 | 4/2007 |
|---|---|---|
| WO | 2007/061425 A1 | 5/2007 |
| WO | 2007/062160 A2 | 5/2007 |
| WO | 2007/106509 A2 | 9/2007 |
| WO | 2007/120208 A2 | 10/2007 |
| WO | 2007/121489 A2 | 10/2007 |
| WO | 2007/133710 A2 | 11/2007 |
| WO | 2011/038155 A2 | 3/2011 |

OTHER PUBLICATIONS

Non-Final Office Action in U.S. Appl. No. 13/975,223 mailed Nov. 12, 2013.
Non-Final Office Action in U.S. Appl. No. 13/975,234 mailed Nov. 13, 2013.
"Phasing Analysis Service for Whole Human Genome Sequencing," Illumina Genome Network, Data Sheet: Genome Network Services, downloaded on Jul. 19, 2013 from http://www.illumina.com, 4 pages.
Bader et al., "The Relative Power of SNPs and Haplotype as Genetic Markers for Association Tests," Pharmacogenomics, 2(1):11-24 (2001).
Bansal et al., "HapCUT: An Efficient and Accurate Algorithm for the Haplotype Assembly Problem," Bioinformatics, 23:i153-i159 (2008), downloaded on Mar. 14, 2013 from http://bioinformatics.oxfordjournals.org.
Batzoglou et al., "ARACHNE: A Whole-Genome Shotgun Assembler," Genome Research, 12:177-189 (2002).
Baumann, "Determination of Haplotypes from Genotype Information," Informatik, ETH Zurich, 2005, 15 pages.
Blanco et al., "Highly Efficient DNA Synthesis by the Phage Phi 29 DNA Polymerase," Journal of Biological Chemistry, 264(15):8935-8940 (1989).
Brenner et al., "Gene Expression Analysis by Massively Parallel Signature Sequencing (MPSS) on Microbead Arrays," Nature Biotechnology, 18:630-634 (2000).
Burgtorf et al., "Clone-Based Systematic Haplotyping (CSH): A Procedure for Physical Haplotyping of Whole Genomes," Genome Research, 13(12):2717-2724 (2003).
Callow et al., "Selective DNA Amplification from Complex Genomes using Universal Double-Sided Adapters," Nucleic Acids Research, 32(2):e21, pp. 1-6 (2004).
Chen et al., "A Homogenous, Ligase-Mediated DNA Diagnostic Test," Genome Research, 8(5):549-556 (1998).
Cheung et al., "Whole Genome Amplification using a Degenerate Oligonucleotide Primer Allows Hundreds of Genotypes to be Performed on Less Than One Nanogram of Genomic DNA," Proc. Natl. Acad. Sci., 93:14676-14679 (1996).
Christensen et al., "Search for Compound Heterozygous Effects in Exome Sequence of Unrelated Subjects," Genetic Analysis Workshop, BMC Proceedings, 5(Suppl. 9), 5 pages.
Cilibrasi et al., "On the Complexity of Several Haplotyping Problems," WABI, vol. 3692 of Lecture Notes in Computer Science, Springer, Berlin, 2005, pp. 128-139.
Collins et al., "Directional Cloning of DNA Fragments at a Large Distance from an Initial Probe: A Circularization Method," Proc. Natl. Acad. Sci., 81:6812-6816 (1984).
Cowie et al., "Identification of APC Gene Mutations in Colorectal Cancer using Universal Microarray-Based Combinatorial Sequencing-by-Hybridization," Human Mutation, 24:261-271 (2004).
Cui et al, "Determination of Gene Organization in Individual Haplotypes by Analyzing Single DNA Fragments from a Single Spermatozoa," Proc. Natl. Acad. Sci., 95:10791-10796 (1998).
Dahl et al., "Multiplex Amplification Enabled by Selective Circularization of Large Sets of Genomic DNA Fragments," Nucleic Acids Research, 33(8):e71 (2005).
Dear et al., "A High-Resolution Metric HAPPY Map of Human Chromosome 14," Genomics, 48:232-241 (1998).
Dear et al., "Happy Mapping: Linkage Mapping using a Physical Analogue of Meiosis," Nucleic Acids Research, 21:13-20 (1993).

Delius et al., "Separation of Complementary Strands of Plasmid DNA using the Biotin-Avidin System and its Application to Heteroduplex Formation and RNA/DNA Hybridizations in Electron Microscopy," Nucleic Acids Research, 13:5457-5469 (1985).
Drmanac et al., "Sequencing by Hybridization (SBH): Advantages, Achievements, and Opportunities," Advances in Biochemical Engineering/Biotechnology, 77:76-101 (2002).
Duitama et al., "Fosmid-Based Whole Genome Haplotyping of a HapMap Trio Child: Evaluation of Single Individual Haplotyping Techniques," Nucleic Acids Research Advance Access, downloaded on Mar. 11, 2012 from http://nar.oxfordjournals.org, 13 pages.
Eskin et al., "Large Scale Reconstruction of Haplotypes from Genotype Data," RECOMB'03, Berlin, Germany, 2003, 10 pages.
Fan et al., "Whole-Genome Molecular Haplotyping of Single Cells," Nature Biotechnology Advance Online Publication, downloaded on Dec. 19, 2010 from http://www.nature.com/naturebiotechnoogy/, 9 pages.
Halldorsson et al., "Haplotype Phasing by Multi-Assembly of Shared Haplotypes: Phase-Dependent Interactions Between Rare Variants," WSPC Proceedings, 2010, pp. 88-99.
Havlak et al., "The Atlas Genome Assembly System," Genome Research, 14:721-732 (2004).
Henke et al., "Betaine Improves the PCR Amplification of GC-Rich DNA Sequences," Nucleic Acids Research, 25(19): 3957-3958 (1997).
Hormozdiari et al., "Combinatorial Algorithms for Structural Variation Detection in High-Throughput Sequenced Genomes," Genome Research, 19:1270-1279 (2009).
Hubbell, "Multiplex Sequencing by Hybridization," Journal of Computational Biology, 8(2):141-149 (2001).
Jiang et al., "Old Can Be New Again: HAPPY Whole Genome Sequencing, Mapping and Assembly," International Journal of Biological Science, 5:298-303 (2009).
Kandpal et al., "Selective Enrichment of a Large Size Genomic DNA Fragment by Affinity Capture: An Approach for Genome Mapping," Nucleic Acids Research, 18:1789-1795 (1990).
Kelly et al., "Miniaturizing Chemistry and Biology in Microdroplets," Chemical Communications, 18:1773-1788 (2007).
Kitzman et al., "Haplotype-Resolved Genome Sequencing of a Gujarati Indian Individual," Nature Biotechnology, 29(1):59-64 (2011).
Kiztman et al., "Supplementary Information for: Haplotype-Resolved Genome Sequencing of a Gujarati Indian Individual," Nature Biotechnology, doi: 10.1038/nbt.1740, 2011, 20 pages.
Ladner et al., "Multiplex Detection of Hotspot Mutations by Rolling Circle-Enabled Universal Microarrays," Laboratory Investigation, 81(8):1079-1086 (2001).
Lancia et al., "SNPs Problems, Complexity and Algorithms," Proceedings of the Ninth Annual European Symposium on Algorithms (ESA), Springer, Berlin, 2001, 12 pages.
Lander et al., "Genomic Mapping by Fingerprinting Random Clones: A Mathematical Analysis," Genomics, 2:231-239 (1988).
Li et al., "BEAMing Up for Detection and Quantification of Rare Sequence Variants," Nature Methods, 3:95-97 (2006).
Li et al., "Estimating the Repeat Structure and Length of DNA Sequences using I-Tuples," Genome Research, 13:1916-1922 (2003).
Li et al., "Haplotype Reconstruction from SNP Alignment," Journal of Computational Biology, 11(2-3):507-518 (2004).
Ma et al., "Direct Determination of Molecular Haplotypes by Chromosome Microdissection," NIH Public Access Author Manuscript, Nature Methods 7(4):299-301 (2010).
McKernan et al., "Sequence and Structural Variation in a Human Genome Uncovered by Short-Read, Massively Parallel Ligation Sequencing using Two-Base Encoding," Genome Research, downloaded on Aug. 24, 2011 from http://genome.cship.org, 16 pages.
Metzker, "Emerging Technologies in DNA Sequencing," Genome Research, 15:1767-1776 (2005).
Miller et al., "Assembly Algorithms for Next-Generation Sequencing Data," Genomics, 95(6):315-327 (2010).
Mitra et al., "Digital Genotyping and Haplotyping with Polymerase Colonies," Proc. Natl. Acad. Sci., 100:5926-5931 (2003).

(56) References Cited

OTHER PUBLICATIONS

Niu et al., "Bayesian Haplotype Inference for Multiple Linked Single-Nucleotide Polymorphisms," American Journal of Human Genetics, 70:157-169 (2002).

Paul et al., "Single-Molecule Dilution and Multiple Displacement Amplification for Molecular Haplotyping," Biotechniques, 38(4):553-559 (2005).

Pemberton et al., "Inference of Unexpected Genetic Relatedness among Individuals in HapMap Phase III," The American Journal of Human Genetics, 87:457-464 (2010).

Pevzner et al., "An Eulerian Path Approach to DNA Fragment Assembly," Proc. Natl. Acad. Sci., 98:9748-9753 (2001).

Prodromou et al., "DNA Fragmentation-Based Combinatorial Approach to Soluble Protein Expression, Part 1: Generating DNA Fragment Libraries," Drug Discovery Today, 12(12-22):931-938 (2007).

Ramsay et al., "Intimate Association of Microsatellite Repeats with Retrotransposons and Other Dispersed Repetitive Elements in Barley," The Plant Journal, 17(4):415-425 (1999).

Reich et al., "Combinatorial Domain Hunting: An Effective Approach for the Identification of Soluble Protein Domains Adaptable to High-Throughput Applications," Protein Science, 15(10) 2357 (2006).

Roach et al., "Analysis of Genetic Inheritance in a Family Quartet by Whole-Genome Sequencing," Sciencexpress, downloaded on Mar. 11, 2010 from http://www.sciencexpress.org, 8 pages.

Shendure et al., "Accurate Multiplex Polony Sequencing of an Evolved Bacterial Genome," Science, 309:1728-1732 (2005).

Shendure et al., "Advanced Sequencing Technologies: Methods and Goals," Nature Reviews Genetics, 5:335-344 (2004).

Smirnov et al., "Method of Manufacturing Whole-Genome Microarrays by Rolling Circle Amplification," Genes, Chromosomes & Cancer, 40:71-77 (2004).

Suk et al., "A Comprehensively Molecular Haplotype-Resolved Genome of a European Individual," Genome Research, downloaded on Aug. 24, 2011 from http://genome.cshlp.org, 45 pages.

Tringe et al., "Metagenomics: DNA Sequencing of Environmental Samples," Nature Reviews Genetics, 6:805-814 (2005).

Venter et al., "The Sequence of the Human Genome," Science, 291 (5507): 1304-1351 (2001).

Vingron et al., "Sequence Alignment and Penalty Choice Review of Concepts, Case Studies and Implications," Journal of Molecular Biology, 235(1):1-12 (1994).

Vogelstein et al., "Digital PCR," Proc. Natl. Acad. Sci., 96:9236-9241 (1999).

Voss et al., "Efficient Low Redundancy Large-Scale DNA Sequencing at EMBL," Journal of Biotechnology, 41(2-3):121-129 (1995).

Waterson et al., "On the Sequencing of the Human Genome," Proc. Natl. Acad. Sci., 99:3712-3716 (2002).

Williams et al., "Amplification of Complex Gene Libraries by Emulsion PCR," Nature Methods, 3(7):545-550 (2006).

Wolf et al., "A Genotyping Strategy Based on Incorporation and Cleavage of Chemically Modified Nucleotides," Proc. Natl. Acad. Sci., 99(17):11073-11078 (2002).

International Search Report and Written Opinion for International Application No. PCT/US2012/059806 mailed on Dec. 7, 2012, 10 pages.

International Search Report and Written Opinion for International Application No. PCT/US2012/051825 mailed on Jan. 28, 2013, 23 pages.

Documents on file in U.S. Appl. No. 11/451,692 (now issued as U.S. Pat. No. 7,910,354): Non-Final Office Action (Jun. 5, 2008); Response (Dec. 5, 2008); Ex Parte Quayle Action Apr. 17, 2009); Response (Jun. 17, 2009).

Documents on file in U.S. Appl. No. 12/335,168 (now issued as U.S. Pat. No. 7,901,891): Non-Final Office Action (Nov. 19, 2009); Supplemental Non-Final Office Action (Dec. 1, 2009); Response (Mar. 31, 2010); Final Office Action (Aug. 11, 2010); Response (Oct. 11, 2010).

Documents on file in U.S. Appl. No. 13/017,244: Non-Final Office Action (Aug. 1, 2012); Response (Feb. 1, 2013); Supplemental Response (Feb. 4, 2013); Interview Summary (Feb. 25, 2013); Supplemental Response (Apr. 4, 2013); Interview Summary (Jul. 22, 2013); Final Office Action (Oct. 2, 2013).

Documents on file in Canadian Application No. 2,611,743: Office Action (Oct. 16, 2012); Response (Apr. 16, 2013).

Documents on file in European Application No. 06760745.7: European Search Report and Search Opinion (Sep. 17, 2009); Office Action (Jan. 11, 2010); Response (Jan. 13, 2010); Office Action (Sep. 2, 2010); Response (Mar. 14, 2011); Office Action (Jul. 18, 2012); Response (May 15, 2013); Office Action (Jul. 15, 2013).

Documents on file in European Application No. 12150825.3: European Search Report and Search Opinion (Jul. 17, 2012); Office Action (Jun. 27, 2013).

Documents on file in International Application No. PCT/US2006/022950: International Search Report (Dec. 13, 2007); International Preliminary Report on Patentability (Dec. 17, 2007).

Documents on file in U.S. Appl. No. 12/816,365: Non-Final Office Action (Mar. 29, 2012); Response (Oct. 1, 2012); Final Office Action (Jan. 4, 2013); Interview Summary (Jun. 3, 2013); Notice of Appeal (Jun. 4, 2013); Response (Jul. 10, 2013).

Documents on file in Chinese Application No. 201080036235.6: Office Action (Nov. 5, 2012); Response (May 20, 2013); Office Action (Sep. 16, 2013).

Documents on file in European Application No. 10725582.0: Office Action (Dec. 10, 2012); Response (Jun. 20, 2013); Office Action (Jul. 3, 2013); Response (Sep. 16, 2013).

Documents on file in International Application No. PCT/US2010/038741: International Search Report (Jul. 21, 2011); International Preliminary Report on Patentability (Dec. 16, 2011).

Documents on file in U.S. Appl. No. 13/448,279: Non-Final Office Action (Mar. 28, 2013); Interview Summary (Aug. 21, 2013); Interview Summary (Aug. 23, 2013); Response (Aug. 27, 2013); Interview Summary (Aug. 28, 2013); Supplemental Response (Sep. 23, 2013).

Drmanac, et al., "Human Genome Sequencing Using Unchained Base Reads on Self-Assembling DNA Nanoarrays," Science, Jan. 2010, vol. 327, No. 78, pp. 78-81.

International Search Report and Written Opinion mailed Oct. 16, 2012, PCT Application No. PCT/US2012/033832, 15 pages.

Zerbino et al., "Velvet: Algorithms for de novo short read assembly using de Bruijn graphs." Genome Res.; May 2008, published online Mar. 18, 2008; vol. 18, No. 5; pp. 821-829; p. 821, col. 1, para 2; p. 824, col. 1, para 1; p. 825, col. 1, para 4; p. 825, col. 2, para 1.

International Search Report and Written Opinion for PCT/US2012/33686, mailed Nov. 5, 2012.

Final Office Action mailed Nov. 27, 2013 in U.S. Appl. No. 13/448,279, 28 pages.

"Viruses" (Wikipedia.com, accessed Nov. 24, 2012).

"How many species of bacteria are there," (Wisegeek.com, accessed Jan. 21, 2014).

"Fungi" (Wikipedia.com, accessed Jun. 3, 2013).

"Plant" (Wikipedia.com, accessed Mar. 8, 2013).

"Mammal" (Wikipedia.com, accessed Sep. 22, 2011).

"Murinae" (Wikipedia.com, accessed Mar. 18, 2013).

"Fish" (Wikipedia.com, accessed Nov. 2, 2014).

"List of sequenced bacterial genomes," (Wikipedia.com, accessed Jan. 24, 2014).

Office Action mailed Aug. 27, 2015 in U.S. Appl. No. 13/448,279, 42 pages.

U.S. Appl. No. 13/971,797.
U.S. Appl. No. 13/971,801.
U.S. Appl. No. 13/971,806.
U.S. Appl. No. 14/028,319.

\* cited by examiner

| | |
|---|---|
| Graph Construction via LFR | • Make a graph of all the het pairs that are within the expected distance. |
| Graph Construction via Mate Pairs | • Optionally, populate the graph of all the het pairs that are within the expected distance using mate pair data. |
| Graph Combination | • Combine the LFR-generated and Mate-pair generated graphs. |
| Graph Trimming | • Optionally, trim the graph using heuristics. |
| Graph Optimization | • Optimize the graph by making the minimum-spanning tree. |
| Contig Building | • Assemble contigs using the optimized graph. |
| Universal Phasing | • Use trio phasing to assign contigs to the parents. |

Fig. 3

Parent1: C-CGCAG
Parent2: G-ATTTA

Contig Phasing

Universal Phasing

Mom: C-CGCAG
Dad: G-ATTTA

|   | A | C | G | T |
|---|---|---|---|---|
| A |   |   |   |   |
| C | 9 |   |   |   |
| G | 7 |   |   |   |
| T |   |   |   |   |

C        A
   G        C (A in reality)

|   | A | C | G | T |
|---|---|---|---|---|
| A |   |   |   |   |
| C | 9 |   |   | 8 |
| G | 7 |   |   | 12 |
| T |   |   |   |   |

Fig. 12

Strong Connectivity

|   | A | C | G | T |
|---|---|---|---|---|
| A |   |   |   |   |
| C |   | 15 |   |   |
| G |   |   |   | 9 |
| T |   |   |   |   |

C        C
   G        T

Weak Connectivity

|   | A | C | G | T |
|---|---|---|---|---|
| A |   |   |   |   |
| C |   | 5 |   |   |
| G |   |   |   | 3 |
| T |   |   |   |   |

|  | Improved Amplification Protocol | SurePlex amplified | Genomic control, not amplified |
|---|---|---|---|
| Sum of Deltas | 55.4 | 280.5 | 36.1 |
| Average | 0.6 | 3.0 | 0.4 |
| 90$^{th}$ percentile | 1.2 | 5.0 | 0.6 |
| R GC bias | -0.050 | -0.319 | 0.089 |
| R$^2$ GC bias | 0.003 | 0.102 | 0.008 |
| Fold spread of data | 4.5 | 64 | 3.0 |
| Amplification | ~25,000 | ~50,000 | 0 |

Figure 16

| Sample | Ethnicity | Number of Heterozygous Phased SNPs | LFR Phasing Rate | Haploid Fragment coverage (cells) | Fragment Size for N50 DNA (kb) | Fragment Size for N25 DNA (kb) | DNA Bases Sequenced (Gb) LFR + STD | N50 Contig Length (kb) |
|---|---|---|---|---|---|---|---|---|
| NA19240-Replicate 1 | Yoruban | 2,386,741 | 91% | 38 (9.4) | 64 | 84 | 237+176 | 1,210 |
| NA19240-Replicate 2 | Yoruban | 2,433,621 | 91% | 51 (12.7) | 66 | 96 | 313+176 | 1,010 |
| NA19240-10 cell pipeline 2.0 | Yoruban | 2,369,433 | 89% | 54.3 (13.6)* | 80 | 120 | 308+176 | 943 |
| NA19240-Replicate 1 High Coverage | Yoruban | 2,578,903 | 96% | 48 (11.9) | 82 | 116 | 509+176 | 1,429 |
| NA19240-Replicates 1&2 combined | Yoruban | 2,646,352 | 97% | 89 (22.1) | 65 | 90 | 550+176 | 1,577 |
| NA19240-Replicate 1 LFR only | Yoruban | 2,031,514 | 91% | 38 (9.4) | 64 | 84 | 237 | 1,036 |
| NA19240-Replicate 1 High Coverage LFR only pipeline 2.0 | Yoruban | 2,274,696 | 95% | 48 (11.9) | 82 | 116 | 509 | 1,282 |
| NA12877-Replicate 1 | European | 1,831,032 | 93% | 65 (16.3) | 74 | 104 | 258+218 | 530 |
| NA12877-Replicate 2 | European | 1,810,540 | 92% | 51 (12.7) | 76 | 106 | 238+218 | 535 |
| NA12877-Replicates 1&2 combined | European | 1,946,089 | 97% | 116 (29) | 75 | 105 | 496+218 | 600 |
| NA12885 | European | 1,850,409 | 92% | 46 (11.6) | 72 | 98 | 272+221 | 528 |
| NA12886 | European | 1,854,360 | 93% | 44 (11) | 66 | 88 | 293+216 | 535 |
| NA12891 | European | 1,825,427 | 90%* | 46 (11.6) | 80 | 112 | 280+246 | 545 |
| NA12892 | European | 1,917,442 | 93%* | 93 (23.3) | 94 | 138 | 285+213 | 553 |
| NA12892 LFR only | European | 1,720,750 | 97%* | 93 (23.3) | 94 | 138 | 285 | 525 |
| NA20431 High Coverage | European | 1,703,047 | 84%* | 30 (7.4) | 94 | 142 | 514+189 | 411 |

| Part A | NA12877 | NA19240 |
|---|---|---|
| Comparable heterozygous SNPs | 1726638 | 2209986 |
| Fraction of total phased heterozygous SNPs | 95% | 93% |
| Estimated discordant individual heterozygous SNPs per library in contig without flips | 96 | 64 |
| Discordance rate(%) | 0.0056 | 0.0029 |
| Discordance frequency | 1 in 17,986 het SNPs | 1 in 34,531 het SNPs |
| Phasing error rate (diploid genome lenght: 2700Mb male and 2850Mb female) | 1 in 28Mb | 1 in 44Mb |
| Part B | | |
| All 2+ HETs contigs | 8620 | 8132 |
| Estimated contigs with flips per library | 116 | 135 |
| % contigs affected | 1.35 | 2.20 |

FIG. 23

| | NA12877 | | | | NA19240 | | | |
|---|---|---|---|---|---|---|---|---|
| | Standard library SNPs/Replicate 1 phasing | Standard library SNPs/Replicate 2 phasing | Replicate 1 (3+ wells) | Replicate 2 (3+ wells) | Standard library SNPs/Replicate 1 phasing | Standard library SNPs/Replicate 2 phasing | Replicate 1 (3+ wells) | Replicate 2 (3+ wells) |
| de-novo-like heterozygous SNPs | 3,813 | 3,813 | 26,494 | 32,931 | 3,633 | 3,633 | 50,137 | 38,859 |
| Phased by LFR1 and LFR2 | 1,589 | 1,589 | 1,297 | 1,447 | 1,057 | 1,057 | 988 | 1,127 |
| Error-like | 2,224 | 2,224 | 25,197 | 31,484 | 2,576 | 2,576 | 49,139 | 37,732 |
| Error-like-phased | 243 | 286 | 433 | 463 | 282 | 227 | 556 | 854 |
| Error reduction factor | 9x | 8x | 58x | 68x | 9x | 11x | 88x | 44x |
| Avoided errors | 1,981 | 1,938 | 24,764 | 31,021 | 2,294 | 2,349 | 48,583 | 36,878 |

| Sample | Ethnicity | Coding Only | | Coding and TFBS | |
|---|---|---|---|---|---|
| | | Both Alleles | One Allele | Both Alleles | One Allele |
| NA19240 Replicate 1 | Yoruban | 47 | 79 | 182 | 162 |
| NA19240 Replicate 2 | Yoruban | 55 | 85 | 207 | 174 |
| NA19240-Replicate 1 High Coverage | Yoruban | 65 | 95 | 235 | 185 |
| NA19240-Replicates 1&2 combined | Yoruban | 65 | 99 | 241 | 197 |
| NA12877 Replicate 1 | European | 45 | 78 | 144 | 144 |
| NA12877 Replicate 2 | European | 44 | 82 | 146 | 141 |
| NA12877-Replicates 1&2 combined | European | 49 | 86 | 167 | 168 |
| NA12885 | European | 34 | 79 | 143 | 141 |
| NA12886 | European | 32 | 101 | 140 | 168 |
| NA12891 | European | 36 | 69 | 130 | 140 |
| NA12892 | European | 37 | 65 | 125 | 136 |
| NA20431 High Coverage | European | 36 | 70 | 115 | 127 |

FIG. 25

| Gene Symbol | Chr. | Position | Span (bp) | Gene region or TFBS | TFBS max score | TFBS Orientation | P1 variant | P1 TFBS score | P2 variant | P2 TFBS score | Ref | P1 % frequency | P2 % frequency |
|---|---|---|---|---|---|---|---|---|---|---|---|---|---|
| PDE4DIP | 1 | 144918957 | 183368 | CDS | | | A | | T | | T | 86 | 14 |
| | | 144930594 | | CDS | | | A | | C | | C | 85 | 15 |
| | | 144934080 | | AP1 | 10.7 | + | T | 6.7 | A | 10.7 | A | | |
| | | 144934761 | | Nkx2-5 | 9.4 | - | G | 5.1 | T | 9.4 | T | | |
| | | 144934860 | | Gata1 | 14.5 | - | T | 12.0 | C | 4.0 | C | | |
| | | 144935315 | | NKx3-1 | 11.5 | - | G | 11.5 | A | 8.2 | A | | |
| DNAJC10 | 2 | 183578218 | 64913 | TLX1-NFIC | 20.4 | - | C | 7.1 | T | 11.2 | C | 43 | 56 |
| | | 183580862 | | RREB1 | 24.4 | + | G | 12.0 | A | 9.5 | A | 34 | 64 |
| | | 183642697 | | CDS | | | T | | C | | C | | |
| | | 183642878 | | UTR3 | | | A | | G | | G | | |
| | | 183643131 | | UTR3 | | | T | | C | | C | 35 | 64 |
| EDEM1 | 3 | 5226415 | 32570 | Foxa2 | 17.4 | + | T | 13.4 | A | 6.9 | A | | |
| | | 5258078 | | UTR3 | | | A | | G | | G | 74 | 26 |
| | | 5258471 | | UTR3 | | | A | | G | | G | 74 | 26 |
| | | 5258985 | | UTR3 | | | C | | T | | T | 59 | 39 |
| VPS13A | 9 | 79782520 | 193137 | PARG-RXR | 20.3 | + | T | 8.5 | G | 11.4 | G | | |
| | | 79782820 | | STAT1 | 19.8 | - | T | 10.6 | G | 6.5 | G | | |
| | | 79986057 | | CDS | | | G | | A | | A | 31 | 69 |
| ALDH1L2 | 12 | 105415948 | 66380 | UTR3 | | | G | | A | | A | 9 | 91 |
| | | 105417406 | | UTR3 | | | T | | C | | C | 4 | 96 |
| | | 105479562 | | Lhx3 | 18.0 | | A | 13.4 | G | 9.5 | G | | |
| | | 105482184 | | En1 | 9.4 | | A | 8.0 | T | 4.7 | T | | |
| | | 105482338 | | NFKB1 | 16.6 | | G | 6.5 | C | 10.7 | C | | |
| UBE2G2 | 21 | 46186094 | 363302 | UTR3 | | | C | | T | | C | 33 | 66 |
| | | 46191270 | | UTR3 | | | T | | C | | C | 35 | 65 |
| | | 46221494 | | PLAG1 | 21.2 | + | C | 9.7 | G | 13.8 | G | | |
| | | 46225396 | | HNF1A | 19.0 | - | T | 13.1 | C | 11.4 | C | | |

FIG. 26

PROCESSING AND ANALYSIS OF COMPLEX NUCLEIC ACID SEQUENCE DATA

This application is a continuation-in-part of and claims the benefit of priority to U.S. patent application Ser. No. 12/816,365, filed on Jun. 15, 2010, which is a non-provisional of U.S. Provisional Patent Application No. 61/187,162, filed on Jun. 15, 2009.

CROSS-REFERENCE TO RELATED APPLICATIONS

This application claims the benefit of priority to U.S. Provisional Patent Application No. 61/517,196, filed Apr. 14, 2011, which is hereby incorporated by reference in its entirety.

This application claims the benefit of priority to U.S. Provisional Patent Application No. 61/527,428 filed on Aug. 25, 2011, which is hereby incorporated by reference in its entirety.

This application claims the benefit of priority to U.S. Provisional Patent Application No. 61/546,516 filed on Oct. 12, 2011, which is hereby incorporated by reference in its entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 5041-US.TXT, created on Jan. 22, 2013, 4,096 bytes, machine format IBM-PC, MS-Windows operating system, is hereby incorporated by reference in its entirety for all purposes.

BACKGROUND OF THE INVENTION

Improved techniques for analysis of complex nucleic acids are needed, particularly methods for improving sequence accuracy and for analyzing sequences that have a large number of errors introduced through nucleic acid amplification, for example.

Moreover, there is a need for improved techniques for determining the parental contribution to the genomes of higher organisms, i.e., haplotype phasing of human genomes. Methods for haplotype phasing, including computational methods and experimental phasing, are reviewed in Browning and Browning, Nature Reviews Genetics 12:703-7014, 2011.

SUMMARY OF THE INVENTION

The present invention provides techniques for analysis of sequence information resulting from sequencing of complex nucleic acids (as defined herein) that results in haplotype phasing, error reduction and other features that are based on algorithms and analytical techniques that were developed in connection with Long Fragment Read (LFR) technology.

According to one aspect of the invention, methods are provided for determining a sequence of a complex nucleic acid (for example, a whole genome) of one or more organisms, that is, an individual organism or a population of organisms. Such methods comprise: (a) receiving at one or more computing devices a plurality of reads of the complex nucleic acid; and (b) producing, with the computing devices, an assembled sequence of the complex nucleic acid from the reads, the assembled sequence comprising less than 1.0, 0.8, 0.7, 0.6, 0.5, 0.4, 0.3, 0.2, 0.1, 0.08, 0.07, 0.06, 0.05 or 0.04 false single nucleotide variant per megabase at a call rate of 70, 75, 80, 85, 90 or 95 percent or greater, wherein the methods are performed by one or more computing devices. In some aspects, a computer-readable non-transitory storage medium stores one or more sequences of instructions that comprise instructions which, when executed by one or more computing devices, cause the one or more computing devices to perform the steps of such methods.

According to one embodiment, in which such methods involve haplotype phasing, the method further comprises identifying a plurality of sequence variants in the assembled sequence and phasing the sequence variants (e.g., 70, 75, 80, 85, 90, 95 percent or more of the sequence variants) to produce a phased sequence, i.e., a sequence wherein sequence variants are phased. Such phasing information can be used in the context of error correction. For example, according to one embodiment, such methods comprise identifying as an error a sequence variant that is inconsistent with the phasing of at least two (or three or more) phased sequence variants.

According to another such embodiment, in such methods the step of receiving the plurality of reads of the complex nucleic acid comprises a computing device and/or a computer logic thereof receiving a plurality of reads from each of a plurality of aliquots, each aliquot comprising one or more fragments of the complex nucleic acid. Information regarding the aliquot of origin of such fragments is useful for correcting errors or for calling a base that otherwise would have been a "no call." According to one such embodiment, such methods comprise a computing device and/or a computer logic thereof calling a base at a position of said assembled sequence on the basis of preliminary base calls for the position from two or more aliquots. For example, methods may comprise calling a base at a position of said assembled sequence on the basis of preliminary base calls from at least two, at least three, at least four, or more than four aliquots. In some embodiments, such methods may comprise identifying a base call as true if it is present at least two, at least three, at least four aliquots, or more than four aliquots. In some embodiments, such methods may comprise identifying a base call as true if it is present at least a majority (or a least 60%, at least 75%, or at least 80%) of the aliquots for which a preliminary base call is made for that position in the assembled sequence. According to another such embodiment, such methods comprise a computing device and/or a computer logic thereof identifying a base call as true if it is present three or more times in reads from two or more aliquots.

According to another such embodiment, the aliquot from which the reads originate is determined by identifying an aliquot-specific tag (or set of aliquot-specific tags) that is attached to each fragment. Such aliquot-specific tags optionally comprise an error-correction or error-detection code (e.g., a Reed-Solomon error correction code). According to one embodiment of the invention, upon sequencing a fragment and attached aliquot-specific tag, the resulting read comprises tag sequence data and fragment sequence data. If the tag sequence data is correct, i.e., if the tag sequence matches the sequence of a tag used for aliquot identification, or, alternatively, if the tag sequence data has one or more errors that can be corrected using the error-correction code, reads including such tag sequence data can be used for all purposes, particularly for a first computer process (e.g., being executed on one or more computing devices) that requires tag sequence data and produces a first output, including without limitation haplotype phasing, sample multiplexing, library multiplexing, phasing, or any error correction process that is based on correct tag sequence data (e.g., error correction processes that are based on identifying the aliquot of origin for a particular read). If the tag sequence is incorrect and cannot be corrected, then reads that include such incorrect tag sequence data are not discarded but instead are used in a second computer process (e.g., being executed by one or more computing devices) that does not require tag sequence data, including without limitation mapping, assembly, and pool-based statistics, and that produces a second output.

According to another embodiment, such methods further comprise: a computing device and/or a computer logic thereof providing a first phased sequence of a region of the complex nucleic acid, the region comprising a short tandem repeat; a computing device and/or a computer logic thereof comparing reads (e.g. regular or mate-pair reads) of the first phased sequence of the region with reads of a second phased sequence of the region (e.g., using sequence converage); and a computing device and/or a computer logic thereof identifying an expansion of the short tandem repeat in one of the first phased sequence or the second phased sequence based on the comparison.

According to another embodiment, the method further comprises a computing device and/or a computer logic thereof obtaining genotype data from at least one parent of the organism and producing an assembled sequence of the complex nucleic acid from the reads and the genotype data.

According to another embodiment, the method further comprises a computing device and/or a computer logic thereof performing steps that comprise: aligning a plurality of the reads for a first region of the complex nucleic acid, thereby creating an overlap between the aligned reads; identifying N candidate hets within the overlap; clustering the space of $2^N$ to $4^N$ possibilities or a selected subspace thereof, thereby creating a plurality of clusters; identifying two clusters with the highest density, each identified cluster comprising a substantially noise-free center; and repeating the foregoing steps for one or more additional regions of the complex nucleic acid. The identified clusters for each region can define contigis, and these contigs can be matched with each other to form to sets of contigs, one for each haplotype.

According to another embodiment, such methods further comprise providing an amount of the complex nucleic acid, and sequencing the complex nucleic acid to produce the reads.

According to another embodiment, in such methods the complex nucleic acid is selected from the group consisting of a genome, an exome, a transcriptome, a methylome, a mixture of genomes of different organisms, and a mixture of genomes of different cell types of an organism.

According to another aspect of the invention, an assembled human genome sequence is provided that is produced by any of the foregoing methods. For example, one or more computer-readable non-transitory storage media stores an assembled human genome sequence that is produced by any of the foregoing methods. According to another aspect, a computer-readable non-transitory storage medium stores one or more sequences of instructions that comprise instructions which, when executed by one or more computing devices, cause the one or more computing devices to perform any, some, or all of the foregoing methods.

According to another aspect of the invention, methods are provided for determining a whole human genome sequence, such methods comprising: (a) receiving, at one or more computing devices, a plurality of reads of the genome; and (b) producing, with the one or more computing devices, an assembled sequence of the genome from the reads, the assembled sequence comprising less than 600 false heterozygous single nucleotide variants per gigabase at a genome call rate of 70% or greater. According to one embodiment, the assembled sequence of the genome has a genome call rate of 70% or more and an exome call rate of 70% or greater. In some aspects, a computer-readable non-transitory storage medium stores one or more sequences of instructions that comprise instructions which, when executed by one or more computing devices, cause the one or more computing devices to perform any of the methods of the invention described herein.

According to another aspect of the invention, methods are provided for determining a whole human genome sequence, such methods comprising: (a) receiving, at one or more computing devices, a plurality of reads from each of a plurality of aliquots, each aliquot comprising one or more fragments of the genome; and (b) producing, with the one or more computing devices, a phased, assembled sequence of the genome from the reads that comprises less than 1000 false single nucleotide variants per gigabase at a genome call rate of 70% or greater. In some aspects, a computer-readable non-transitory storage medium stores one or more sequences of instructions that comprise instructions which, when executed by one or more computing devices, cause the one or more computing devices to perform such methods.

BRIEF DESCRIPTION OF THE DRAWINGS

FIG. 3 shows the general architecture of the LFR algorithm.

FIG. 12 shows error detection using LFR.

FIG. 13 shows an example of a method of decreasing the number of false negatives in which a confident heterozygous SNP call could be made despite a small number of reads.

FIG. 16 shows data relating to GC bias resulting from amplification using two MDA protocols. The average cycle number across the entire plate was determined and subtracted that from each individual marker to compute a "delta cycle" number. The delta cycle was plotted against the GC content of the 1000 base pairs surrounding each marker in order to indicate the relative GC bias of each sample (not shown). The absolute value of each delta cycle was summed to create the "sum of deltas" measurement. A low sum of deltas and a relatively flat plotting of the data against GC content yields a well-represented whole genome sequence. The sum of deltas was 61 for our MDA method and 287 for the SurePlex-amplified DNA, indicating that our protocol produced much less GC bias than the SurePlex protocol.

FIG. 20 shows a comparison of haplotyping performance between genome assemblies. Variant calls for standard and LFR assembled libraries were combined and used as loci for phasing except where specified. The LFR phasing rate was based on a calculation of parental phased heterozygous SNPs. *For those individuals without parental genome data (NA12891, NA12892, and NA20431) the phasing rate was calculated by dividing the number of phased heterozygous SNPs by the number of heterozygous SNPs expected to be real (number of attempted to be phased SNPs—50,000 expected errors). N50 calculations are based on the total assembled length of all contigs to the NCBI build 36 (build 37 in the case of NA19240 10 cell and high coverage and NA20431 high coverage) human reference genome. Haploid fragment coverage is four times greater than the number of cells as a result of all DNA being denatured to single stranded prior to being dispersed across a 384 well plate. The insufficient amount of starting DNA explains lower phasing efficiency in the NA20431 genome. #The 10 cell sample was measured by individual well coverage to contain more than 10 cells, which is likely the result of these cells being in various stages of the cell cycle during collection. The phasing rate ranged from 84% to 97%.

FIG. 21 depicts a flipped and unflipped relationship between heterozygous SNP pairs, respectively. The strength is defined by employing fuzzy logic operations on the elements of the shared aliquot matrix. (d) Graph optimization: The graph is optimized via a minimum spanning tree operation. (e) Contig generation: Each sub-tree is reduced to a contig by keeping the first heterozygous SNP unchanged and flipping or not flipping the other heterozygous SNPs on the sub-tree, based on their paths to the first heterozygous SNP. The designation of Parent 1 (P1) and Parent 2 (P2) to each contig is arbitrary. The gaps in the chromosome-wide tree define the boundaries for different sub-trees/contigs on that chromosome. (f) Mapping LFR contigs to parental chromosomes: Using parental information, a Mom or Dad label is placed on the P1 and P2 haplotypes of each contig.

FIG. 22 shows haplotype discordance between replicate LFR libraries. Two replicate libraries from samples NA12877 and NA19240 were compared at all shared phased heterozygous SNP loci. This is a comprehensive comparison, because most phased loci are shared between the two libraries.

FIG. 23 shows error reduction enabled by LFR. Standard library heterozygous SNP calls alone and in combination with LFR calls were phased independently by replicate LFR libraries. In general, LFR introduced approximately 10-fold more false positive variant calls. This most likely occurred as a result of the stochastic incorporation of incorrect bases during phi29-based multiple displacement amplification. Importantly, if heterozygous SNP calls are required to be phased and are found in three or more independent wells, the error reduction is dramatic and the result is better than the standard library without error correction. LFR can remove errors from the standard library as well, improving call accuracy by approximately 10-fold.

FIG. 25 shows the number of genes with multiple detrimental variations in each analysed sample.

FIG. 26 shows genes with allelic expression differences and TFBS-altering SNPs in NA20431. Out of a nonexhaustive list of genes that demonstrated significant allelic differences in expression, six genes were found with SNPs that altered TFBSs and correlated with the differences in expression seen between alleles. All positions are given relative to NCBI build 37. "CDS" stands for coding sequence and "UTR3" for 3' untranslated region.

DETAILED DESCRIPTION OF THE INVENTION

As used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and/or methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

Sequencing Systems and Data Analysis

In some embodiments, sequencing of DNA samples (e.g., such as samples representing whole human genomes) may be performed by a sequencing system. Two examples of sequencing systems are illustrated in FIG. 1.

Figure 1A:
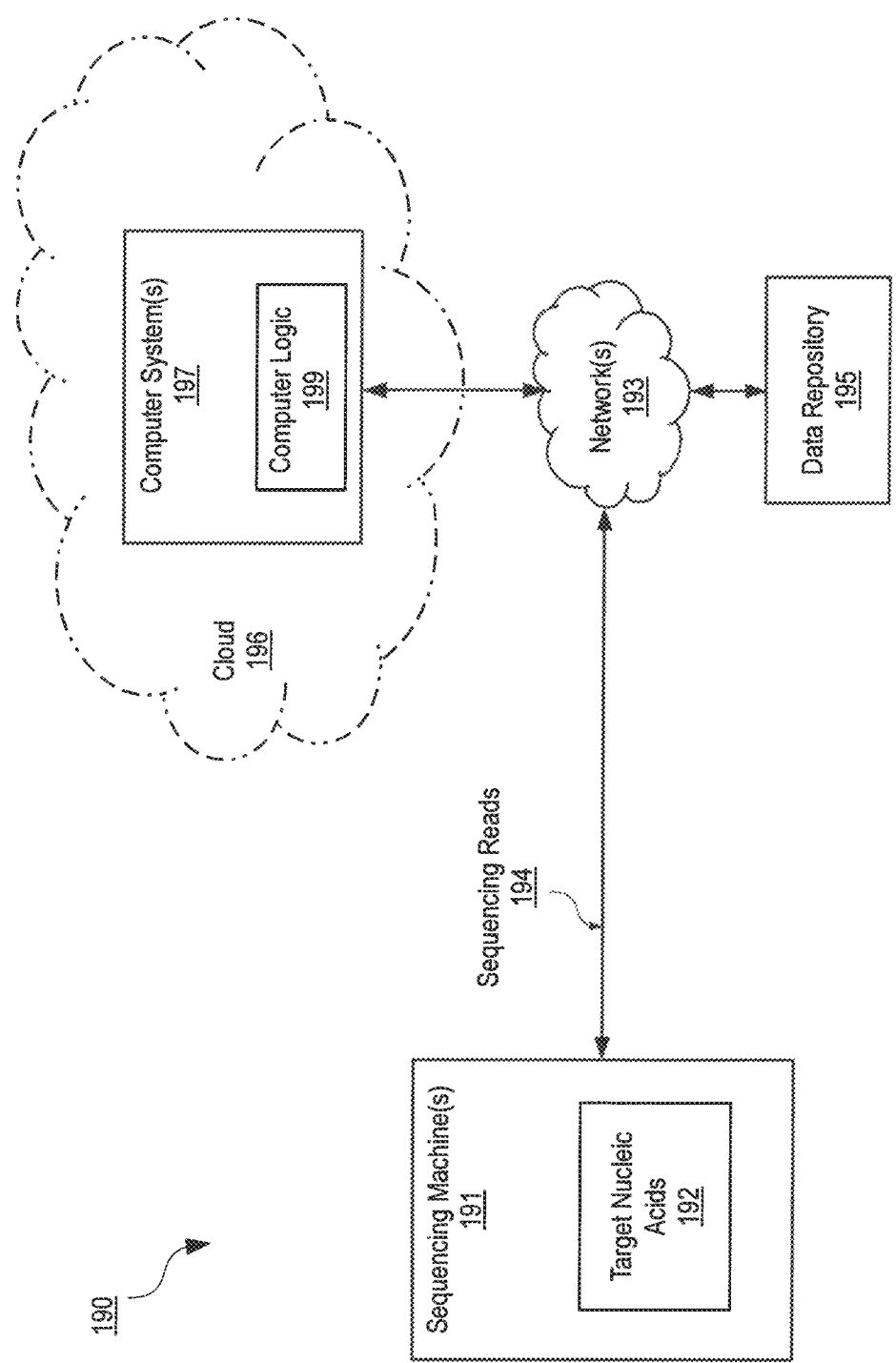
FIGS. 1A and 1B shows examples of sequencing systems.
Figure 1B:
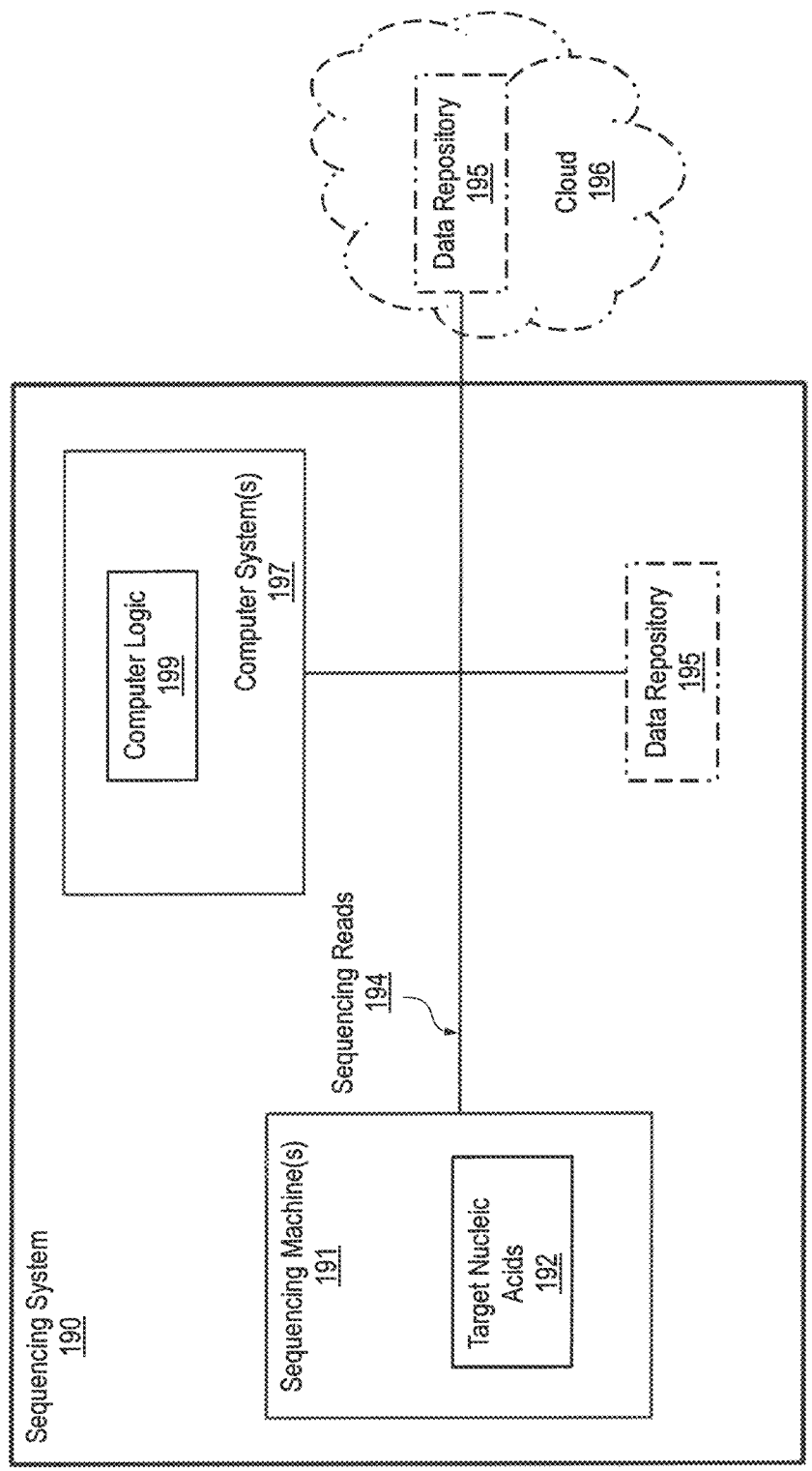

FIGS. 1A and 1B are block diagrams of example sequencing systems 190 that are configured to perform the techniques and/or methods for nucleic acid sequence analysis according to the embodiments described herein. A sequencing system 190 can include or be associated with multiple subsystems such as, for example, one or more sequencing machines such as sequencing machine 191, one or more computer systems such as computer system 197, and one or more data repositories such as data repository 195. In the embodiment illustrated in FIG. 1A, the various subsystems of system 190 may be communicatively connected over one or more networks 193, which may include packet-switching or other types of network infrastructure devices (e.g., routers, switches, etc.) that are configured to facilitate information exchange between remote systems. In the embodiment illustrated in FIG. 1B, sequencing system 190 is a sequencing device in which the various subsystems (e.g., such as sequencing machine(s) 191, computer system(s) 197, and possibly a data repository 195) are components that are communicatively and/or operatively coupled and integrated within the sequencing device.

In some operational contexts, data repository 195 and/or computer system(s) 197 of the embodiments illustrated in FIGS. 1A and 1B may be configured within a cloud computing environment 196. In a cloud computing environment, the storage devices comprising a data repository and/or the computing devices comprising a computer system may be allocated and instantiated for use as a utility and on-demand; thus, the cloud computing environment provides as services the infrastructure (e.g., physical and virtual machines, raw/block storage, firewalls, load-balancers, aggregators, networks, storage clusters, etc.), the platforms (e.g., a computing device and/or a solution stack that may include an operating system, a programming language execution environment, a database server, a web server, an application server, etc.), and the software (e.g., applications, application programming interfaces or APIs, etc.) necessary to perform any storage-related and/or computing tasks.

It is noted that in various embodiments, the techniques described herein can be performed by various systems and devices that include some or all of the above subsystems and components (e.g., such as sequencing machines, computer systems, and data repositories) in various configurations and form factors; thus, the example embodiments and configurations illustrated in FIGS. 1A and 1B are to be regarded in an illustrative rather than a restrictive sense.

Sequencing machine 191 is configured and operable to receive target nucleic acids 192 derived from fragments of a biological sample, and to perform sequencing on the target nucleic acids. Any suitable machine that can perform sequencing may be used, where such machine may use various sequencing techniques that include, without limitation, sequencing by hybridization, sequencing by ligation, sequencing by synthesis, single-molecule sequencing, optical sequence detection, electro-magnetic sequence detection, voltage-change sequence detection, and any other now-known or later-developed technique that is suitable for generating sequencing reads from DNA. In various embodiments, a sequencing machine can sequence the target nucleic acids and can generate sequencing reads that may or may not include gaps and that may or may not be mate-pair (or paired-end) reads. As illustrated in FIGS. 1A and 1B, sequencing machine 191 sequences target nucleic acids 192 and obtains sequencing reads 194, which are transmitted for (temporary and/or persistent) storage to one or more data repositories 195 and/or for processing by one or more computer systems 197.

Data repository 195 may be implemented on one or more storage devices (e.g., hard disk drives, optical disks, solid-state drives, etc.) that may be configured as an array of disks (e.g., such as a SCSI array), a storage cluster, or any other suitable storage device organization. The storage device(s) of a data repository can be configured as internal/integral components of system 190 or as external components (e.g., such as external hard drives or disk arrays) attachable to system 190 (e.g., as illustrated in FIG. 1B), and/or may be communicatively interconnected in a suitable manner such as, for example, a grid, a storage cluster, a storage area network (SAN), and/or a network attached storage (NAS) (e.g., as illustrated in FIG. 1A). In various embodiments and implementations, a data repository may be implemented on the storage devices as one or more file systems that store information as files, as one or more databases that store information in data records, and/or as any other suitable data storage organization.

Computer system 197 may include one or more computing devices that comprise general purpose processors (e.g., Central Processing Units, or CPUs), memory, and computer logic 199 which, along with configuration data and/or operating system (OS) software, can perform some or all of the techniques and methods described herein, and/or can control the operation of sequencing machine 191. For example, any of the methods described herein (e.g., for error correction, haplotype phasing, etc.) can be totally or partially performed by a computing device including a processor that can be configured to execute logic 199 for performing various steps of the methods. Further, although method steps may be presented as numbered steps, it is understood that steps of the methods described herein can be performed at the same time (e.g., in parallel by a cluster of computing devices) or in a different order. The functionalities of computer logic 199 may be implemented as a single integrated module (e.g., in an integrated logic) or may be combined in two or more software modules that may provide some additional functionalities.

In some embodiments, computer system 197 may be a single computing device. In other embodiments, computer system 197 may comprise multiple computing devices that may be communicatively and/or operatively interconnected in a grid, a cluster, or in a cloud computing environment. Such multiple computing devices may be configured in different form factors such as computing nodes, blades, or any other suitable hardware configuration. For these reasons, computer system 197 in FIGS. 1A and 1B is to be regarded in an illustrative rather than a restrictive sense.

Figure 2:
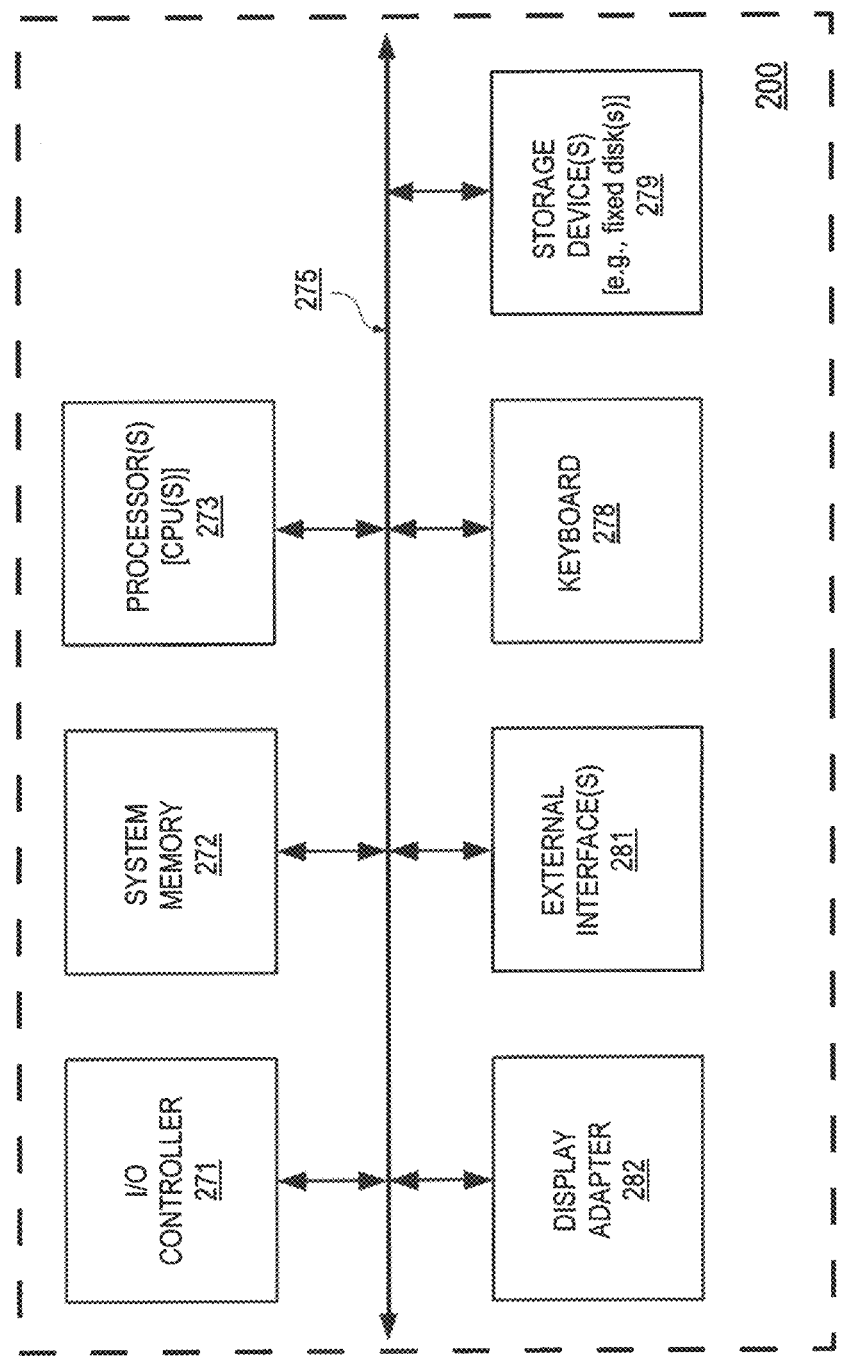
FIG. 2 shows an example of a computing device that can be used in, or in conjunction with, a sequencing machine and/or a computer system.

FIG. 2 is a block diagram of an example computing device 200 that can be configured to execute instructions for performing various data-processing and/or control functionalities as part of sequencing machine(s) and/or computer system(s).

In FIG. 2, computing device 200 comprises several components that are interconnected directly or indirectly via one or more system buses such as bus 275. Such components may include, but are not limited to, keyboard 278, persistent storage device(s) 279 (e.g., such as fixed disks, solid-state disks, optical disks, and the like), and display adapter 282 to which one or more display devices (e.g., such as LCD monitors, flat-panel monitors, plasma screens, and the like) may be coupled. Peripherals and input/output (I/O) devices, which couple to I/O controller 271, can be connected to computing device 200 by any number of means known in the art including, but not limited to, one or more serial ports, one or more parallel ports, and one or more universal serial buses (USBs). External interface(s) 281 (which may include a network interface card and/or serial ports) can be used to connect computing device 200 to a network (e.g., such as the Internet or a local area network (LAN)). External interface(s) 281 may also include a number of input interfaces that can receive information from various external devices such as, for example, a sequencing machine or any component thereof. The interconnection via system bus 275 allows one or more processors (e.g., CPUs) 273 to communicate with each connected component and to execute (and/or control the execution of) instructions from system memory 272 and/or from storage device(s) 279, as well as the exchange of information between various components. System memory 272 and/or storage device(s) 279 may be embodied as one or more computer-readable non-transitory storage media that store the sequences of instructions executed by processor(s) 273, as well as other data. Such computer-readable non-transitory storage media include, but is not limited to, random access memory (RAM), read-only memory (ROM), an electro-magnetic medium (e.g., such as a hard disk drive, solid-state drive, thumb drive, floppy disk, etc.), an optical medium such as a compact disk (CD) or digital versatile disk (DVD), flash memory, and the like. Various data values and other structured or unstructured information can be output from one component or subsystem to another component or subsystem, can be presented to a user via display adapter 282 and a suitable display device, can be sent through external interface(s) 281 over a network to a remote device or a remote data repository, or can be (temporarily and/or permanently) stored on storage device(s) 279.

Any of the methods and functionalities performed by computing device 200 can be implemented in the form of logic using hardware and/or computer software in a modular or integrated manner. As used herein, "logic" refers to a set of instructions which, when executed by one or more processors (e.g., CPUs) of one or more computing devices, are operable to perform one or more functionalities and/or to return data in the form of one or more results or data that is used by other logic elements. In various embodiments and implementations, any given logic may be implemented as one or more software components that are executable by one or more processors (e.g., CPUs), as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a standalone software application, as a client in a client-server system, as a server in a client-server system, as one or more software modules, as one or more libraries of functions, and as one or more static and/or dynamically-linked libraries. During execution, the instructions of any particular logic may be embodied as one or more computer processes, threads, fibers, and any other suitable run-time entities that can be instantiated on the hardware of one or more computing devices and can be allocated computing resources that may include, without limitation, memory, CPU time, storage space, and network bandwidth.

Techniques and Algorithms for the LFR Process

Basecalling

The overall method for sequencing target nucleic acids using the compositions and methods of the present invention is described herein and, for example, in U.S. Patent Application Publication 2010/0105052-A1; published patent application numbers WO2007120208, WO2006073504, WO2007133831, and US2007099208, and U.S. patent application Ser. Nos. 11/679,124; 11/981,761; 11/981,661; 11/981,605; 11/981,793; 11/981,804; 11/451,691; 11/981,607; 11/981,767; 11/982,467; 11/451,692; 11/541,225; 11/927,356; 11/927,388; 11/938,096; 11/938,106; 10/547,214; 11/981,730; 11/981,685; 11/981,797; 11/934,695; 11/934,697; 11/934,703; 12/265,593; 11/938,213; 11/938,221; 12/325,922; 12/252,280; 12/266,385; 12/329,365; 12/335,168; 12/335,188; and 12/361,507, which are incorporated herein by reference in their entirety for all purposes. See also Drmanac et al., *Science* 327, 78-81, 2010. Long Fragment Read (LFR) methods have been disclosed in U.S. patent application Ser. Nos. 12/816,365, 12/329,365, 12/266,385, and 12/265,593, and in U.S. Pat. Nos. 7,906,285, 7,901,891, and 7,709,197, which are hereby incorporated by reference in their entirety. Further details and improvements are provided herein.

In some embodiments, data extraction will rely on two types of image data: bright-field images to demarcate the positions of all DNBs on a surface, and sets of fluorescence images acquired during each sequencing cycle. Data extraction software can be used to identify all objects with the bright-field images and then for each such object, the software can be used to compute an average fluorescence value for each sequencing cycle. For any given cycle, there are four data points, corresponding to the four images taken at different wavelengths to query whether that base is an A, G, C or T. These raw data points (also referred to herein as "base calls") are consolidated, yielding a discontinuous sequencing read for each DNB.

A computing device can assemble the population of identified bases to provide sequence information for the target nucleic acid and/or identify the presence of particular sequences in the target nucleic acid. For example, the computing device may assemble the population of identified bases in accordance with the techniques and algorithms described herein by executing various logic; an example of such logic is software code written in any suitable programming language such as Java, C++, Perl, Python, and any other suitable conventional and/or object-oriented programming language. When executed in the form of one or more computer processes, such logic may read, write, and/or otherwise process structured and unstructured data that may be stored in various structures on persistent storage and/or in volatile memory; examples of such storage structures include, without limitation, files, tables, database records, arrays, lists, vectors, variables, memory and/or processor registers, persistent and/or memory data objects instantiated from object-oriented classes, and any other suitable data structures. In some embodiments, the identified bases are assembled into a complete sequence through alignment of overlapping sequences obtained from multiple sequencing cycles performed on multiple DNBs. As used herein, the term "complete sequence" refers to the sequence of partial or whole genomes as well as partial or whole target nucleic acids. In further embodiments, assembly methods performed by one or more computing devices or computer logic thereof utilize algorithms that can be used to "piece together" overlapping sequences to provide a complete sequence. In still further embodiments, reference tables are used to assist in assembling the identified sequences into a complete sequence. A reference table may be compiled using existing sequencing data on the organism of choice. For example human genome data can be accessed through the National Center for Biotechnology Information at ftp.ncbi.nih.gov/refseq/release, or through the J. Craig Venter Institute at www.jcvi.org/researchhuref/. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein. Exemplary methods for calling variations in a polynucleotide sequence compared to a reference polynucleotide sequence and for polynucleotide sequence assembly (or reassembly), for example, are provided in U.S. Patent Publication No. 2011-0004413, entitled "Method and System for Calling Variations in a Sample Polynucleotide Sequence with Respect to a Reference Polynucleotide Sequence", which is incorporated herein by reference for all purposes.

In any of the embodiments of the invention discussed herein, a population of nucleic acid templates and/or DNBs may comprise a number of target nucleic acids to substantially cover a whole genome or a whole target polynucleotide. As used herein, "substantially covers" means that the amount of nucleotides (i.e., target sequences) analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, Genomics, 2: 231-239 (1988); Vingron et al, J. Mol. Biol., 235: 1-12 (1994); and like references.

In some embodiments, four images, one for each color dye, are generated for each queried position of a complex nucleotide that is sequenced. The position of each spot in an image and the resulting intensities for each of the four colors is determined by adjusting for crosstalk between dyes and background intensity. A quantitative model can be fit to the resulting four-dimensional dataset. A base is called for a given spot, with a quality score that reflects how well the four intensities fit the model.

Basecalling of the four images for each field can be performed in several steps by one or more computing devices or computer logic thereof. First, the image intensities are corrected for background using modified morphological "image open" operation. Since the locations of the DNBs line up with the camera pixel locations, the intensity extraction is done as a simple read-out of pixel intensities from the background corrected images. These intensities are then corrected for several sources of both optical and biological signal cross-talks, as described below. The corrected intensities are then passed to a probabilistic model that ultimately produces for each DNB a set of four probabilities of the four possible basecall outcomes. Several metrics are then combined to compute the basecall score using pre-fitted logistic regression.

Intensity Correction:

Several sources of biological and optical cross-talks are corrected using linear regression model implemented as computer logic that is executed by one or more computing devices. The linear regression was preferred over de-convolution methods that are computationally more expensive and produced results with similar quality. The sources of optical cross-talks include filter band overlaps between the four fluorescent dye spectra, and the lateral cross-talks between neighboring DNBs due to light diffraction at their close proximities. The biological sources of cross-talks include incomplete wash of previous cycle, probe synthesis errors and probe "slipping" contaminating signals of neighboring positions, incomplete anchor extension when interrogating "outer" (more distant) bases from anchors. The linear regression is used to determine the part of DNB intensities that can be predicted using intensities of either neighboring DNBs or intensities from previous cycle or other DNB positions. The part of the intensities that can be explained by these sources of cross-talk is then subtracted from the original extracted intensities. To determine the regression coefficients, the intensities on the left side of the linear regression model need to be composed primarily of only "background" intensities, i.e., intensities of DNBs that would not be called the given base for which the regression is being performed. This requires pre-calling step that is done using the original intensities. Once the DNBs that do not have a particular basecall (with reasonable confidence) are selected, a computing device or computer logic thereof performs a simultaneous regression of the cross-talk sources:

$$I_{background}^{Base} \approx I_{DNBneighbor1}^{Base} + \ldots + \\ I_{DNBneighborN}^{Base} + I_{DNB}^{Base2} + I_{DNB}^{Base3} + \\ I_{DNB}^{Base4} + I_{DNBpreviousCycle}^{Base} + \\ I_{DNBotherPosition1}^{Base} + \ldots + \\ I_{DNBotherPositionN}^{Base} + \epsilon$$

The neighbor DNB cross-talk is corrected both using the above regression. Also, each DNB is corrected for its particular neighborhood using a linear model involving all neighbors over all available DNB positions.

Basecall Probabilities:

Calling bases using maximum intensity does not account for the different shapes of background intensity distributions of the four bases. To address such possible differences, a probabilistic model was developed based on empirical probability distributions of the background intensities. Once the intensities are corrected, a computing device or computer logic thereof pre-calls some DNBs using maximum intensities (DNBs that pass a certain confidence threshold) and uses these pre-called DNBs to derive the background intensity distributions (distributions of intensities of DNBs that are not called a given base). Upon obtaining such distributions, the computing device can compute for each DNB a tail probability under that distribution that describes the empirical probability of the intensity being background intensity. Therefore, for each DNB and each of the four intensities, the computing device or logic thereof can obtain and store their probabilities of being background ($p_{BG}^A$, $p_{BG}^C$, $p_{BG}^G$, $p_{BG}^T$). Then the computing device can compute the probabilities of all possible basecall outcomes using these probabilities. The possible basecall outcomes need to describe also spots that can be double or in general multiple-occupied or not occupied by a DNB. Combining the computed probabilities with their prior probabilities (lower prior for multiple-occupied or empty spots) gives rise to the probabilities of the 16 possible outcomes:

$$p^A = \frac{!\, p_{BG}^A + p_{BG}^C + p_{BG}^G + p_{BG}^T}{\sum p} * p_{SingleBase}^{prior}$$

$$p^{AC} = \frac{!\, p_{BG}^A + !\, p_{BG}^C + p_{BG}^G + p_{BG}^T}{\sum p} * p_{DoubleOccupied}^{prior}$$

$$p^{ACG} = \frac{!\, p_{BG}^A + !\, p_{BG}^C + !\, p_{BG}^G + p_{BG}^T}{\sum p} * p_{TripleOccupied}^{prior}$$

$$p^{ACGT} = \frac{!\, p_{BG}^A + !\, p_{BG}^C + !\, p_{BG}^G + !\, p_{BG}^T}{\sum p} * p_{QuadrupleOccupied}^{prior}$$

$$p^N = \frac{p_{BG}^A + p_{BG}^C + p_{BG}^G + p_{BG}^T}{\sum p} * p_{EmptySpot}^{prior}$$

These 16 probabilities can then be combined to obtain a reduced set of four probabilities for the four possible basecalls. That is:

$$p_{4base}^A = p^A + \tfrac{1}{2}(p^{AC} + p^{AG} + p^{AT}) + \tfrac{1}{3}(p^{ACG} + p^{ACT} + p^{AGT}) + \tfrac{1}{4} p^{ACGT} + \tfrac{1}{4} p^N$$

Score Computation:

Logistic regression was used to derive the score computation formula. A computing device or computer logic thereof fitted the logistic regression to mapping outcomes of the basecalls using several metrics as inputs. The metrics included probability ratio between the called base and the next highest base, called base intensity, indicator variable of the basecall identity, and metrics describing the overall clustering quality of the field. All metrics were transformed to be collinear with log-odds-ratio between concordant and discordant calls. The model was refined using cross-validation. The logit function with the final logistic regression coefficients was used to compute the scores in production.

Mapping and Assembly

In further embodiments, read data is encoded in a compact binary format and includes both a called base and quality score. The quality score is correlated with base accuracy. Analysis software logic, including sequence assembly software, can use the score to determine the contribution of evidence from individual bases with a read.

Reads may be "gapped" due to the DNB structure. Gap sizes vary (usually +/−1 base) due to the variability inherent in enzyme digestion. Due to the random-access nature of cPAL, reads may occasionally have an unread base ("no-call") in an otherwise high-quality DNB. Read pairs are mated.

Mapping software logic capable of aligning read data to a reference sequence can be used to map data generated by the sequencing methods described herein. When executed by one or more computing devices, such mapping logic will generally be tolerant of small variations from a reference sequence, such as those caused by individual genomic variation, read errors, or unread bases. This property often allows direct reconstruction of SNPs. To support assembly of larger variations, including large-scale structural changes or regions of dense variation, each arm of a DNB can be mapped separately, with mate pairing constraints applied after alignment.

As used herein, the term "sequence variant" or simply "variant" includes any variant, including but not limited to a substitution or replacement of one or more bases; an insertion or deletion of one or more bases (also referred to as an "indel"); inversion; conversion; duplication; or copy number variation (CNV); trinucleotide repeat expansion; structural variation (SV; e.g., intrachromosomal or inter-chromosomal rearrangement, e.g., a translocation); etc. In a diploid genome, a "heterozygosity" or "het" is two different alleles of a particular gene in a gene pair. The two alleles may be different mutants or a wild type allele paired with a mutant. The present methods can also be used in the analysis of non-diploid organisms, whether such organisms are haploid/monoploid (N=1, where N=haploid number of chromosomes), or polyploid, or aneuploid.

Assembly of sequence reads can in some embodiments utilize software logic that supports DNB read structure (mated, gapped reads with non-called bases) to generate a diploid genome assembly that can in some embodiments be leveraged off of sequence information generating LFR methods of the present invention for phasing heterozygote sites.

Methods of the present invention can be used to reconstruct novel segments not present in a reference sequence.

Algorithms utilizing a combination of evidential (Bayesian) reasoning and de Bruijn graph-based algorithms may be used in some embodiments. In some embodiments, statistical models empirically calibrated to each dataset can be used, allowing all read data to be used without pre-filtering or data trimming. Large scale structural variations (including without limitation deletions, translocations, and the like) and copy number variations can also be detected by leveraging mated reads.

Phasing LFR Data

FIG. 3 describes the main steps in the phasing of LFR data. These steps are as follows:

(1) Graph Construction Using LFR Data:

One or more computing devices or computer logic thereof generates an undirected graph, where the vertices represent the heterozygous SNPs, and the edges represent the connection between those heterozygous SNPs. The edge is composed of the orientation and the strength of the connection. The one or more computing devices may store such graph in storage structures include, without limitation, files, tables, database records, arrays, lists, vectors, variables, memory and/or processor registers, persistent and/or memory data objects instantiated from object-oriented classes, and any other suitable temporary and/or persistent data structures.

(2) Graph Construction Using Mate Pair Data:

Step 2 is similar to step 1, where the connections are made based on the mate pair data, as opposed to the LFR data. For a connection to be made, a DNB must be found with the two heterozygous SNPs of interest in the same read (same arm or mate arm).

(3) Graph Combination:

A computing device or computer logic thereof represents of each of the above graphs is via an N×N sparse matrix, where N is the number of candidate heterozygous SNPs on that chromosome. Two nodes can only have one connection in each of the above methods. Where the two methods are combined, there may be up to two connections for two nodes. Therefore, the computing device or computer logic thereof may use a selection algorithm to select one connection as the connection of choice. For these studies, it was discovered that the quality of the mate-pair data was significantly inferior to that of the LFR data. Therefore, only the LFR-derived connections were used.

(4) Graph Trimming:

A series of heuristics were devised and applied, by a computing device, to stored graph data in order to remove some of the erroneous connections. More precisely, a node must satisfy the condition of at least two connections in one direction and one connection in the other direction; otherwise, it is eliminated.

(5) Graph Optimization:

A computing device or computer logic thereof optimized the graph by generating the minimum-spanning tree (MST). The energy function was set to −|strength|. During this process, where possible, the lower strength edges get eliminated, due to the competition with the stronger paths. Therefore, MST provides a natural selection for the strongest and most reliable connections.

(6) Contig Building:

Once the minimum-spanning tree is generated and/or stored in computer-readable medium, a computing device or logic thereof can re-orient all the nodes with taking one node (here, the first node) constant. This first node is the anchor node. For each of the nodes, the computing device then finds the path to the anchor node. The orientation of the test node is the aggregate of the orientations of the edges on the path.

(7) Universal Phasing:

After the above steps, a computing device or logic thereof phases each of the contigs that are built in the previous step(s). Here, the results of this part are referred to as pre-phased, as opposed to phased, indicating that this is not the final phasing. Since the first node was chosen arbitrarily as the anchor node, the phasing of the whole contig is not necessarily in-line with the parental chromosomes. For universal phasing, a few heterozygous SNPs on the contig for which trio information is available are used. These trio heterozygous SNPs are then used to identify the alignment of the contig. At the end of the universal phasing step, all the contigs have been labeled properly and therefore can be considered as a chromosome-wide contig.

Contig Making

Figure 4:
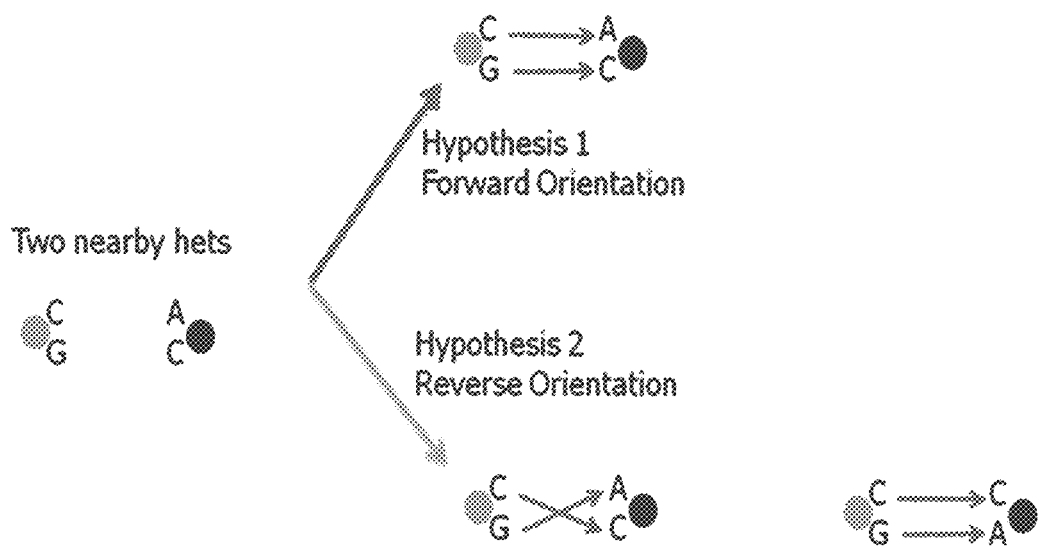
FIG. 4 shows pairwise analysis of nearby heterozygous SNPs.

In order to make contigs, for each heterozygous SNP-pair, a computing device or computer logic therefor tests two hypotheses: the forward orientation and reverse orientation. A forward orientation means that the two heterozygous SNPs are connected the same way they are originally listed (initially alphabetically). A reverse orientation means that the two heterozygous SNPs are connected in reverse order of their original listing. FIG. 4 depicts the pairwise analysis of nearby heterozygous SNPs involving the assignment of forward and reverse orientations to a heterozygous SNP-pair.

Figure 5:
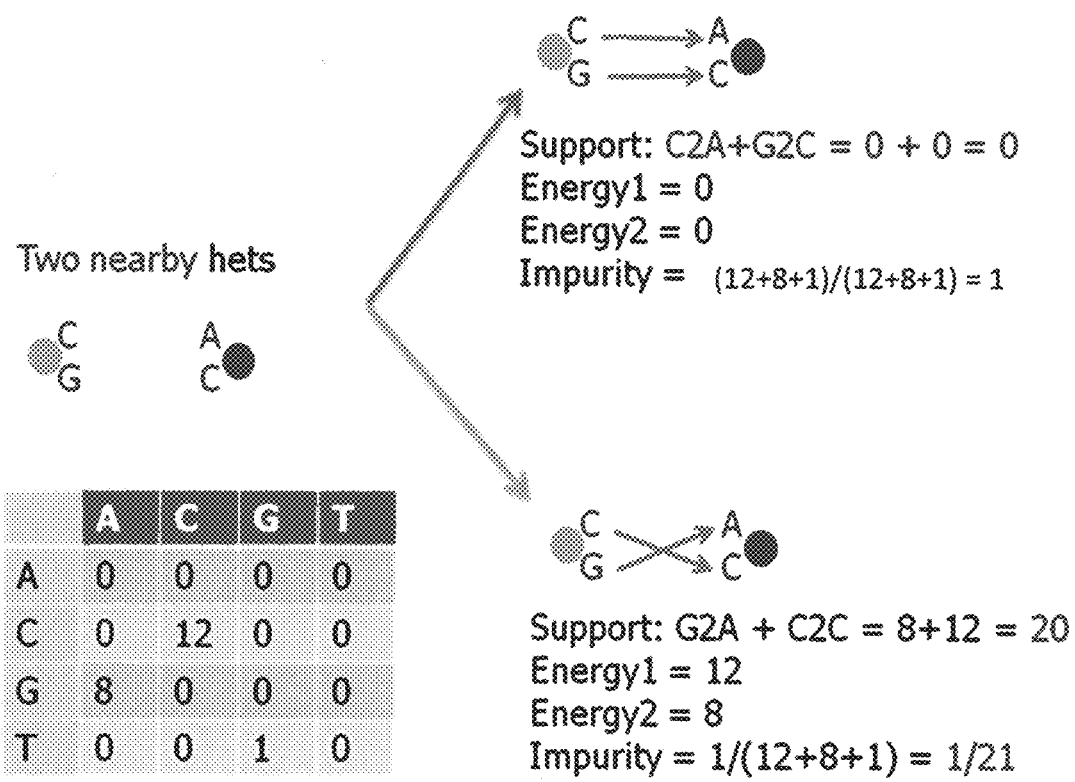
FIG. 5 shows an example of the selection of an hypothesis and the assignment of a score to the hypothesis.

Each orientation will have a numerical support, showing the validity of the corresponding hypothesis. This support is a function of the 16 cells of the connectivity matrix shown in FIG. 5, which shows an example of the selection of a hypothesis, and the assignment of a score to it. To simplify the function, the 16 variables are reduced to 3: Energy1, Energy2 and Impurity. Energy 1 and Energy2 are two highest value cells corresponding to each hypothesis. Impurity is the ratio of the sum of all the other cells (than the two corresponding to the hypothesis) to the total sum of the cells in the matrix. The selection between the two hypotheses is done based on the sum of the corresponding cells. The hypothesis with the higher sum is the winning hypothesis. The following calculations are only used to assign the strength of that hypothesis. A strong hypothesis is the one with a high value for Energy1 and Energy2, and a low value for Impurity.

The three metrics Energy1, Energy2 and Impurity are fed into a fuzzy inference system (FIG. 6), in order to reduce their effects into a single value—score—between (and including) 0 and 1. The fuzzy interference system (FIS) is implemented as a computer logic that can be executed by one or more computing devices.

Figure 6:
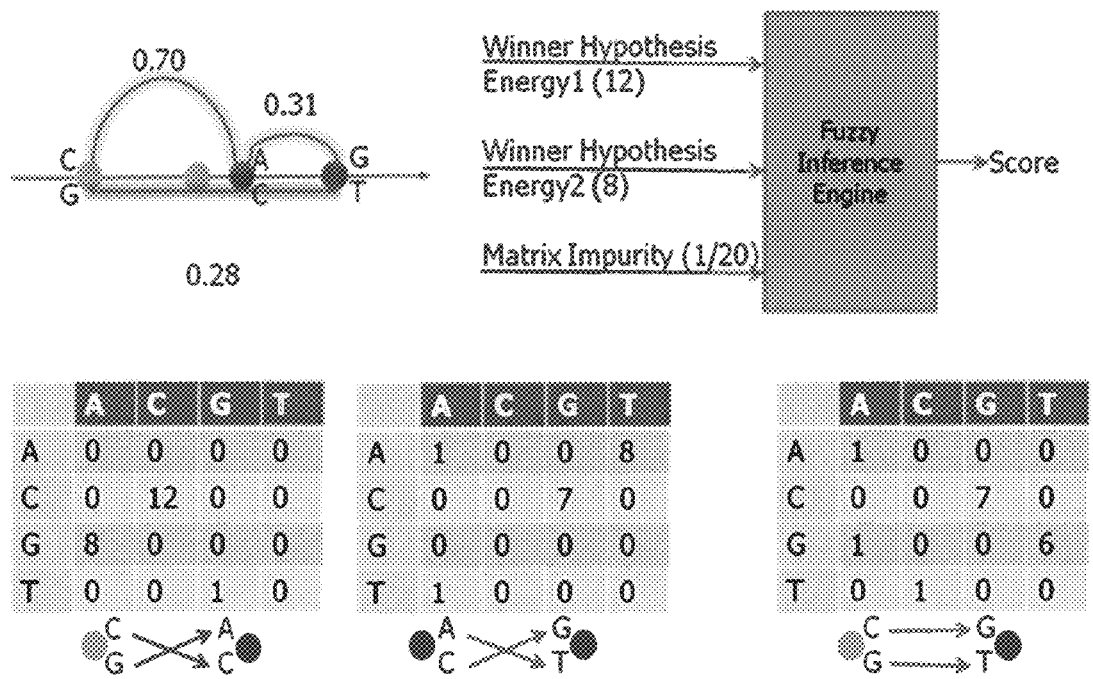
FIG. 6 shows graph construction.

The connectivity operation is done for each heterozygous SNP pair that is within a reasonable distance up to the expected contig length (e.g., 20-50 Kb). FIG. 6 shows graph construction, depicting some exemplary connectivities and strengths for three nearby heterozygous SNPs.

The rules of the fuzzy inference engine are defined as follows:

(1) If Energy1 is small and Energy2 is small, then Score is very small.

(2) If Energy1 is medium and Energy2 is small, then Score is small.

(3) If Energy1 is medium and Energy2 is medium, then Score is medium.

(4) If Energy1 is large and Energy2 is small, then Score is medium.

(5) If Energy1 is large and Energy2 is medium, then Score is large.

(6) If Energy1 is large and Energy2 is large, then Score is very large.

(7) If Impurity is small, then Score is large.
(8) If Impurity is medium, then Score is small.
(9) If Impurity is large, then Score is very small.

For each variable, the definition of Small, Medium and Large is different, and is governed by its specific membership functions After exposing the fuzzy inference system (FIS) to each variable set, the contribution of the input set on the rules is propagated through the fuzzy logic system, and a single (de-fuzzified) number is generated at the output—score. This score is limited between 0 and 1, with 1 showing the highest quality.

Figure 7:
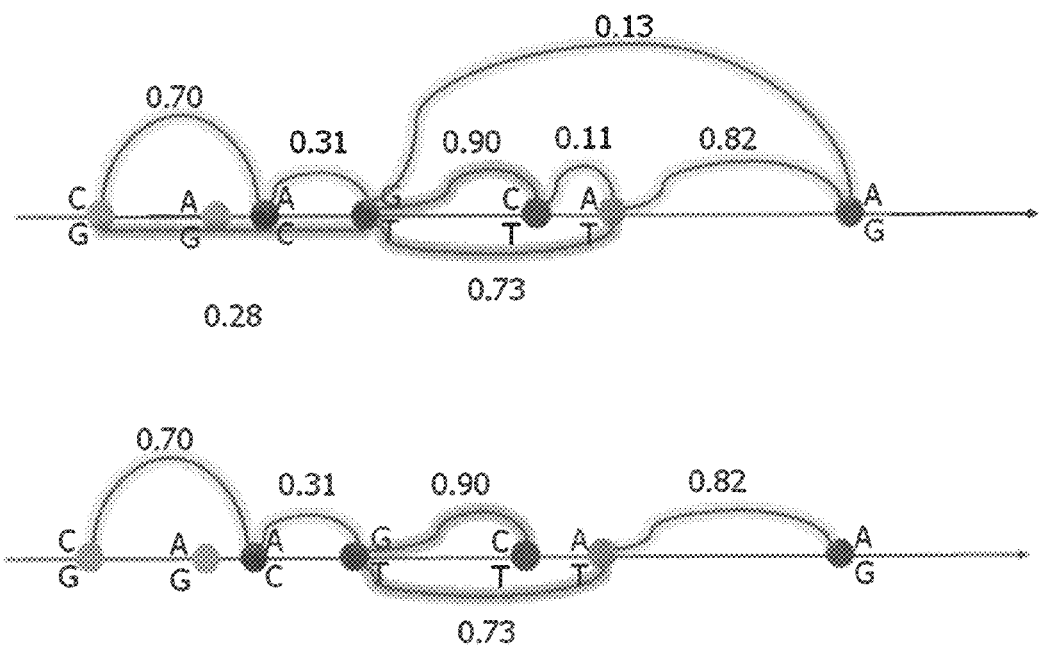
FIG. 7 shows graph optimization.

After the application of the FIS to each node pair, a computing device or computer logic thereof constructs a complete graph. FIG. 7 shows an example of such graph. The nodes are colored according to the orientation of the winning hypothesis. The strength of each connection is derived from the application of the FIS on the heterozygous SNP pair of interest. Once the preliminary graph is constructed (the top plot of FIG. 7), the computing device or computer logic thereof optimizes the graph (the bottom plot of FIG. 7) and reduces it to a tree. This optimization process is done by making a Minimum Spanning Tree (MST) from the original graph. The MST guarantees a unique path from each node to any other node.

Figure 8:
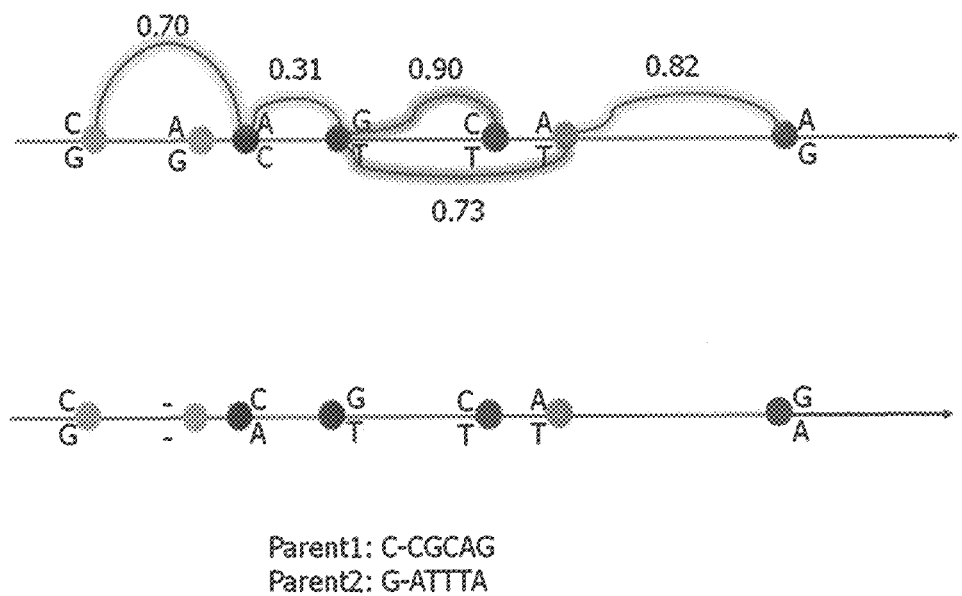
FIG. 8 shows contig alignment.

FIG. 7 shows graph optimization. In this application, the first node on each contig is used as the anchor node, and all the other nodes are oriented to that node. Depending on the orientation, each hit would have to either flip or not, in order to match the orientation of the anchor node. FIG. 8 shows the contig alignment process for the given example. At the end of this process, a phased contig is made available.

Figure 9:
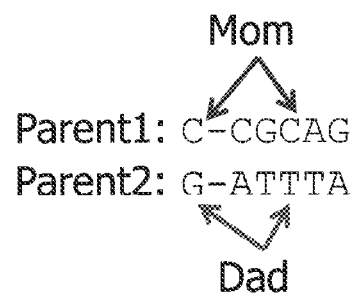
FIG. 9 shows parent-assisted universal phasing.

At this point in the process of phasing, the two haplotypes are separated. Although it is known that one of these haplotypes comes from the Mom and one from the Dad, it is not known exactly which one comes from which parent. In the next step of phasing, a computing device or computer logic thereof attempts to assign the correct parental label (Mom/Dad) to each haplotype. This process is referred to as the Universal Phasing. In order to do so, one needs to know the association of at least a few of the heterozygous SNPs (on the contig) to the parents. This information can be obtained by doing a Trio (Mom-Dad-Child) phasing. Using the trio's sequenced genomes, some loci with known parental associations are identified—more specifically when at least one parent is homozygous. These associations are then used by the computing device or computer logic thereof to assign the correct parental label (Mom/Dad) to the whole contigs, that is, to perform parent-assisted universal phasing (FIG. 9).

In order to guarantee high accuracy, the following may be performed: (1) when possible (e.g., in the case of NA19240), acquiring the trio information from multiple sources (e.g., Internal and 1000Genomes), and using a combination of such sources; (2) requiring the contigs to include at least two known trio-phased loci; (3) eliminating the contigs that have a series of trio-mismatches in a row (indicating a segmental error); and (4) eliminating the contigs that have a single trio-mismatch at the end of the trio loci (indicating a potential segmental error).

Figure 10:
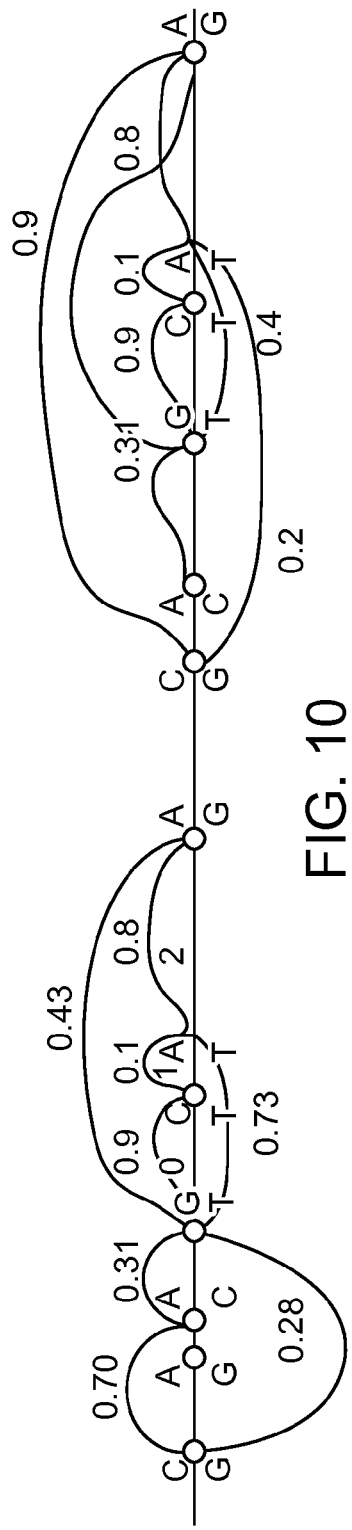
FIG. 10 shows natural contig separations.

FIG. 10 shows natural contig separations. Whether parental data are used or not, contigs often do not continue naturally beyond a certain point. Reasons for contig separation are: (1) more than usual DNA fragmentation or lack of amplification in certain areas, (2) low heterozygous SNP density, (3) poly-N sequence on the reference genome, and (4) DNA repeat regions (prone to mis-mapping).

Figure 11:
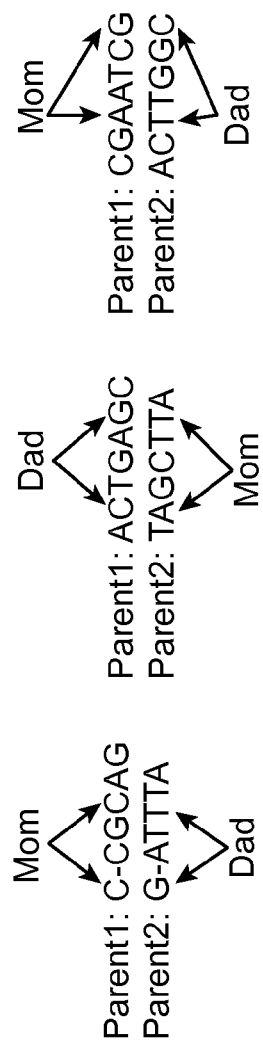
FIG. 11 shows universal phasing. Sequences: "Mom: C-CGCAG TAGCTTA CGAATCG" (SEQ ID NO:1); "Dad: G-ATTTA ACTGAGC ACTTGGC" (SEQ ID NO:2).

FIG. 11 shows Universal Phasing. One of the major advantages of Universal Phasing is the ability to obtain the full chromosomal "contigs." This is possible because each contig (after Universal Phasing) carries haplotypes with the correct parental labels. Therefore, all the contigs that carry the label Mom can be put on the same haplotype; and a similar operation can be done for Dad's contigs.

Another of the major advantages of the LFR process is the ability to dramatically increase the accuracy of heterozygous SNP calling. FIG. 12 shows two examples of error detection resulting from the use of the LFR process. The first example is shown in FIG. 12 (left), in which the connectivity matrix does not support any of the expected hypotheses. This is an indication that one of the heterozygous SNPs is not really a heterozygous SNP. In this example, the A/C heterozygous SNP is in reality a homozygous locus (A/A), which was mislabeled as a heterozygous locus by the assembler. This error can be identified, and either eliminated or (in this case) corrected. The second example is shown in FIG. 13 (right), in which the connectivity matrix for this case supports both hypotheses at the same time. This is a sign that the heterozygous SNPerozygous calls are not real.

A "healthy" heterozygous SNP-connection matrix is one that has only two high cells (at the expected heterozygous SNP positions, i.e., not on a straight line). All other possibilities point to potential problems, and can be either eliminated, or used to make alternate basecalls for the loci of interest.

Another advantage of the LFR process is the ability to call heterozygous SNPs with weak supports (e.g., where it was hard to map DNBs due to the bias or mismatch rate). Since the LFR process requires an extra constraint on the heterozygous SNPs, one could reduce the threshold that a heterozygous SNP call requires in a non-LFR assembler. FIG. 13 demonstrates an example of this case in which a confident heterozygous SNP call could be made despite a small number of reads. In FIG. 13 (right) under a normal scenario the low number of supporting reads would have prevented any assembler to confidently call the corresponding heterozygous SNPs. However, since the connectivity matrix is "clean," one could more confidently assign heterozygous SNP calls to these loci.

Annotating SNPs in Splice Sites

Introns in transcribed RNAs need to be spliced out before they become mRNA. Information for splicing is embedded within the sequence of these RNAs, and is consensus based. Mutations in splicing site consensus sequence are causes to many human diseases (Faustino and Cooper, Genes Dev. 17:419-437, 2011). The majority of splice sites conform to a simple consensus at fixed positions around an exon. In this regard, a program was developed to annotate Splice Site mutations. In this program, consensus splice position models (www.life.umd.edu/labs/mount/RNAinfo) was used. A look-up is performed for a pattern: CAG|G in the 5'-end region of an exon ("|" denotes the beginning of exon), and MAG|GTRAG in the 3'-end region of the same exon ("|" denotes the ending of exon). Here M={A,C}, R={A,G}. Further, splicing consensus positions are classified into two types: type I, where consensus to the model is 100% required; and type II, where consensus to the model is preserved in >50% cases. Presumably, a SNP mutation in a type I position will cause the splicing to miss, whereas a SNP in a type II position will only decrease the efficiency of the splicing event.

The program logic for annotating splice site mutations comprises two parts. In part 1, a file containing model positions sequences from the input reference genome is generated. In part 2, the SNPs from a sequencing project are compared to these model positions sequences and report any type I and type II mutations. The program logic is exon-centric instead of intron-centric (for convenience in parsing the genome). For a given exon, in its 5'-end we look for the consensus "cAGg" (for positions −3, −2, −1, 0. 0 means the start of exon). Capital letters means type I positions, and lower-case letters means type II positions). In the 3'-end of the exon, a look-up is performed for the consensus "mag-GTrag" (for position sequence −3, −2, −1, 0, 1, 2, 3, 4). Exons from the genome release that do not confirm to these requirements are simply ignored (~5% of all cases). These exons fall into other minor classes of splice-site consensus and are not investigated by the program logic. Any SNP from the genome sequenced is compared to the model sequence at these genomic positions. Any mismatch in type I will be reported. Mismatch in type II positions are reported if the mutation departs from the consensus.

The above program logic detects the majority of bad splice-site mutations. The bad SNPs that are reported are definitely problematic. But there are many other bad SNPs causing splicing problem that are not detected by this program. For example, there are many introns within the human genome that do not confirm to the above-mentioned consensus. Also, mutations in bifurcation points in the middle of the intron may also cause splice problem. These splice-site mutations are not reported.

Annotation of SNPs Affecting Transcription Factor Binding Sites (TFBS).

JASPAR models are used for finding TFBSs from the released human genome sequences (either build 36 or build 37). JASPAR Core is a collection of 130 TFBS positional frequency data for vertebrates, modeled as matrices (Bryne et al., Nucl. Acids Res. 36:D102-D106, 2008; Sandelin et al., Nucl. Acids Res. 23:D91-D94, 2004). These models are downloaded from the JASPAR website (http://jaspar.genereg.net/cgi-bin/jaspar_db.pl?rm=browse&db=core&tax_group=vertebrates). These models are converted into Position Weight Matrices (PWMs) using the following formula: wi=log 2[(fi+p Ni½)/(Ni+Ni½)/p], where: fi is the observed frequency for the specific base at position I; Ni is the total observations at the position; and p the background frequency for the current nucleotide, which is defaulted to 0.25 (bogdan.org.ua/2006/09/11/position-frequency-matrix-to-position-weight-matrix-pfm2pwm.html; Wasserman and Sandelin, Nature Reviews, Genetics 5:P276-287, 2004). A specific program, mast (meme.sdsc.edu/meme/mast-intro.html), is used to search sequence segments within the genome for TFBS-sites. A program was run to extract TFBS-sites in the reference genome. The outline of steps is as follows: (i) For each gene with mRNA, extract [−5000, 1000] putative TFBS-containing regions from the genome, with 0 being the mRNA starting location. (ii) Run mast-search of all PWM-models for the putative TFBS-containing sequences. (iii) Select those hits above a given threshold. (iv) For regions with multiple or overlapping hits, select only 1-hit, the one with the highest mast-search score.

With the TFBS model-hits from the reference genome generated and/or stored in suitable computer-readable medium, a computing device or computer logic thereof can identify SNPs which are located within the hit-region. These SNPs will impact on the model, and a change in the hit-score. A second program was written to compute such changes in the hit-score, as the segment containing the SNP is run twice into the PWM model, once for the reference, and the second time for the one with the SNP substitution. A SNP causing the segment hit score to drop more than 3 is identified as a bad SNP.

Selection of genes with two bad SNPs. Genes with bad SNPs are classified into two categories: (1) those affecting the AA-sequence transcribed; and (2) those affecting the transcription binding site. For AA-sequence affecting, the following SNP subcategories are included:

(1) Nonsense or nonstop variations. These mutations either cause a truncated protein or an extended protein. In either situation, the function of the protein product is either completely lost or less efficient.

(2) Splice site variations. These mutations cause either the splice site for an intron to be destroyed (for those positions required to be 100% of a certain nucleotide by the model) or severely diminished (for those sites required to be >50% for a certain nucleotide by the model. The SNP causes the splice-site nucleotide to mutate to another nucleotide that is below 50% of consensus as predicted by the splice-site consensus sequence model). These mutations will likely produce proteins which are truncated, missing exons, or severely diminishing in protein product quantity.

(3) Polyphen2 annotation of AA variations. For SNPs that cause change in amino-acid sequence of a protein, but not its length, Polyphen2 (Adzhubei et al., Nat. Methods 7:248-249, 2010) was used as the main annotation tool. Polyphen2 annotates the SNP with "benign", "unknown, "possibly damaging", and "probably damaging". Both "possibly damaging" and "probably damaging" were identified as bad SNPs. These category assignments by Polyphen2 are based on structural predictions of the Polyphen2 software.

For transcription-binding site mutations the 75% of max-Score of the models was used based on the reference genome as a screening for TFBS-binding sites. Any model-hit in the region that is <=75% of maxScore are removed. For those remaining, if a SNP causes the hit-score to drop 3 or more, it is considered as a detrimental SNP.

Two classes of genes are reported. Class 1 genes are those that had at least 2-bad AA-affecting mutations. These mutations can be all on a single allele (Class 1.1), or spread on 2 distinct alleles (Class 1.2). Class 2 genes are a superset of the Class 1 set. Class 2 genes are genes contain at least 2-bad SNPs, irrespective it is AA-affecting or TFBS-site affecting. But a requirement is that at least 1 SNP is AA-affecting. Class 2 genes are those either in Class 1, or those that have 1 detrimental AA-mutation and 1 or more detrimental TFBS-affecting variations. Class 2.1 means that all these detrimental mutations are from a single allele, whereas Class 2.2 means that detrimental SNPs are coming from two distinct alleles.

The foregoing techniques and algorithms are applicable to methods for sequencing complex nucleic acids, optionally in conjunction with LFR processing prior to sequencing (LFR in combination with sequencing may be referred to as "LFR sequencing"), which are described in detail as follows. Such methods for sequencing complex nucleic acids may be performed by one or more computing devices that execute computer logic. An example of such logic is software code written in any suitable programming language such as Java, C++, Perl, Python, and any other suitable conventional and/or object-oriented programming language. When executed in the form of one or more computer processes, such logic may read, write, and/or otherwise process structured and unstructured data that may be stored in various structures on persistent storage and/or in volatile memory; examples of such storage structures include, without limitation, files, tables, database records, arrays, lists, vectors, variables, memory and/or processor registers, persistent and/or memory data objects instantiated from object-oriented classes, and any other suitable data structures.

Improving Accuracy in Long-Read Sequencing

In DNA sequencing using certain long-read technologies (e.g., nanopore sequencing), long (e.g., 10-100 kb) read lengths are available but generally have high false negative and false positive rates. The final accuracy of sequence from such long-read technologies can be significantly enhanced using haplotype information (complete or partial phasing) according to the following general process.

First, a computing device or computer logic thereof aligns reads to each other. A large number of heterozygous calls are expected to exist in the overlap. For example, if two to five 100 kb fragments overlap by a minimum of 10%, this results in >10 kb overlap, which could roughly translate to heterozygous loci. Alternatively, each long read is aligned to a reference genome, by which a multiple alignment of the reads would be implicitly obtained.

Once the multiple read alignments have been achieved, the overlap region can be considered. The fact that the overlap could include a large number (e.g., N=10) of het loci can be leveraged to consider combinations of hets. This combinatorial modality results in a large space ($4^N$ or $4\textasciicircum N$; if N=10, then $4^N=\sim 1$ million) of possibilities for the haplotypes. Of all of these $4^N$ points in the N-dimensional space, only two points are expected to contain biologically viable information, i.e., those corresponding to the two haplotypes. In other words, there is a noise suppression ratio of $4^N/2$ (here 1e6/2 or ~500,000). In reality, much of this $4^N$ space is degenerate, particularly since the sequences are already aligned (and therefore look alike), and also because each locus does not usually carry more than two possible bases (if it is a real het). Consequently, a lower bound for this space is actually $2^N$ (if N=10, then $2^N=\sim 1000$). Therefore, the noise suppression ratio could only be $2^N/2$ (here 1000/2=500), which is still quite impressive. As the number of the false positives and false negatives grow, the size of the space expands from $2^N$ to $4^N$, which in turn results in a higher noise suppression ratio. In other words, as the noise grows, it will automatically be more suppressed. Therefore, the output products are expected to retain only a very small (and rather constant) amount of noise, almost independently from the input noise. (The tradeoff is the yield loss in the noisier conditions.) Of course, these suppression ratios are altered if (1) the errors are systematic (or other data idiosyncrasies), (2) the algorithms are not optimal, (3) the overlapping sections are shorter, or (4) the coverage redundancy is less. N can be any integer greater than one, such as 2, 3, 5, 10, or more.

The following methodology is useful for increasing the accuracy of the long-read sequencing methods, which could have a large initial error rate.

First, a computing device or computer logic thereof aligns a few reads, for instance 5 reads or more, such as 10-20 reads. Assuming reads are ~100 kb, and the shared overlap is 10%, this results in a 10 kb overlap in the 5 reads. Also assume there is a het in every 1 Kb. Therefore, there would be a total of 10 hets in this common region.

Next, the computing device or computer logic thereof fills in a portion (e.g. just non-zero elements) or the whole matrix of $alpha^{10}$ possibilities (where alpha is between 2 and 4) for the above 10 candidate hets. In one implementation, only 2 out of $alpha^{10}$ cells of this matrix should be high density (e.g., as measured by a threshold, which can be predetermined or dynamic). These are the cells that correspond to the real hets. These two cells can be considered substantially noise-free centers. The rest should contain mostly 0 and occasionally 1 memberships, especially if the errors are not systematic. If the errors are systematic, there may be a clustering event (e.g., a third cell that has more than just 0 or 1), which makes the task more difficult. However, even in this case, the cluster membership for the false cluster should be significantly weaker (e.g., as measured by an absolute or relative amount) than that of the two expected clusters. The trade-off in this case is that the starting point should include more multiple sequences aligned, which relates directly to having longer reads or larger coverage redundancy.

The above step assume that the two viable clusters are observed among the overlapped reads. For a large number of false positives, this would not be the case. If this is the case, in the alpha-dimensional space, the expected two clusters will be blurred, i.e., instead of being single points with high density, they will be blurred clusters of M points around the cells of interest, where these cells of interest are the noise-free centers that are at the center of the cluster. This enables the clustering methods to capture the locality of the expected points, despite the fact that the exact sequence is not represented in each read. A cluster event may also occur when the clusters are blurred (i.e. there could be more than two centers), but in a similar manner as described above, a score (e.g., the total counts for the cells of a cluster) can be used to distinguish a weaker cluster from the two real clusters, for a diploid organism. The two real clusters can be used to create contigs, as described herein, for various regions, and the contigs can be matched into two groups to form haplotypes for a large region of the complex nucleic acid.

Finally, the computing device or computer logic thereof the population-based (known) haplotypes can be used to increase confidence and/or to provide extra guidance in finding the actual clusters. A way to enable this method is to provide each observed haplotype a weight, and to provide a smaller but non-zero value to the unobserved haplotypes. By doing so, one achieves a bias toward the natural haplotypes that have been observed in the population of interest.

Using Reads with Tag-Sequence Data with Uncorrected Errors

As discussed herein, according to one embodiment of the invention, a sample of a complex nucleic acid is divided into a number of aliquots (e.g., wells in a multi-well plate), amplified, and fragmented. Then, aliquot-specific tags are ligated to the fragments in order to identify the aliquot from which a particular fragment of a complex nucleic acid originates. The tags optionally include an error-correction code, e.g., a Reed-Solomon error correction (or error detection) code. When the fragment is sequenced, both the tag and the fragment of the complex nucleic acid sequence is sequenced. If there is an error in the tag sequence, and it is impossible to identify the aliquot from which the fragment originated, or to correct the sequence using the error-correction code, the entire read might be discarded, leading to the loss of much sequence data. It should be noted that reads comprising correct and corrected tag sequence data are high accuracy, but low yield, while reads comprising tag sequence data that cannot be corrected are low accuracy, but high yield. Instead, such sequence data is used for processes other than those that require such data in order to identify the aliquot of origin by means of the identity of the association of a particular tag with a particular aliquot. Examples of processes that require reads with correct (or corrected) tag sequence data include without limitation sample or library multiplexing, phasing, or error correction or any other process that requires a correct (or correctable) tag sequence.

Examples of processes that can employ reads with tag sequence data that are cannot be corrected include any other process, including without limitation mapping, reference-based and local de novo assembly, pool-based statistics (e.g., allele frequencies, location of de novo mutations, etc.).

Converting Long Reads to Virtual LFR

The algorithms that are designed for LFR (including the phasing algorithm) can be used for long reads by assigning a random virtual tag (with uniform distribution) to each of the (10-100 kb) long fragments. The virtual tag has the benefit of enabling a true uniform distribution for each code. LFR cannot achieve this level of uniformity due to the difference in the pooling of the codes and the difference in the decoding efficiency of the codes. A ratio of 3:1 (and up to 10:1) can be easily observed in the representation of any two codes in LFR. However, the virtual LFR process results in a true 1:1 ratio between any two codes.

Methods for Sequencing Complex Nucleic Acids

Overview

According to one aspect of the invention, methods are provided for sequencing complex nucleic acids. According to certain embodiments of the invention, methods are provided for sequencing very small amounts of such complex nucleic acids, e.g., 1 pg to 10 ng. Even after amplification, such methods result in an assembled sequence characterized by a high call rate and accuracy. According to other embodiments, aliquoting is used to identify and eliminate errors in sequencing of complex nucleic acids. According to another embodiment, LFR is used in connection with the sequencing of complex nucleic acids.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

The overall method for sequencing target nucleic acids using the compositions and methods of the present invention is described herein and, for example, in U.S. Patent Application Publications 2010/0105052 and US2007099208, and U.S. patent application Ser. No. 11/679,124 (published as US 2009/0264299); Ser. No. 11/981,761 (US 2009/0155781); Ser. No. 11/981,661 (US 2009/0005252); Ser. No. 11/981,605 (US 2009/0011943); Ser. No. 11/981,793 (US 2009-0118488); Ser. No. 11/451,691 (US 2007/0099208); Ser. No. 11/981,607 (US 2008/0234136); Ser. No. 11/981,767 (US 2009/0137404); Ser. No. 11/982,467 (US 2009/0137414); Ser. No. 11/451,692 (US 2007/0072208); Ser. No. 11/541,225 (US 2010/0081128; 11/927,356 (US 2008/0318796); Ser. No. 11/927,388 (US 2009/0143235); Ser. No. 11/938,096 (US 2008/0213771); Ser. No. 11/938,106 (US 2008/0171331); Ser. No. 10/547,214 (US 2007/0037152); Ser. No. 11/981,730 (US 2009/0005259); Ser. No. 11/981,685 (US 2009/0036316); Ser. No. 11/981,797 (US 2009/0011416); Ser. No. 11/934,695 (US 2009/0075343); Ser. No. 11/934,697 (US 2009/0111705); Ser. No. 11/934,703 (US 2009/0111706); Ser. No. 12/265,593 (US 2009/0203551); Ser. No. 11/938,213 (US 2009/0105961); Ser. No. 11/938,221 (US 2008/0221832); Ser. No. 12/325,922 (US 2009/0318304); Ser. No. 12/252,280 (US 2009/0111115); Ser. No. 12/266,385 (US 2009/0176652); Ser. No. 12/335,168 (US 2009/0311691); Ser. No. 12/335,188 (US 2009/0176234); Ser. No. 12/361,507 (US 2009/0263802), Ser. No. 11/981,804 (US 2011/0004413); and Ser. No. 12/329,365; published international patent application numbers WO2007120208, WO2006073504, and WO2007133831, all of which are incorporated herein by reference in their entirety for all purposes. Exemplary methods for calling variations in a polynucleotide sequence compared to a reference polynucleotide sequence and for polynucleotide sequence assembly (or reassembly), for example, are provided in U.S. patent publication No. 2011-0004413, (application Ser. No. 12/770,089) which is incorporated herein by reference in its entirety for all purposes. See also Drmanac et al., Science 327, 78-81, 2010. Also incorporated by reference in its entirety and for all purposes is copending related application Nos. 61/623,876 entitled "Identification Of Dna Fragments And Structural Variations."

This method includes extracting and fragmenting target nucleic acids from a sample. The fragmented nucleic acids are used to produce target nucleic acid templates that will generally include one or more adaptors. The target nucleic acid templates are subjected to amplification methods to form nucleic acid nanoballs, which are usually disposed on a surface. Sequencing applications are performed on the nucleic acid nanoballs of the invention, usually through sequencing by ligation techniques, including combinatorial probe anchor ligation ("cPAL") methods, which are described in further detail below. cPAL and other sequencing methods can also be used to detect specific sequences, such as including single nucleotide polymorphisms ("SNPs") in nucleic acid constructs of the invention, (which include nucleic acid nanoballs as well as linear and circular nucleic acid templates). The above-referenced patent applications and the cited article by Drmanac et al. provide additional detailed information regarding, for example: preparation of nucleic acid templates, including adapter design, inserting adapters into a genomic DNA fragment to produce circular library constructs; amplifying such library constructs to produce DNA nanoballs (DNBs); producing arrays of DNBs on solid supports; cPAL sequencing; and so on, which are used in connection with the methods disclosed herein.

As used herein, the term "complex nucleic acid" refers to large populations of nonidentical nucleic acids or polynucleotides. In certain embodiments, the target nucleic acid is genomic DNA; exome DNA (a subset of whole genomic DNA enriched for transcribed sequences which contains the set of exons in a genome); a transcriptome (i.e., the set of all mRNA transcripts produced in a cell or population of cells, or cDNA produced from such mRNA), a methylome (i.e., the population of methylated sites and the pattern of methylation in a genome); a microbiome; a mixture of genomes of different organisms, a mixture of genomes of different cell types of an organism; and other complex nucleic acid mixtures comprising large numbers of different nucleic acid molecules (examples include, without limitation, a microbiome, a xenograft, a solid tumor biopsy comprising both normal and tumor cells, etc.), including subsets of the aforementioned types of complex nucleic acids. In one embodiment, such a complex nucleic acid has a complete sequence comprising at least one gigabase (Gb) (a diploid human genome comprises approximately 6 Gb of sequence).

Nonlimiting examples of complex nucleic acids include "circulating nucleic acids" (CNA), which are nucleic acids circulating in human blood or other body fluids, including but not limited to lymphatic fluid, liquor, ascites, milk, urine, stool and bronchial lavage, for example, and can be distinguished as either cell-free (CF) or cell-associated nucleic acids (reviewed in Pinzani et al., Methods 50:302-307, 2010), e.g., circulating fetal cells in the bloodstream of a expecting mother (see, e.g., Kavanagh et al., J. Chromatol. B 878:1905-1911, 2010) or circulating tumor cells (CTC) from the bloodstream of a cancer patient (see, e.g., Allard et al., Clin Cancer Res. 10:6897-6904, 2004). Another example is genomic DNA from a single cell or a small number of cells, such as, for example, from biopsies (e.g., fetal cells biopsied from the trophectoderm of a blastocyst; cancer cells from needle aspiration of a solid tumor; etc.). Another example is pathogens, e.g., bacteria cells, virus, or other pathogens, in a tissue, in blood or other body fluids, etc.

As used herein, the term "target nucleic acid" (or polynucleotide) or "nucleic acid of interest" refers to any nucleic acid (or polynucleotide) suitable for processing and sequencing by the methods described herein. The nucleic acid may be single stranded or double-stranded and may include DNA, RNA, or other known nucleic acids. The target nucleic acids may be those of any organism, including but not limited to viruses, bacteria, yeast, plants, fish, reptiles, amphibians, birds, and mammals (including, without limitation, mice, rats, dogs, cats, goats, sheep, cattle, horses, pigs, rabbits, monkeys and other non-human primates, and humans). A target nucleic acid may be obtained from an individual or from a multiple individuals (i.e., a population). A sample from which the nucleic acid is obtained may contain a nucleic acids from a mixture of cells or even organisms, such as: a human saliva sample that includes human cells and bacterial cells; a mouse xenograft that includes mouse cells and cells from a transplanted human tumor; etc.

Target nucleic acids may be unamplified or the may be amplified by any suitable nucleic acid amplification method know in the art. Target nucleic acids may be purified according to methods known in the art to remove cellular and subcellular contaminants (lipids, proteins, carbohydrates, nucleic acids other than those to be sequenced, etc.), or they may be unpurified, i.e., include at least some cellular and subcellular contaminants, including without limitation intact cells that are disrupted to release their nucleic acids for processing and sequencing. Target nucleic acids can be obtained from any suitable sample using methods known in the art. Such samples include but are not limited to: tissues, isolated cells or cell cultures, bodily fluids (including, but not limited to, blood, urine, serum, lymph, saliva, anal and vaginal secretions, perspiration and semen); air, agricultural, water and soil samples, etc. In one aspect, the nucleic acid constructs of the invention are formed from genomic DNA.

High coverage in shotgun sequencing is desired because it can overcome errors in base calling and assembly. As used herein, for any given position in an assembled sequence, the term "sequence coverage redundancy," "sequence coverage" or simply "coverage" means the number of reads representing that position. It can be calculated from the length of the original genome (G), the number of reads (N), and the average read length (L) as N×L/G. Coverage also can be calculated directly by making a tally of the bases for each reference position. For a whole-genome sequence, coverage is expressed as an average for all bases in the assembled sequence. Sequence coverage is the average number of times a base is read (as described above). It is often expressed as "fold coverage," for example, as in "40× coverage," meaning that each base in the final assembled sequence is represented on an average of 40 reads.

As used herein, term "call rate" means a comparison of the percent of bases of the complex nucleic acid that are fully called, commonly with reference to a suitable reference sequence such as, for example, a reference genome. Thus, for a whole human genome, the "genome call rate" (or simply "call rate") is the percent of the bases of the human genome that are fully called with reference to a whole human genome reference. An "exome call rate" is the percent of the bases of the exome that are fully called with reference to an exome reference. An exome sequence may be obtained by sequencing portions of a genome that have been enriched by various known methods that selectively capture genomic regions of interest from a DNA sample prior to sequencing. Alternatively, an exome sequence may be obtained by sequencing a whole human genome, which includes exome sequences. Thus, a whole human genome sequence may have both a "genome call rate" and an "exome call rate." There is also a "raw read call rate" that reflects the number of bases that get an A/C/G/T designation as opposed to the total number of attempted bases. (Occasionally, the term "coverage" is used in place of "call rate," but the meaning will be apparent from the context).

Preparing Fragments of Complex Nucleic Acids

Nucleic Acid Isolation.

The target genomic DNA is isolated using conventional techniques, for example as disclosed in Sambrook and Russell, Molecular Cloning: A Laboratory Manual, cited supra. In some cases, particularly if small amounts of DNA are employed in a particular step, it is advantageous to provide carrier DNA, e.g. unrelated circular synthetic double-stranded DNA, to be mixed and used with the sample DNA whenever only small amounts of sample DNA are available and there is danger of losses through nonspecific binding, e.g. to container walls and the like.

According to some embodiments of the invention, genomic DNA or other complex nucleic acids are obtained from an individual cell or small number of cells with or without purification.

Long fragments are desirable for LFR. Long fragments of genomic nucleic acid can be isolated from a cell by a number of different methods. In one embodiment, cells are lysed and the intact nuclei are pelleted with a gentle centrifugation step. The genomic DNA is then released through proteinase K and RNase digestion for several hours. The material can be treated to lower the concentration of remaining cellular waste, e.g., by dialysis for a period of time (i.e., from 2-16 hours) and/or dilution. Since such methods need not employ many disruptive processes (such as ethanol precipitation, centrifugation, and vortexing), the genomic nucleic acid remains largely intact, yielding a majority of fragments that have lengths in excess of 150 kilobases. In some embodiments, the fragments are from about 5 to about 750 kilobases in lengths. In further embodiments, the fragments are from about 150 to about 600, about 200 to about 500, about 250 to about 400, and about 300 to about 350 kilobases in length. The smallest fragment that can be used for LFR is one containing at least two hets (approximately 2-5 kb), and there is no maximum theoretical size, although fragment length can be limited by shearing resulting from manipulation of the starting nucleic acid preparation. Techniques that produce larger fragments result in a need for fewer aliquots, and those that result in shorter fragments may require more aliquots.

Once the DNA is isolated and before it is aliquoted into individual wells it is carefully fragmented to avoid loss of material, particularly sequences from the ends of each fragment, since loss of such material can result in gaps in the final genome assembly. In one embodiment, sequence loss is avoided through use of an infrequent nicking enzyme, which creates starting sites for a polymerase, such as phi29 polymerase, at distances of approximately 100 kb from each other. As the polymerase creates a new DNA strand, it displaces the old strand, creating overlapping sequences near the sites of polymerase initiation. As a result, there are very few deletions of sequence.

A controlled use of a 5' exonuclease (either before or during amplification, e.g., by MDA) can promote multiple replications of the original DNA from a single cell and thus minimize propagation of early errors through copying of copies.

In other embodiments, long DNA fragments are isolated and manipulated in a manner that minimizes shearing or absorption of the DNA to a vessel, including, for example, isolating cells in agarose in agarose gel plugs, or oil, or using specially coated tubes and plates.

In some embodiments, further duplicating fragmented DNA from the single cell before aliquoting can be achieved by ligating an adaptor with single stranded priming overhang and using an adaptor-specific primer and phi29 polymerase to make two copies from each long fragment. This can generate four cells-worth of DNA from a single cell.

Fragmentation.

The target genomic DNA is then fractionated or fragmented to a desired size by conventional techniques including enzymatic digestion, shearing, or sonication, with the latter two finding particular use in the present invention.

Fragment sizes of the target nucleic acid can vary depending on the source target nucleic acid and the library construction methods used, but for standard whole-genome sequencing such fragments typically range from 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 300-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length. Longer fragments are useful for LFR.

In a further embodiment, fragments of a particular size or in a particular range of sizes are isolated. Such methods are well known in the art. For example, gel fractionation can be used to produce a population of fragments of a particular size within a range of basepairs, for example for 500 base pairs+50 base pairs.

In many cases, enzymatic digestion of extracted DNA is not required because shear forces created during lysis and extraction will generate fragments in the desired range. In a further embodiment, shorter fragments (1-5 kb) can be generated by enzymatic fragmentation using restriction endonucleases. In a still further embodiment, about 10 to about 1,000,000 genome-equivalents of DNA ensure that the population of fragments covers the entire genome. Libraries containing nucleic acid templates generated from such a population of overlapping fragments will thus comprise target nucleic acids whose sequences, once identified and assembled, will provide most or all of the sequence of an entire genome.

In some embodiments of the invention, a controlled random enzymatic ("CORE") fragmentation method is utilized to prepare fragments. CoRE fragmentation is an enzymatic endpoint assay, and has the advantages of enzymatic fragmentation (such as the ability to use it on low amounts and/or volumes of DNA) without many of its drawbacks (including sensitivity to variation in substrate or enzyme concentration and sensitivity to digestion time).

In one aspect, the present invention provides a method of fragmentation referred to herein as Controlled Random Enzymatic (CORE) fragmentation, which can be used alone or in combination with other mechanical and enzymatic fragmentation methods known in the art. CoRE fragmentation involves a series of three enzymatic steps. First, a nucleic acid is subjected to an amplification method that is conducted in the present of dNTPs doped with a proportion of deoxyuracil ("dU") or uracil ("U") to result in substitution of dUTP or UTP at defined and controllable proportions of the T positions in both strands of the amplification product. Any suitable amplification method can be used in this step of the invention. In certain embodiment, multiple displacement amplification (MDA) in the presence of dNTPs doped with dUTP or UTP in a defined ratio to the dTTP is used to create amplification products with dUTP or UTP substituted into certain points on both strands.

After amplification and insertion of the uracil moieties, the uracils are then excised, usually through a combination of UDG, EndoVIII, and T4PNK, to create single base gaps with functional 5' phosphate and 3' hydroxyl ends. The single base gaps will be created at an average spacing defined by the frequency of U in the MDA product. That is, the higher the amount of dUTP, the shorter the resulting fragments. As will be appreciated by those in the art, other techniques that will result in selective replacement of a nucleotide with a modified nucleotide that can similarly result in cleavage can also be used, such as chemically or other enzymatically susceptible nucleotides.

Treatment of the gapped nucleic acid with a polymerase with exonuclease activity results in "translation" or "translocation" of the nicks along the length of the nucleic acid until nicks on opposite strands converge, thereby creating double strand breaks, resulting a relatively population of double-stranded fragments of a relatively homogenous size. The exonuclease activity of the polymerase (such as Taq polymerase) will excise the short DNA strand that abuts the nick while the polymerase activity will "fill in" the nick and subsequent nucleotides in that strand (essentially, the Taq moves along the strand, excising bases using the exonuclease activity and adding the same bases, with the result being that the nick is translocated along the strand until the enzyme reaches the end).

Since the size distribution of the double-stranded fragments is a result of the ration of dTTP to dUTP or UTP used in the MDA reaction, rather than by the duration or degree of enzymatic treatment, this CoRE fragmentation method produces high degrees of fragmentation reproducibility, resulting in a population of double-stranded nucleic acid fragments that are all of a similar size.

Fragment End Repair and Modification.

In certain embodiments, after fragmenting, target nucleic acids are further modified to prepare them for insertion of multiple adaptors according to methods of the invention.

After physical fragmentation, target nucleic acids frequently have a combination of blunt and overhang ends as well as combinations of phosphate and hydroxyl chemistries at the termini. In this embodiment, the target nucleic acids are treated with several enzymes to create blunt ends with particular chemistries. In one embodiment, a polymerase and dNTPs is used to fill in any 5' single strands of an overhang to create a blunt end. Polymerase with 3' exonuclease activity (generally but not always the same enzyme as the 5' active one, such as T4 polymerase) is used to remove 3' overhangs. Suitable polymerases include, but are not limited to, T4 polymerase, Taq polymerases, E. coli DNA Polymerase 1, Klenow fragment, reverse transcriptases, phi29 related polymerases including wild type phi29 polymerase and derivatives of such polymerases, T7 DNA Polymerase, T5 DNA Polymerase, RNA polymerases. These techniques can be used to generate blunt ends, which are useful in a variety of applications.

In further optional embodiments, the chemistry at the termini is altered to avoid target nucleic acids from ligating to each other. For example, in addition to a polymerase, a protein kinase can also be used in the process of creating blunt ends by utilizing its 3' phosphatase activity to convert 3' phosphate groups to hydroxyl groups. Such kinases can include without limitation commercially available kinases such as T4 kinase, as well as kinases that are not commercially available but have the desired activity.

Similarly, a phosphatase can be used to convert terminal phosphate groups to hydroxyl groups. Suitable phosphatases include, but are not limited to, alkaline phosphatase (including calf intestinal phosphatase), antarctic phosphatase, apyrase, pyrophosphatase, inorganic (yeast) thermostable inorganic pyrophosphatase, and the like, which are known in the art.

These modifications prevent the target nucleic acids from ligating to each other in later steps of methods of the invention, thus ensuring that during steps in which adaptors (and/or adaptor arms) are ligated to the termini of target nucleic acids, target nucleic acids will ligate to adaptors but not to other target nucleic acids. Target nucleic acids can be ligated to adaptors in a desired orientation. Modifying the ends avoids the undesired configurations in which the target nucleic acids ligate to each other and/or the adaptors ligate to each other. The orientation of each adaptor-target nucleic acid ligation can also be controlled through control of the chemistry of the termini of both the adaptors and the target nucleic acids. Such modifications can prevent the creation of nucleic acid templates containing different fragments ligated in an unknown conformation, thus reducing and/or removing the errors in sequence identification and assembly that can result from such undesired templates.

The DNA may be denatured after fragmentation to produce single-stranded fragments.

Amplification.

In one embodiment, after fragmenting, (and in fact before or after any step outlined herein) an amplification step can be applied to the population of fragmented nucleic acids to ensure that a large enough concentration of all the fragments is available for subsequent steps. According to one embodiment of the invention, methods are provided for sequencing small quantities of complex nucleic acids, including those of higher organisms, in which such complex nucleic acids are amplified in order to produce sufficient nucleic acids for sequencing by the methods described herein. Sequencing methods described herein provide highly accurate sequences at a high call rate even with a fraction of a genome equivalent as the starting material with sufficient amplification. Note that a cell includes approximately 6.6 picograms (pg) of genomic DNA. Whole genomes or other complex nucleic acids from single cells or a small number of cells of an organism, including higher organisms such as humans, can be performed by the methods of the present invention. Sequencing of complex nucleic acids of a higher organism can be accomplished using 1 pg, 5 pg, 10 pg, 30 pg, 50 pg, 100 pg, or 1 ng of a complex nucleic acid as the starting material, which is amplified by any nucleic acid amplification method known in the art, to produce, for example, 200 ng, 400 ng, 600 ng, 800 ng, 1 pg, 2 pg, 3 pg, 4 pg, pg, 10 pg or greater quantities of the complex nucleic acid. We also disclose nucleic acid amplification protocols that minimize GC bias. However, the need for amplification and subsequent GC bias can be reduced further simply by isolating one cell or a small number of cells, culturing them for a sufficient time under suitable culture conditions known in the art, and using progeny of the starting cell or cells for sequencing.

Such amplification methods include without limitation: multiple displacement amplification (MDA), polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA) (for circularized fragments), and invasive cleavage technology.

Amplification can be performed after fragmenting or before or after any step outlined herein.

MDA Amplification Protocol with Reduced GC Bias.

In one aspect, the present invention provides methods of sample of preparation in which ~10 Mb of DNA per aliquot is faithfully amplified, e.g., approximately 30.000-fold depending on the amount of starting DNA, prior to library construction and sequencing.

According to one embodiment of LFR methods of the present invention, LFR begins with treatment of genomic nucleic acids, usually genomic DNA, with a 5' exonuclease to create 3' single-stranded overhangs. Such single stranded overhangs serve as MDA initiation sites. Use of the exonuclease also eliminates the need for a heat or alkaline denaturation step prior to amplification without introducing bias into the population of fragments. In another embodiment, alkaline denaturation is combined with the 5' exonuclease treatment, which results in a reduction in bias that is greater than what is seen with either treatment alone. DNA treated with 5' exonuclease and optionally with alkaline denaturation is then diluted to sub-genome concentrations and dispersed across a number of aliquots, as discussed above. After separation into aliquots, e.g., across multiple wells, the fragments in each aliquot are amplified.

In one embodiment, a phi29-based multiple displacement amplification (MDA) is used. Numerous studies have examined the range of unwanted amplification biases, background product formation, and chimeric artifacts introduced via phi29 based MDA, but many of these short comings have occurred under extreme conditions of amplification (greater than 1 million fold). Commonly, LFR employs a substantially lower level of amplification and starts with long DNA fragments (e.g., ~100 kb), resulting in efficient MDA and a more acceptable level of amplification biases and other amplification-related problems.

We have developed an improved MDA protocol to overcome problems associated with MDA that uses various additives (e.g., DNA modifying enzymes, sugars, and/or chemicals like DMSO), and/or different components of the reaction conditions for MDA are reduced, increased or substituted to further improve the protocol. To minimize chimeras, reagents can also be included to reduce the availability of the displaced single stranded DNA from acting as an incorrect template for the extending DNA strand, which is a common mechanism for chimera formation. A major source of coverage bias introduced by MDA is caused by differences in amplification between GC-rich verses AT-rich regions. This can be corrected by using different reagents in the MDA reaction and/or by adjusting the primer concentration to create an environment for even priming across all % GC regions of the genome. In some embodiments, random hexamers are used in priming MDA. In other embodiments, other primer designs are utilized to reduce bias. In further embodiments, use of 5' exonuclease before or during MDA can help initiate low-bias successful priming, particularly with longer (i.e., 200 kb to 1 Mb) fragments that are useful for sequencing regions characterized by long segmental duplication (i.e., in some cancer cells) and complex repeats.

In some embodiments, improved, more efficient fragmentation and ligation steps are used that reduce the number of rounds of MDA amplification required for preparing samples by as much as 10,000 fold, which further reduces bias and chimera formation resulting from MDA.

In some embodiments, the MDA reaction is designed to introduce uracils into the amplification products in preparation for CoRE fragmentation. In some embodiments, a standard MDA reaction utilizing random hexamers is used to amplify the fragments in each well; alternatively, random 8-mer primers can be used to reduce amplification bias (e.g., GC-bias) in the population of fragments. In further embodiments, several different enzymes can also be added to the MDA reaction to reduce the bias of the amplification. For example, low concentrations of non-processive 5' exonucleases and/or single-stranded binding proteins can be used to create binding sites for the 8-mers. Chemical agents such as betaine, DMSO, and trehalose can also be used to reduce bias.

After amplification of the fragments in each aliquot, the amplification products may optionally be subjected to another round of fragmentation. In some embodiments the CoRE method is used to further fragment the fragments in each aliquot following amplification. In such embodiments, MDA amplification of fragments in each aliquot is designed to incorporate uracils into the MDA products. Each aliquot containing MDA products is treated with a mix of Uracil DNA glycosylase (UDG), DNA glycosylase-lyase Endonuclease VIII, and T4 polynucleotide kinase to excise the uracil bases and create single base gaps with functional 5' phosphate and 3' hydroxyl groups. Nick translation through use of a polymerase such as Taq polymerase results in double-stranded blunt-end breaks, resulting in ligatable fragments of a size range dependent on the concentration of dUTP added in the MDA reaction. In some embodiments, the CoRE method used involves removing uracils by polymerization and strand displacement by phi29. The fragmenting of the MDA products can also be achieved via sonication or enzymatic treatment. Enzymatic treatment that could be used in this embodiment includes without limitation DNase I, T7 endonuclease I, micrococcal nuclease, and the like.

Following fragmentation of the MDA products, the ends of the resultant fragments may be repaired. Many fragmentation techniques can result in termini with overhanging ends and termini with functional groups that are not useful in later ligation reactions, such as 3' and 5' hydroxyl groups and/or 3' and 5' phosphate groups. It may be useful to have fragments that are repaired to have blunt ends. It may also be desirable to modify the termini to add or remove phosphate and hydroxyl groups to prevent "polymerization" of the target sequences. For example, a phosphatase can be used to eliminate phosphate groups, such that all ends contain hydroxyl groups. Each end can then be selectively altered to allow ligation between the desired components. One end of the fragments can then be "activated" by treatment with alkaline phosphatase. The fragments then can be tagged with an adaptor to identify fragments that come from the same aliquot in the LFR method.

Tagging Fragments in Each Aliquot.

After amplification, the DNA in each aliquot is tagged so as to identify the aliquot in which each fragment originated. In further embodiments the amplified DNA in each aliquot is further fragmented before being tagged with an adaptor such that fragments from the same aliquot will all comprise the same tag; see for example US 2007/0072208, hereby incorporated by reference.

According to one embodiment, the adaptor is designed in two segments—one segment is common to all wells and blunt end ligates directly to the fragments using methods described further herein. The "common" adaptor is added as two adaptor arms—one arm is blunt end ligated to the 5' end of the fragment and the other arm is blunt end ligated to the 3' end of the fragment. The second segment of the tagging adaptor is a "barcode" segment that is unique to each well. This barcode is generally a unique sequence of nucleotides, and each fragment in a particular well is given the same barcode. Thus, when the tagged fragments from all the wells are re-combined for sequencing applications, fragments from the same well can be identified through identification of the barcode adaptor. The barcode is ligated to the 5' end of the common adaptor arm. The common adaptor and the barcode adaptor can be ligated to the fragment sequentially or simultaneously. As will be described in further detail herein, the ends of the common adaptor and the barcode adaptor can be modified such that each adaptor segment will ligate in the correct orientation and to the proper molecule. Such modifications prevent "polymerization" of the adaptor segments or the fragments by ensuring that the fragments are unable to ligate to each other and that the adaptor segments are only able to ligate in the illustrated orientation.

In further embodiments, a three segment design is utilized for the adaptors used to tag fragments in each well. This embodiment is similar to the barcode adaptor design described above, except that the barcode adaptor segment is split into two segments. This design allows for a wider range of possible barcodes by allowing combinatorial barcode adaptor segments to be generated by ligating different barcode segments together to form the full barcode segment. This combinatorial design provides a larger repertoire of possible barcode adaptors while reducing the number of full size barcode adaptors that need to be generated. In further embodiments, unique identification of each aliquot is achieved with 8-12 base pair error correcting barcodes. In some embodiments, the same number of adaptors as wells (384 and 1536 in the above-described non-limiting examples) is used. In further embodiments, the costs associated with generating adaptors is are reduced through a novel combinatorial tagging approach based on two sets of 40 half-barcode adapters.

In one embodiment, library construction involves using two different adaptors. A and B adapters are easily be modified to each contain a different half-barcode sequence to yield thousands of combinations. In a further embodiment, the barcode sequences are incorporated on the same adapter. This can be achieved by breaking the B adaptor into two parts, each with a half barcode sequence separated by a common overlapping sequence used for ligation. The two tag components have 4-6 bases each. An 8-base (2×4 bases) tag set is capable of uniquely tagging 65,000 aliquots. One extra base (2×5 bases) will allow error detection and 12 base tags (2×6 bases, 12 million unique barcode sequences) can be designed to allow substantial error detection and correction in 10,000 or more aliquots using Reed-Solomon design (U.S. patent application Ser. No. 12/697,995, published as US 2010/0199155, which is incorporated herein by reference). Both 2×5 base and 2×6 base tags may include use of degenerate bases (i.e., "wild-cards") to achieve optimal decoding efficiency.

After the fragments in each well are tagged, all of the fragments are combined or pooled to form a single population. These fragments can then be used to generate nucleic acid templates or library constructs for sequencing. The nucleic acid templates generated from these tagged fragments will be identifiable as belonging to a particular well by the barcode tag adaptors attached to each fragment.

Long Fragment Read (LFR) technology

Overview

Individual human genomes are diploid in nature, with half of the homologous chromosomes being derived from each parent. The context in which variations occur on each individual chromosome can have profound effects on the expression and regulation of genes and other transcribed regions of the genome. Further, determining if two potentially detrimental mutations occur within one or both alleles of a gene is of paramount clinical importance.

Current methods for whole-genome sequencing lack the ability to separately assemble parental chromosomes in a cost-effective way and describe the context (haplotypes) in which variations co-occur. Simulation experiments show that chromosome-level haplotyping requires allele linkage information across a range of at least 70-100 kb. This cannot be achieved with existing technologies that use amplified DNA, which are be limited to reads less than 1000 bases due to difficulties in uniform amplification of long DNA molecules and loss of linkage information in sequencing. Mate-pair technologies can provide an equivalent to the extended read length but are limited to less than 10 kb due to inefficiencies in making such DNA libraries (due to the difficulty of circularizing DNA longer than a few kb in length). This approach also needs extreme read coverage to link all heterozygotes.

Single molecule sequencing of greater than 100 kb DNA fragments would be useful for haplotyping if processing such long molecules were feasible, if the accuracy of single molecule sequencing were high, and detection/instrument costs were low. This is very difficult to achieve on short molecules with high yield, let alone on 100 kb fragments.

Most recent human genome sequencing has been performed on short read-length (<200 bp), highly parallelized systems starting with hundreds of nanograms of DNA. These technologies are excellent at generating large volumes of data quickly and economically. Unfortunately, short reads, often paired with small mate-gap sizes (500 bp-10 kb), eliminate most SNP phase information beyond a few kilobases (McKernan et al., Genome Res. 19:1527, 2009). Furthermore, it is very difficult to maintain long DNA fragments in multiple processing steps without fragmenting as a result of shearing.

At the present time three personal genomes, those of J. Craig Venter (Levy et al., PLoS Biol. 5:e254, 2007), a Gujarati Indian (HapMap sample NA20847; Kitzman et al., Nat. Biotechnol. 29:59, 2011), and two Europeans (Max Planck One [MP1]; Suk et al., Genome Res., 2011; genome.cshlp.org/content/early/2011/09/02/gr.125047.111.full.pdf; and HapMap Sample NA 12878; Duitama et al., Nucl. Acids Res. 40:2041-2053, 2012) have been sequenced and assembled as diploid. All have involved cloning long DNA fragments into constructs in a process similar to the bacterial artificial chromosome (BAC) sequencing used during construction of the human reference genome (Venter et al., Science 291:1304, 2001; Lander et al., Nature 409:860, 2001). While these processes generate long phased contigs (N50s of 350 kb [Levy et al., PLoS Biol. 5:e254, 2007], 386 kb [Kitzman et al., Nat. Biotechnol. 29:59-63, 2011] and 1 Mb [Suk et al., Genome Res. 21:1672-1685, 2011]) they require a large amount of initial DNA, extensive library processing, and are too expensive to use in a routine clinical environment.

Additionally, whole chromosome haplotyping has been demonstrated through direct isolation of metaphase chromosomes (Zhang et al., Nat. Genet. 38:382-387, 2006; Ma et al., Nat. Methods 7:299-301, 2010; Fan et al., Nat. Biotechnol. 29:51-57, 2011; Yang et al., Proc. Natl. Acad. Sci. USA 108:12-17, 2011). These methods are excellent for long-range haplotyping but have yet to be used for whole-genome sequencing and require preparation and isolation of whole metaphase chromosomes, which can be challenging for some clinical samples.

LFR methods overcome these limitations. LFR includes DNA preparation and tagging, along with related algorithms and software, to enable an accurate assembly of separate sequences of parental chromosomes (i.e., complete haplotyping) in diploid genomes at significantly reduced experimental and computational costs.

LFR is based on the physical separation of long fragments of genomic DNA (or other nucleic acids) across many different aliquots such that there is a low probability of any given region of the genome of both the maternal and paternal component being represented in the same aliquot. By placing a unique identifier in each aliquot and analyzing many aliquots in the aggregate, DNA sequence data can be assembled into a diploid genome, e.g., the sequence of each parental chromosome can be determined. LFR does not require cloning fragments of a complex nucleic acid into a vector, as in haplotyping approaches using large-fragment (e.g., BAC) libraries. Nor does LFR require direct isolation of individual chromosomes of an organism. Finally, LFR can be performed on an individual organism and does not require a population of the organism in order to accomplish haplotype phasing.

As used herein, the term "vector" means a plasmid or viral vector into which a fragment of foreign DNA is inserted. A vector is used to introduce foreign DNA into a suitable host cell, where the vector and inserted foreign DNA replicates due to the presence in the vector of, for example, a functional origin of replication or autonomously replicating sequence. As used herein, the term "cloning" refers to the insertion of a fragment of DNA into a vector and replication of the vector with inserted foreign DNA in a suitable host cell.

LFR can be used together with the sequencing methods discussed in detail herein and, more generally, as a preprocessing method with any sequencing technology known in the art, including both short-read and longer-read methods. LFR also can be used in conjunction with various types of analysis, including, for example, analysis of the transcriptome, methylome, etc. Because it requires very little input DNA, LFR can be used for sequencing and haplotyping one or a small number of cells, which can be particularly important for cancer, prenatal diagnostics, and personalized medicine. This can facilitate the identification of familial genetic disease, etc. By making it possible to distinguish calls from the two sets of chromosomes in a diploid sample, LFR also allows higher confidence calling of variant and non-variant positions at low coverage. Additional applications of LFR include resolution of extensive rearrangements in cancer genomes and full-length sequencing of alternatively spliced transcripts.

LFR can be used to process and analyze complex nucleic acids, including but not limited to genomic DNA, that is purified or unpurified, including cells and tissues that are gently disrupted to release such complex nucleic acids without shearing and overly fragmenting such complex nucleic acids.

In one aspect, LFR produces virtual read lengths of approximately 100-1000 kb in length.

In addition, LFR can also dramatically reduce the computational demands and associated costs of any short read technology. Importantly, LFR removes the need for extending sequencing read length if that reduces the overall yield. An additional benefit of LFR is a substantial (10- to 1000-fold) reduction in errors or questionable base calls that can result from current sequencing technologies, usually one per 100 kb, or 30,000 false positive calls per human genome, and a similar number of undetected variants per human genome. This dramatic reduction in errors minimizes the need for follow up confirmation of detected variants and facilitates adoption of human genome sequencing for diagnostic applications.

In addition to being applicable to all sequencing platforms, LFR-based sequencing can be applied to any application, including without limitation, the study of structural rearrangements in cancer genomes, full methylome analysis including the haplotypes of methylated sites, and de novo assembly applications for metagenomics or novel genome sequencing, even of complex polyploid genomes like those found in plants.

LFR provides the ability to obtain actual sequences of individual chromosomes as opposed to just the consensus sequences of parental or related chromosomes (in spite of their high similarities and presence of long repeats and segmental duplications). To generate this type of data, the continuity of sequence is in general established over long DNA ranges such as 100 kb to 1 Mb.

A further aspect of the invention includes software and algorithms for efficiently utilizing LFR data for whole chromosome haplotype and structural variation mapping and false positive/negative error correcting to fewer than 300 errors per human genome.

In a further aspect, LFR techniques of the invention reduce the complexity of DNA in each aliquot by 100-1000 fold depending on the number of aliquots and cells used. Complexity reduction and haplotype separation in >100 kb long DNA can be helpful in more efficiently and cost effectively (up to 100-fold reduction in cost) assembling and detect all variations in human and other diploid genomes.

LFR methods described herein can be used as a pre-processing step for sequencing diploid genomes using any sequencing methods known in the art. The LFR methods described herein may in further embodiments be used on any number of sequencing platforms, including for example without limitation, polymerase-based sequencing-by-synthesis (e.g., HiSeq 2500 system, Illumina, San Diego, Calif.), ligation-based sequencing (e.g., SOLiD 5500, Life Technologies Corporation, Carlsbad, Calif.), ion semiconductor sequencing (e.g., Ion PGM or Ion Proton sequencers, Life Technologies Corporation, Carlsbad, Calif.), zero-mode waveguides (e.g., PacBio RS sequencer, Pacific Biosciences, Menlo Park, Calif.), nanopore sequencing (e.g., Oxford Nanopore Technologies Ltd., Oxford, United Kingdom), pyrosequencing (e.g., 454 Life Sciences, Branford, Conn.), or other sequencing technologies. Some of these sequencing technologies are short-read technologies, but others produce longer reads, e.g., the GS FLX+ (454 Life Sciences; up to 1000 bp), PacBio RS (Pacific Biosciences; approximately 1000 bp) and nanopore sequencing (Oxford Nanopore Technologies Ltd.; 100 kb). For haplotype phasing, longer reads are advantageous, requiring much less computation, although they tend to have a higher error rate and errors in such long reads may need to be identified and corrected according to methods set forth herein before haplotype phasing.

According to one embodiment of the invention, the basic steps of LFR include: (1) separating long fragments of a complex nucleic acid (e.g., genomic DNA) into aliquots, each aliquot containing a fraction of a genome equivalent of DNA; (2) amplifying the genomic fragments in each aliquot; (3) fragmenting the amplified genomic fragments to create short fragments (e.g., ~500 bases in length in one embodiment) of a size suitable for library construction; (4) tagging the short fragments to permit the identification of the aliquot from which the short fragments originated; (5) pooling the tagged fragments; (6) sequencing the pooled, tagged fragments; and (7) analyzing the resulting sequence data to map and assemble the data and to obtain haplotype information. According to one embodiment, LFR uses a 384-well plate with 10-20% of a haploid genome in each well, yielding a theoretical 19-38× physical coverage of both the maternal and paternal alleles of each fragment. An initial DNA redundancy of 19-38× ensures complete genome coverage and higher variant calling and phasing accuracy. LFR avoids subcloning of fragments of a complex nucleic acid into a vector or the need to isolate individual chromosomes (e.g., metaphase chromosomes), and it can be fully automated, making it suitable for high-throughput, cost-effective applications.

We have also developed techniques for using LFR for error reduction and other purposes as detailed herein. LFR methods have been disclosed in U.S. patent application Ser. Nos. 12/816,365, 12/329,365, 12/266,385, and 12/265,593, and in U.S. Pat. Nos. 7,906,285, 7,901,891, and 7,709,197, all of which are hereby incorporated by reference in their entirety.

As used herein, the term "haplotype" means a combination of alleles at adjacent locations (loci) on the chromosome that are transmitted together or, alternatively, a set of sequence variants on a single chromosome of a chromosome pair that are statistically associated. Every human individual has two sets of chromosomes, one paternal and the other maternal. Usually DNA sequencing results only in genotypic information, the sequence of unordered alleles along a segment of DNA. Inferring the haplotypes for a genotype separates the alleles in each unordered pair into two separate sequences, each called a haplotype. Haplotype information is necessary for many different types of genetic analysis, including disease association studies and making inference on population ancestries.

As used herein, the term "phasing" (or resolution) means sorting sequence data into the two sets of parental chromosomes or haplotypes. Haplotype phasing refers to the problem of receiving as input a set of genotypes for some number of individuals, and outputting a pair of haplotypes for each individual, one being paternal and the other maternal. Phasing can involve resolving sequence data over a region of a genome, or as little as two sequence variants in a read or contig, which may be referred to as local phasing, or microphasing. It can also involve phasing of longer contigs, generally including greater than about ten sequence variants, or even a whole genome sequence, which may be referred to as "universal phasing." Optionally, phasing sequence variants takes place during genome assembly.

Aliquoting Fractions of a Genome Equivalent of the Complex Nucleic Acid

The LFR process is based upon the stochastic physical separation of a genome in long fragments into many aliquots such that each aliquot contains a fraction of a haploid genome. As the fraction of the genome in each pool decreases, the statistical likelihood of having a corresponding fragment from both parental chromosomes in the same pool dramatically diminishes.

In some embodiments, a 10% genome equivalent is aliquoted into each well of a multiwell plate. In other embodiments, 1% to 50% of a genome equivalent of the complex nucleic acid is aliquoted into each well. As noted above, the number of aliquots and genome equivalents can depend on the number of aliquots, original fragment size, or other factors. Optionally, a double-stranded nucleic acid (e.g., a human genome) is denatured before aliquoting; thus single-stranded complements may be apportioned to different aliquots. According to one embodiment, each aliquot comprises 2, 4, 6 or more copies (or complements) of a majority of strands of the complex nucleic acid (or 2, 4, 6 or more complements, if a double-stranded nucleic acid is denatured before aliquoting).

For example, at 0.1 genome equivalents per aliquot (approximately 0.66 picogram, or pg, of DNA, at approximately 6.6 pg per human genome) there is a 10% chance that two fragments will overlap and a 50% chance those fragments will be derived from separate parental chromosomes; this yields a 95% of the base pairs in an aliquot are non-overlapping, i.e., 5% overall chance that a particular aliquot will be uninformative for a given fragment, because the aliquot contains fragments deriving from both maternal and paternal chromosomes. Aliquots that are uninformative can be identified because the sequence data resulting from such aliquots contains an increased amount of "noise," that is, the impurity in the connectivity matrix between pairs of hets. Fuzzy interference system (FIS) allows robustness against a certain degree of impurity, i.e., it can make correct connection despite the impurity (up to a certain degree). Even smaller amounts of genomic DNA can be used, particularly in the context of micro- or nanodroplets or emulsions, where each droplet could include one DNA fragment (e.g., a single 50 kb fragment of genomic DNA or approximately $1.5 \times 10^{-5}$ genome equivalents). Even at 50 percent of a genome equivalent, a majority of aliquots would be informative. At higher levels, e.g., 70 percent of a genome equivalent, wells that are informative can be identified and used. According to one aspect of the invention, 0.000015, 0.0001, 0.001, 0.01, 0.1, 1, 5, 10, 15, 20, 25, 40, 50, 60, or 70 percent of a genome equivalent of the complex nucleic acid is present in each aliquot.

It should be appreciated that the dilution factor can depend on the original size of the fragments. That is, using gentle techniques to isolate genomic DNA, fragments of roughly 100 kb can be obtained, which are then aliquoted. Techniques that allow larger fragments result in a need for fewer aliquots, and those that result in shorter fragments may require more dilution.

We have successfully performed all six enzymatic steps in the same reaction without DNA purification, which facilitates miniaturization and automation and makes it feasible to adapt LFR to a wide variety of platforms and sample preparation methods.

According to one embodiment, each aliquot is contained in a separate well of a multi-well plate (for example, a 384 well plate). However, any appropriate type of container or system known in the art can be used to hold the aliquots, or the LFR process can be performed using microdroplets or emulsions, as described herein. According to one embodiment of the invention, volumes are reduced to sub-microliter levels. In one embodiment, automated pipetting approaches can be used in 1536 well formats.

In general, as the number of aliquots increases, for instance to 1536, and the percent of the genome decreases down to approximately 1% of a haploid genome, the statistical support for haplotypes increases dramatically, because the sporadic presence of both maternal and paternal haplotypes in the same well diminishes. Consequently, a large number of small aliquots with a negligent frequency of mixed haplotypes per aliquot allows for the use of fewer cells. Similarly, longer fragments (e.g., 300 kb or longer) help bridge over segments lacking heterozygous loci.

Nanoliter (nl) dispensing tools (e.g., Hamilton Robotics Nano Pipetting head, TTP LabTech Mosquito, and others) that provide noncontact pipeting of 50-100 nl can be used for fast and low cost pipetting to make tens of genome libraries in parallel. The increase in the number of aliquots (as compared with a 384 well plate) results in a large reduction in the complexity of the genome within each well, reducing the overall cost of computing over 10-fold and increasing data quality. Additionally, the automation of this process increases the throughput and lowers the hands-on cost of producing libraries.

LFR Using Smaller Aliquot Volumes, Including Microdroplets and Emulsions

Even further cost reductions and other advantages can be achieved using microdroplets. In some embodiments, LFR is performed with combinatorial tagging in emulsion or microfluidic devices. A reduction of volumes down to picoliter levels in 10,000 aliquots can achieve an even greater cost reduction due to lower reagent and computational costs.

In one embodiment, LFR uses 10 microliter (µl) volume of reagents per well in a 384 well format. Such volumes can be reduced to by using commercially available automated pipetting approaches in 1536 well formats, for example. Further volume reductions can be achieved using nanoliter (nl) dispensing tools (e.g., Hamilton Robotics Nano Pipetting head, TTP LabTech Mosquito, and others) that provide noncontact pipeting of 50-100 nl can be used for fast and low cost pipetting to make tens of genome libraries in parallel. Increasing the number of aliquots results in a large reduction in the complexity of the genome within each well, reducing the overall cost of computing and increasing data quality. Additionally, the automation of this process increases the throughput and lower the cost of producing libraries.

In further embodiments, unique identification of each aliquot is achieved with 8-12 base pair error correcting barcodes. In some embodiments, the same number of adaptors as wells is used.

In further embodiments, a novel combinatorial tagging approach is used based on two sets of 40 half-barcode adapters. In one embodiment, library construction involves using two different adaptors. A and B adapters are easily be modified to each contain a different half-barcode sequence to yield thousands of combinations. In a further embodiment, the barcode sequences are incorporated on the same adapter. This can be achieved by breaking the B adaptor into two parts, each with a half barcode sequence separated by a common overlapping sequence used for ligation. The two tag components have 4-6 bases each. An 8-base (2×4 bases) tag set is capable of uniquely tagging 65,000 aliquots. One extra base (2×5 bases) will allow error detection and 12 base tags (2×6 bases, 12 million unique barcode sequences) can be designed to allow substantial error detection and correction in 10,000 or more aliquots using Reed-Solomon design. In exemplary embodiments, both 2×5 base and 2×6 base tags, including use of degenerate bases (i.e., "wild-cards"), are employed to achieve optimal decoding efficiency.

A reduction of volumes down to picoliter levels (e.g., in 10,000 aliquots) can achieve an even greater reduction in reagent and computational costs. In some embodiments, this level of cost reduction and extensive aliquoting is accomplished through the combination of the LFR process with combinatorial tagging to emulsion or microfluidic-type devices. The ability to perform all enzymatic steps in the same reaction without DNA purification facilitates the ability to miniaturize and automate this process and results in adaptability to a wide variety of platforms and sample preparation methods.

In one embodiment, LFR methods are used in conjunction with an emulsion-type device. A first step to adapting LFR to an emulsion type device is to prepare an emulsion reagent of combinatorial barcode tagged adapters with a single unique barcode per droplet. Two sets of 100 half-barcodes is sufficient to uniquely identify 10,000 aliquots. However, increasing the number of half-barcode adapters to over 300 can allow for a random addition of barcode droplets to be combined with the sample DNA with a low likelihood of any two aliquots containing the same combination of barcodes. Combinatorial barcode adapter droplets can be made and stored in a single tube as a reagent for thousands of LFR libraries.

In one embodiment, the present invention is scaled from 10,000 to 100,000 or more aliquot libraries. In a further embodiment, the LFR method is adapted for such a scale-up by increasing the number of initial half barcode adapters. These combinatorial adapter droplets are then fused one-to-one with droplets containing ligation ready DNA representing less than 1% of the haploid genome. Using a conservative estimate of 1 nl per droplet and 10,000 drops this represents a total volume of 10 µl for an entire LFR library.

Recent studies have also suggested an improvement in GC bias after amplification (e.g., by MDA) and a reduction in background amplification by decreasing the reaction volumes down to nanoliter size.

There are currently several types of microfluidics devices (e.g., devices sold by Advanced Liquid Logic, Morrisville, N.C.) or pico/nano-droplet (e.g., RainDance Technologies, Lexington, Mass.) that have pico-/nano-drop making, fusing (3000/second) and collecting functions and could be used in such embodiments of LFR. In other embodiments, ~10-20 nanoliter drops are deposited in plates or on glass slides in 3072-6144 format (still a cost effective total MDA volume of 60 µl without losing the computational cost savings or the ability to sequence genomic DNA from a small number of cells) or higher using improved nano-pipeting or acoustic droplet ejection technology (e.g., LabCyte Inc., Sunnyvale, Calif.) or using microfluidic devices (e.g., those produced by Fluidigm, South San Francisco, Calif.) that are capable of handling up to 9216 individual reaction wells. Increasing the number of aliquots results in a large reduction in the complexity of the genome within each well, reducing the overall cost of computing and increasing data quality. Additionally, the automation of this process increases the throughput and lower the cost of producing libraries.

Amplifying

According to one embodiment, the LFR process begins with a short treatment of genomic DNA with a 5' exonuclease to create 3' single-stranded overhangs that serve as MDA initiation sites. The use of the exonuclease eliminates the need for a heat or alkaline denaturation step prior to amplification without introducing bias into the population of fragments. Alkaline denaturation can be combined with the 5' exonuclease treatment, which results in a further reduction in bias. The DNA is then diluted to sub-genome concentrations and aliquoted. After aliquoting the fragments in each well are amplified, e.g., using an MDA method. In certain embodiments, the MDA reaction is a modified phi29 polymerase-based amplification reaction, although another known amplification method can be used.

In some embodiments, the MDA reaction is designed to introduce uracils into the amplification products. In some embodiments, a standard MDA reaction utilizing random hexamers is used to amplify the fragments in each well. In many embodiments, rather than the random hexamers, random 8-mer primers are used to reduce amplification bias in the population of fragments. In further embodiments, several different enzymes can also be added to the MDA reaction to reduce the bias of the amplification. For example, low concentrations of non-processive 5' exonucleases and/or single-stranded binding proteins can be used to create binding sites for the 8-mers. Chemical agents such as betaine, DMSO, and trehalose can also be used to reduce bias through similar mechanisms.

Fragmentation

According to one embodiment, after amplification of DNA in each well, the amplification products are subjected to a round of fragmentation. In some embodiments the above-described CoRE method is used to further fragment the fragments in each well following amplification. In order to use the CoRE method, the MDA reaction used to amplify the fragments in each well is designed to incorporate uracils into the MDA products. The fragmenting of the MDA products can also be achieved via sonication or enzymatic treatment.

If a CoRE method is used to fragment the MDA products, each well containing amplified DNA is treated with a mix of uracil DNA glycosylase (UDG), DNA glycosylase-lyase endonuclease VIII, and T4 polynucleotide kinase to excise the uracil bases and create single base gaps with functional 5' phosphate and 3' hydroxyl groups. Nick translation through use of a polymerase such as Taq polymerase results in double-stranded blunt end breaks, resulting in ligatable fragments of a size range dependent on the concentration of dUTP added in the MDA reaction. In some embodiments, the CoRE method used involves removing uracils by polymerization and strand displacement by phi29.

Following fragmentation of the MDA products, the ends of the resultant fragments can be repaired. Such repairs can be necessary, because many fragmentation techniques can result in termini with overhanging ends and termini with functional groups that are not useful in later ligation reactions, such as 3' and 5' hydroxyl groups and/or 3' and 5' phosphate groups. In many aspects of the present invention, it is useful to have fragments that are repaired to have blunt ends, and in some cases, it can be desirable to alter the chemistry of the termini such that the correct orientation of phosphate and hydroxyl groups is not present, thus preventing "polymerization" of the target sequences. The control over the chemistry of the termini can be provided using methods known in the art. For example, in some circumstances, the use of phosphatase eliminates all the phosphate groups, such that all ends contain hydroxyl groups. Each end can then be selectively altered to allow ligation between the desired components. One end of the fragments can then be "activated", in some embodiments by treatment with alkaline phosphatase.

After fragmentation and, optionally, end repair, the fragments are tagged with an adaptor.

Tagging

Generally, the tag adaptor arm is designed in two segments—one segment is common to all wells and blunt end ligates directly to the fragments using methods described further herein. The second segment is unique to each well and contains a "barcode" sequence such that when the contents of each well are combined, the fragments from each well can be identified.

According to one embodiment the "common" adaptor is added as two adaptor arms—one arm is blunt end ligated to the 5' end of the fragment and the other arm is blunt end ligated to the 3' end of the fragment. The second segment of the tagging adaptor is a "barcode" segment that is unique to each well. This barcode is generally a unique sequence of nucleotides, and each fragment in a particular well is given the same barcode. Thus, when the tagged fragments from all the wells are re-combined for sequencing applications, fragments from the same well can be identified through identification of the barcode adaptor. The barcode is ligated to the 5' end of the common adaptor arm. The common adaptor and the barcode adaptor can be ligated to the fragment sequentially or simultaneously. The ends of the common adaptor and the barcode adaptor can be modified such that each adaptor segment will ligate in the correct orientation and to the proper molecule. Such modifications prevent "polymerization" of the adaptor segments or the fragments by ensuring that the fragments are unable to ligate to each other and that the adaptor segments are only able to ligate in the illustrated orientation.

In further embodiments, a three-segment design is utilized for the adaptors used to tag fragments in each well. This embodiment is similar to the barcode adaptor design described above, except that the barcode adaptor segment is split into two segments. This design allows for a wider range of possible barcodes by allowing combinatorial barcode adaptor segments to be generated by ligating different barcode segments together to form the full barcode segment. This combinatorial design provides a larger repertoire of possible barcode adaptors while reducing the number of full size barcode adaptors that need to be generated.

According to one embodiment, after the fragments in each well are tagged, all of the fragments are combined to form a single population. These fragments can then be used to generate nucleic acid templates of the invention for sequencing. The nucleic acid templates generated from these tagged fragments are identifiable as originating from a particular well by the barcode tag adaptors attached to each fragment. Similarly, upon sequencing of the tag, the genomic sequence to which it is attached is also identifiable as originating from the well.

In some embodiments, LFR methods described herein do not include multiple levels or tiers of fragmentation/aliquoting, as described in U.S. patent application Ser. No. 11/451,692, filed Jun. 13, 2006, which is herein incorporated by reference in its entirety for all purposes. That is, some embodiments utilize only a single round of aliquoting, and also allow the repooling of aliquots for a single array, rather than using separate arrays for each aliquot.

LFR Using One or a Small Number of Cells as the Source of Complex Nucleic Acids

According to one embodiment, an LFR method is used to analyze the genome of an individual cell or a small number of cells. The process for isolating DNA in this case is similar to the methods described above, but may occur in a smaller volume.

As discussed above, isolating long fragments of genomic nucleic acid from a cell can be accomplished by a number of different methods. In one embodiment, cells are lysed and the intact nucleic are pelleted with a gentle centrifugation step. The genomic DNA is then released through proteinase K and RNase digestion for several hours. The material can then in some embodiments be treated to lower the concentration of remaining cellular waste—such treatments are well known in the art and can include without limitation dialysis for a period of time (e.g., from 2-16 hours) and/or dilution. Since such methods of isolating the nucleic acid does not involve many disruptive processes (such as ethanol precipitation, centrifugation, and vortexing), the genomic nucleic acid remains largely intact, yielding a majority of fragments that have lengths in excess of 150 kilobases. In some embodiments, the fragments are from about 100 to about 750 kilobases in lengths. In further embodiments, the fragments are from about 150 to about 600, about 200 to about 500, about 250 to about 400, and about 300 to about 350 kilobases in length.

Once the DNA is isolated and before it is aliquoted into individual wells, the genomic DNA must be carefully fragmented to avoid loss of material, particularly to avoid loss of sequence from the ends of each fragment, since loss of such material will result in gaps in the final genome assembly. In some cases, sequence loss is avoided through use of an infrequent nicking enzyme, which creates starting sites for a polymerase, such as phi29 polymerase, at distances of approximately 100 kb from each other. As the polymerase creates the new DNA strand, it displaces the old strand, with the end result being that there are overlapping sequences near the sites of polymerase initiation, resulting in very few deletions of sequence.

In some embodiments, a controlled use of a 5' exonuclease (either before or during the MDA reaction) can promote multiple replications of the original DNA from the single cell and thus minimize propagation of early errors through copying of copies.

In one aspect, methods of the present invention produce quality genomic data from single cells. Assuming no loss of DNA, there is a benefit to starting with a low number of cells (10 or less) instead of using an equivalent amount of DNA from a large prep. Starting with less than 10 cells and faithfully aliquoting substantially all DNA ensures uniform coverage in long fragments of any given region of the genome. Starting with five or fewer cells allows four times or greater coverage per each 100 kb DNA fragment in each aliquot without increasing the total number of reads above 120 Gb (20 times coverage of a 6 Gb diploid genome). However, a large number of aliquots (10,000 or more) and longer DNA fragments (>200 kb) are even more important for sequencing from a few cells, because for any given sequence there are only as many overlapping fragments as the number of starting cells and the occurrence of overlapping fragments from both parental chromosomes in an aliquot can be a devastating loss of information.

LFR is well suited to this problem, as it produces excellent results starting with only about 10 cells worth of starting input genomic DNA, and even one single cell would provide enough DNA to perform LFR. The first step in LFR is generally low bias whole genome amplification, which can be of particular use in single cell genomic analysis. Due to DNA strand breaks and DNA losses in handling, even single molecule sequencing methods would likely require some level of DNA amplification from the single cell. The difficulty in sequencing single cells comes from attempting to amplify the entire genome. Studies performed on bacteria using MDA have suffered from loss of approximately half of the genome in the final assembled sequence with a fairly high amount of variation in coverage across those sequenced regions. This can partially be explained as a result of the initial genomic DNA having nicks and strand breaks which cannot be replicated at the ends and are thus lost during the MDA process. LFR provides a solution to this problem through the creation of long overlapping fragments of the genome prior to MDA. According to one embodiment of the invention, in order to achieve this, a gentle process is used to isolate genomic DNA from the cell. The largely intact genomic DNA is then be lightly treated with a frequent nickase, resulting in a semi-randomly nicked genome. The strand-displacing ability of phi29 is then used to polymerize from the nicks creating very long (>200 kb) overlapping fragments. These fragments are then be used as starting template for LFR.

Methylation Analysis Using LFR

In a further aspect, methods and compositions of the present invention are used for genomic methylation analysis. There are several methods currently available for global genomic methylation analysis. One method involves bisulfate treatment of genomic DNA and sequencing of repetitive elements or a fraction of the genome obtained by methylation-specific restriction enzyme fragmenting. This technique yields information on total methylation, but provides no locus-specific data. The next higher level of resolution uses DNA arrays and is limited by the number of features on the chip. Finally, the highest resolution and the most expensive approach requires bisulfate treatment followed by sequencing of the entire genome. Using LFR it is possible to sequence all bases of the genome and assemble a complete diploid genome with digital information on levels of methylation for every cytosine position in the human genome (i.e., 5-base sequencing). Further, LFR allow blocks of methylated sequence of 100 kb or greater to be linked to sequence haplotypes, providing methylation haplotyping, information that is impossible to achieve with any currently available method.

In one non-limiting exemplary embodiment, methylation status is obtained in a method in which genomic DNA is first aliquoted and denatured for MDA. Next the DNA is treated with bisulfite (a step that requires denatured DNA). The remaining preparation follows those methods described for example in U.S. application Ser. No. 11/451,692, filed on Jun. 13, 2006 and Ser. No. 12/335,168, filed on Dec. 15, 2008, each of which is hereby incorporated by reference in its entirety for all purposes and in particular for all teachings related to nucleic acid analysis of mixtures of fragments according to long fragment read techniques.

In one aspect, MDA will amplify each strand of a specific fragment independently yielding for any given cytosine position 50% of the reads as unaffected by bisulfite (i.e., the base opposite of cytosine, a guanine is unaffected by bisulfate) and 50% providing methylation status. Reduced DNA complexity per aliquot helps with accurate mapping and assembly of the less informative, mostly 3-base (A, T, G) reads.

Bisulfite treatment has been reported to fragment DNA. However, careful titration of denaturation and bisulfate buffers can avoid excessive fragmenting of genomic DNA. A 50% conversion of cytosine to uracil can be tolerated in LFR allowing a reduction in exposure of the DNA to bisulfite to minimize fragmenting. In some embodiments, some degree of fragmenting after aliquoting is acceptable as it would not affect haplotyping.

Using LFR for Analysis of Cancer Genomes

It has been suggested that more than 90% of cancers harbor significant losses or gains in regions of the human genome, termed aneuploidy, with some individual cancers having been observed to contain in excess of four copies of some chromosomes. This increased complexity in copy number of chromosomes and regions within chromosomes makes sequencing cancer genomes substantially more difficult. The ability of LFR techniques to sequence and assemble very long (>100 kb) fragments of the genome makes it well suited for the sequencing of complete cancer genomes.

Error-Reduction by Sequencing a Target Nucleic Acid in Multiple Aliquots

According to one embodiment, even if LFR-based phasing is not performed and a standard sequencing approach is used, a target nucleic acid is divided into multiple aliquots, each containing an amount of the target nucleic acid. In each aliquot, the target nucleic acid is fragmented (if fragmentation is needed), and the fragments are tagged with an aliquot-specific tag (or an aliquot-specific set of tags) before amplification. Alternatively, when dealing with a tissue sample, one or more cells can be distributed to each of a number of aliquots before cell disruption, fragmentation, tagging fragments with an aliquot-specific tag, and amplification. In either case, amplified DNA from each aliquot may be sequenced separately or pooled and sequenced after pooling. An advantage of this approach is that errors introduced as a result of amplification (or other steps occurring in each aliquot) can be identified and corrected. For example, a base call (e.g., identifying a particular base such as A, C, G, or T) at a particular position (e.g., with respect to a reference) of the sequence data can be accepted as true if the base call is present in sequence data from two or more aliquots (or other threshold number), or in a substantial majority of expected aliquots (e.g. in at least 51, 70, or 80 percent), where the denominator can be restricted to the aliquots having a base call at the particular position. A base call can include changing one allele of a het or potential het. A base call at the particular position can be accepted as false if it is present in only one aliquot (or other threshold number of aliquots), or in a substantial minority of aliquots (e.g., less than 10, 5, or 3 aliquots or as measure with a relative number, such as 20 or 10 percent). The threshold values can be predetermined or dynamically determined based on the sequencing data. A base call at the particular position may be converted/accepted as "no call" if it is not present in a substantial minority and in a substantial majority of expected aliquots (e.g., in 40-60 percent). In some embodiments and implementations, various parameters may be used (e.g., in distribution, probability, and/or other functions or statistics) to characterize what may be considered a substantial minority or a substantial majority of aliquots. Examples of such parameters include, without limitation, one or more of: number of base calls identifying a particular base; coverage or total number of called bases at a particular position; number and/or identities of distinct aliquots that gave rise to sequence data that includes a particular base call; total number of distinct aliquots that gave rise to sequence data that includes at least one base call at a particular position; the reference base at the particular position; and others. In one embodiment, a combination of the above parameters for a particular base call can be input to a function to determine a score (e.g. a probability) for the particular base call. The scores can be compared to one or more threshold values as part of determining if a base call is accepted (e.g. above a threshold), in error (e.g. below a threshold), or a no call (e.g. if all of the scores for the base calls are below a threshold). The determination of a base call can be dependent on the scores of the other base calls.

As one basic example, if a base call of A is found in more than 35% (an example of a score) of the aliquots that contain a read for the position of interest and a base call of C is found in more than 35% of these aliquots and the other base calls each have a score of less than 20%, then the position can be considered a het composed of A and C, possibly subject to other criteria (e.g., a minimum number of aliquots containing a read at the position of interest). Thus, each of the scores can be input into another function (e.g. heuristics, which may use comparative or fuzzy logic) to provide the final determination of the base call(s) for the position.

As another example, a specific number of aliquots containing a base call may be used as a threshold. For instance, when analyzing a cancer sample, there may be low prevalence somatic mutations. In such a case, the base call may appear in less than 10% of the aliquots covering the position, but the base call may still be considered correct, possibly subject to other criteria. Thus, various embodiments can use absolute numbers or relative numbers, or both (e.g. as inputs into comparative or fuzzy logic). And, such numbers of aliquots can be input into a function (as mentioned above), as well as thresholds corresponding to each number, and the function can provide a score, which can also be compared to a one or more thresholds to make a final determination as to the base call at the particular position.

A further example of an error correction function relates to sequencing errors in raw reads leading to a putative variant call inconsistent with other variant calls and their haplotypes. If 20 reads of variant A are found in 9 and 8 aliquots belonging to respective haplotypes and 7 reads of variant G are found in 6 wells (5 or 6 of which are shared with aliquots with A-reads), the logic can reject variant G as a sequencing error because for the diploid genome only one variant can reside at a position in each haplotype. Variant A is supported with substantially more reads, and the G-reads substantially follow aliquots of A-reads indicating that they are most likely generate by wrongly reading G instead of A. If G reads are almost exclusively in separate aliquots from A, this can indicates that G-reads are wrongly mapped or they come from a contaminating DNA.

Identifying Expansions in Regions with Short Tandem Repeats

A short tandem repeat (STR) in DNA is a segment of DNA with a strong periodic pattern. STRs occur when a pattern of two or more nucleotides are repeated and the repeated sequences are directly adjacent to each other; the repeats may be perfect or imperfect, i.e., there may be a few base pairs that do not match the periodic motif. The pattern generally ranges in length from 2 to 5 base pairs (bp). STRs typically are located in non-coding regions, e.g., in introns. A short tandem repeat polymorphism (STRP) occurs when homologous STR loci differ in the number of repeats between individuals. STR analysis is often used for determining genetic profiles for forensic purposes. STRs occur- ring in the exons of genes may represent hypermutable regions that are linked to human disease (Madsen et al, BMC Genomics 9:410, 2008).

In human genomes (and genomes of other organisms) STRs include trinucleotide repeats, e.g., CTG or CAG repeats. Trinucleotide repeat expansion, also known as triplet repeat expansion, is caused by slippage during DNA replication, and is associated with certain diseases categorized as trinucleotide repeat disorders such as Huntington Disease. Generally, the larger the expansion, the more likely it is to cause disease or increase the severity of disease. This property results in the characteristic of "anticipation" seen in trinucleotide repeat disorders, that is, the tendency of age of onset of the disease to decrease and the severity of symptoms to increase through successive generations of an affected family due to the expansion of these repeats. Indentification of expansions in trinucleotide repeats may be useful for accurately predict age of onset and disease progression for trinucleotide repeat disorders.

Expansion of STRs such as trinucleotide repeats can be difficult to identify using next-generation sequencing methods. Such expansions may not map and may be missing or underrepresented in libraries. Using LFR, it is possible to see a significant drop in sequence coverage in an STR region. For example, a region with STRs will characteristically have a lower level of coverage as compared to regions without such repeats, and there will be a substantial drop in coverage in that region if there is an expansion of the region, observable in a plot of coverage versus position in the genome.

Figure 14:
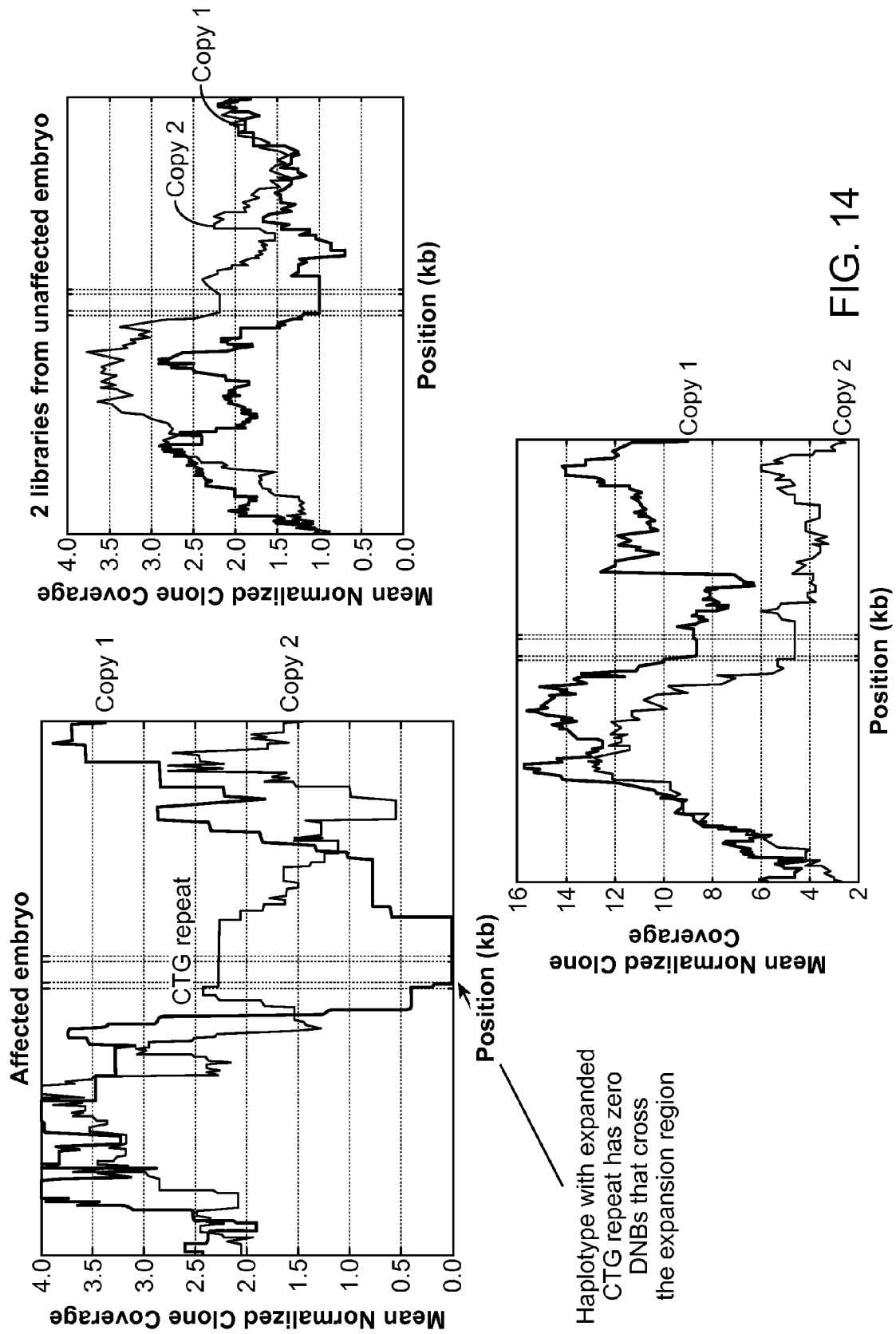
FIG. 14 shows detection of CTG repeat expansion in human embryos using haplotype-resolved clone coverage.

FIG. 14 shows an example of detection of CTG repeat expansion in an affected embryo. LFR was used to determine the parental haplotypes for the embryo. In a plot of mean normalized clone coverage versus position, the haplotype with an expanded CTG repeat had no or very small number of DNBs that crossed the expansion region, leading to a dropoff of coverage in the region. A dropoff could also be detected in the combined sequence coverage of both haplotypes; however, the drop of one haplotype may be more difficult to identify. For example, if the sequence coverage is about 20 on average, the region with the expansion region will have a significant drop, e.g., to 10 if the affected haplotype has zero coverage in the expansion region. Thus, a 50% drop would occur. However, if the sequence coverage for the two haplotypes is compared, the coverage is 10 in the normal haplotype and 0 in the affected haplotype, which is a drop of 10 but an overall percentage drop of 100%. Or, one can analyze the relative amounts, which is 2:1 (normal vs. coverage in expansion region) for the combined sequence coverage, but is 10:0 (haplotype 1 vs. haplotype 2), which is infinity or zero (depending on how the ratio is formed), and thus a large distinction.

Diagnostic Use of Sequence Data

Sequence data generated using the methods of the present invention are useful for a wide variety of purposes. According to one embodiment, sequencing methods of the present invention are used to identify a sequence variation in a sequence of a complex nucleic acid, e.g., a whole genome sequence, that is informative regarding a characteristic or medical status of a patient or of an embryo or fetus, such as the sex of an embryo or fetus or the presence or prognosis of a disease having a genetic component, including, for example, cystic fibrosis, sickle cell anemia, Marfan syndrome, Huntington's disease, and hemochromatosis or various cancers, such as breast cancer, for example. According to another embodiment, the sequencing methods of the present invention are used to provide sequence information beginning with between one and 20 cells from a patient (including but not limited to a fetus or an embryo) and assessing a characteristic of the patient on the basis of the sequence.

Cancer Diagnostics

Whole genome sequencing is a valuable tool in assessing the genetic basis of disease. A number of diseases are known for which there is a genetic basis, e.g., cystic fibrosis, One application of whole genome sequencing is to understanding cancer. The most significant impact of next-generation sequencing on cancer genomics has been the ability to re-sequence, analyze and compare the matched tumor and normal genomes of a single patient as well as multiple patient samples of a given cancer type. Using whole genome sequencing the entire spectrum of sequence variations can be considered, including germline susceptibility loci, somatic single nucleotide polymorphisms (SNPs), small insertion and deletion (indel) mutations, copy number variations (CNVs) and structural variants (SVs).

In general, the cancer genome is comprised of the patient's germ line DNA, upon which somatic genomic alterations have been superimposed. Somatic mutations identified by sequencing can be classified either as "driver" or "passenger" mutations. So-called driver mutations are those that directly contribute to tumor progression by conferring a growth or survival advantage to the cell. Passenger mutations encompass neutral somatic mutations that have been acquired during errors in cell division, DNA replication, and repair; these mutations may be acquired while the cell is phenotypically normal, or following evidence of a neoplastic change.

Historically, attempts have been made to elucidate the molecular mechanism of cancer, and several "driver" mutations, or biomarkers, such as HER2/neu2, have been identified. Based on such genes, therapeutic regimens have been developed to specifically target tumors with known genetic alterations. The best defined example of this approach is the targeting of HER2/neu in breast cancer cells by trastuzumab (Herceptin). Cancers, however, are not simple monogenetic diseases, but are instead characterized by combinations of genetic alterations that can differ among individuals. Consequently, these additional perturbations to the genome may render some drug regimens ineffective for certain individuals.

Cancer cells for whole genome sequencing may be obtained from biopsies of whole tumors (including microbiopsies of a small number of cells), cancer cells isolated from the bloodstream or other body fluids of a patient, or any other source known in the art.

Pre-Implantation Genetic Diagnosis

One application of the methods of the present invention is for pre-implantation genetic diagnosis. About 2 to 3% of babies born have some type of major birth defect. The risk of some problems, due to abnormal separation of genetic material (chromosomes), increases with the mother's age. About 50% of the time these types of problems are due to Down Syndrome, which is a third copy of chromosome 21 (Trisomy 21). The other half result from other types of chromosomal anomalies, including trisomies, point mutations, structural variations, copy number variations, etc. Many of these chromosomal problems result in a severely affected baby or one which does not survive even to delivery.

In medicine and (clinical) genetics pre-implantation genetic diagnosis (PGD or PIGD) (also known as embryo screening) refers to procedures that are performed on embryos prior to implantation, sometimes even on oocytes prior to fertilization. PGD can permit parents to avoid selective pregnancy termination. The term pre-implantation genetic screening (PGS) is used to denote procedures that do not look for a specific disease but use PGD techniques to identify embryos at risk due, for example, to a genetic condition that could lead to disease. Procedures performed on sex cells before fertilization may instead be referred to as methods of oocyte selection or sperm selection, although the methods and aims partly overlap with PGD.

Preimplantation genetic profiling (PGP) is a method of assisted reproductive technology to perform selection of embryos that appear to have the greatest chances for successful pregnancy. When used for women of advanced maternal age and for patients with repetitive in vitro fertilization (IVF) failure, PGP is mainly carried out as a screening for detection of chromosomal abnormalities such as aneuploidy, reciprocal and Robertsonian translocations, and other abnormalities such as chromosomal inversions or deletions. In addition, PGP can examine genetic markers for characteristics, including various disease states The principle behind the use of PGP is that, since it is known that numerical chromosomal abnormalities explain most of the cases of pregnancy loss, and a large proportion of the human embryos are aneuploid, the selective replacement of euploid embryos should increase the chances of a successful IVF treatment. Whole-genome sequencing provides an alternative to such methods of comprehensive chromosome analysis methods as array-comparative genomic hybridization (aCGH), quantitative PCR and SNP microarrays. Whole full genome sequencing can provide information regarding single base changes, insertions, deletions, structural variations and copy number variations, for example.

As PGD can be performed on cells from different developmental stages, the biopsy procedures vary accordingly. The biopsy can be performed at all preimplantation stages, including but not limited to unfertilised and fertilised oocytes (for polar bodies, PBs), on day three cleavage-stage embryos (for blastomeres) and on blastocysts (for trophectoderm cells).

In view of the foregoing detailed description of the invention, according to one aspect of the invention, methods are provided for sequencing a complex nucleic acid of an organism (for example, a mammal such as a human, whether a single, individual organism or a population comprising more than one individual), such methods comprising: (a) aliquoting a sample of the complex nucleic acid to produce a plurality of aliquots, each aliquot comprising an amount of the complex nucleic acid; (b) sequencing the amount of the complex nucleic acid from each aliquot to produce one or more reads from each aliquot; and (c) assembling the reads from each aliquot to produce an assembled sequence of the complex nucleic acid comprising no more than one, 0.8, 0.7, 0.6, 0.5, 0.4, 0.3, 0.2, 0.1, 0.08, 0.06, 0.04 or less false single nucleotide variants per megabase at a call rate of 70, 75, 80, 85, 90 or 95 percent or greater. If the complex nucleic acid is a mammalian (e.g., human) genome, the assembled sequence optionally has a genome call rate of at 70 percent or greater and an exome call rate of 70, 75, 80, 85, 90 or 95 percent or greater. According to one embodiment, the complex nucleic acid comprises at least one gigabase.

According to one embodiment of such methods, the complex nucleic acid is double-stranded, and the method comprises separating single strands of the double-stranded complex nucleic acid before aliquoting.

According to another embodiment, such methods comprise fragmenting the amount of the complex nucleic acid in each aliquot to produce fragments of the complex nucleic acid. According to one embodiment, such methods further comprise tagging the fragments of the complex nucleic acid in each aliquot with an aliquot-specific tag (or a set of aliquot specific tags) by which the aliquot from which tagged fragments originate is determinable. In one embodiment, such tags are polynucleotides, including, for example, tags that comprise an error-correction code or an error-detection code, including without limitation, a Reed-Solomon error-correction code.

According to another embodiment, such methods comprise pooling the aliquots before sequencing.

According to another embodiment of such methods, the sequence comprises a base call at a position of the sequence, and such methods comprise identifying the base call as true if it originates from two or more aliquots, or from three or more reads originating from two or more aliquots.

According to another embodiment, such methods comprise identifying a plurality of sequence variants in the assembled sequence and phasing the sequence variants.

According to another embodiment of such methods, the sample of the complex nucleic acid comprises 1 to 20 cells of the organism or genomic DNA isolated from the cells, which may be purified or unpurified. According to another embodiment, the sample comprises between 1 pg and 100 ng, e.g., 1 pg, 6 pg, 10 pg, 100 pg, 1 ng, 10 ng or 100 ng of genomic DNA, or from 1 pg to 1 ng, or from 1 pg to 100 pg, or from 6 pg to 100 pg. For reference purposes, a single human cell contains approximately 6.6 pg of genomic DNA.

According to another embodiment, such methods comprise amplifying the amount of the complex nucleic acid in each aliquot.

According to another embodiment of such methods, the complex nucleic acid is selected from the group consisting of a genome, an exome, a transcriptome, a methylome, a mixture of genomes of different organisms, a mixture of genomes of different cell types of an organism, and subsets thereof.

According to another embodiment of such methods, the assembled sequence has a coverage of 80×, 70×, 60×, 50×, 40×, 30×, 20×, 10×, or 5×. Lower coverage can be used with longer reads.

According to another aspect of the invention, an assembled sequence of a complex nucleic acid of a mammal is provided that comprises fewer than one false single nucleotide variants per megabase at a call rate of 70 percent or greater.

According to another aspect of the invention, methods are provided for sequencing a complex nucleic acid of an organism comprising: (a) providing a sample comprising from 1 pg to 10 ng of the complex nucleic acid; (b) amplifying the complex nucleic acid to produce an amplified nucleic acid; and (c) sequencing the amplified nucleic acid to produce a sequence having a call rate of at least 70 percent of the complex nucleic acid. According to one such method, the complex nucleic acid is unpurified. According to another embodiment, such a method comprises amplifying the complex nucleic acid by multiple displacement amplification. According to another embodiment, such methods comprise amplifying the complex nucleic acid at least 10, 100, 1000, 10,000 or 100.000-fold or more. According to another embodiment of such methods, the sample comprises 1 to 20 cells (or cell nuclei) comprising the complex nucleic acid. According to another embodiment, such methods comprise lysing the cells (or nuclei), the cells comprising the complex nucleic acid and cellular contaminants, and amplifying the complex nucleic acid in the presence of the cellular contaminants. According to another embodiment of such methods, the cells are circulating non-blood cells from blood of the higher organism. According to another embodiment of such methods, the assembled sequence has a call rate of 70, 75, 80, 85, 90, or 95 percent or more. According to another embodiment of such methods, the sequence comprises 2, 1, 0.8, 0.7, 0.6, 0.5, 0.4, 0.3, 0.2, 0.1, 0.08, 0.06, 0.04 or less false single nucleotide variants per megabase. According to another embodiment, such methods further comprise: aliquoting the sample to produce a plurality of aliquots, each aliquot comprising an amount of the complex nucleic acid; amplifying said amount of the complex nucleic acid in each aliquot to produce an amplified nucleic acid in each aliquot; sequencing the amplified nucleic acid from each aliquot to produce one or more reads from each aliquot; and assembling the reads to produce the sequence. According to another embodiment, such methods further comprise: fragmenting the amplified nucleic acid in each aliquot to produce fragments of the amplified nucleic acid in each aliquot; and tagging the fragments of the amplified nucleic acid in each aliquot with an aliquot-specific tag to produce tagged fragments in each aliquot. According to another embodiment of such methods, a base call at a position of the sequence is accepted as true if it is present in reads from two or more aliquots, or, more stringently, 3 or more times in reads from two or more aliquots. According to another embodiment, such methods further comprise identifying a sequence variation in the sequence that is informative regarding a characteristic (e.g, the medical status) of the organism. According to another embodiment, the cells are circulating non-blood cells from blood (or other sample) of the higher organism, including without limitation, fetal cells from a mother's blood and cancer cells from the blood of a patient who has a cancer. According to another embodiment of the invention, the complex nucleic acids are circulating nucleic acids (CNAs). Thus, the characteristic of the organism to be assessed may include, without limitation, the presence of and information regarding a cancer, whether the organism is pregnant, and the sex or genetic information about a fetus carried by a pregnant individual. For example, such methods are useful for identifying single base variations, insertions, deletions, copy number variations, structural variations or rearrangements, etc. that are correlated with the likelihood of disease, a medical diagnosis or prognosis, etc. According to another embodiment of the invention, methods are provided for assessing a genetic status of an embryo (e.g., sex, paternity, presence or absence of a genetic abnormality or genotype that is associated with predisposition to disease, etc.) comprising: (a) providing between about one and 20 cells of the embryo; (b) obtaining an assembled sequence produced by sequencing genomic DNA of said cells, wherein the assembled sequence has a call rate of at least 80 percent; and (c) comparing the assembled sequence to a reference sequence to assess the genetic status of the embryo. For example, such methods are useful for identifying single base variations, insertions, deletions, copy number variations, structural variations or rearrangements, etc. that are correlated with the likelihood of disease, a medical diagnosis or prognosis, etc. According to another embodiment, methods are provided for assessing a genetic status of an embryo (e.g., sex, paternity, presence or absence of a genetic abnormality or genotype that is associated with predisposition to disease, etc.) comprising: (a) providing between about one and 20 cells of the embryo; (b) obtaining an assembled sequence produced by sequencing genomic DNA of said cells, wherein the assembled sequence has a call rate of at least 80 percent of the genome of the embryo; and (c) comparing the assembled sequence to a reference sequence to assess the genetic status of the embryo.

According to another aspect of the invention, an assembled whole human genome sequence is provided, the sequence comprising no more than one false single nucleotide variants per megabase and a call rate of at least 70 percent, wherein the sequence is produced by sequencing between 1 pg and 10 ng of human genomic DNA.

According to another aspect of the invention, methods are provided for phasing sequence variants of a genome of an individual organism comprising a plurality of chromosomes, the method comprising: (a) providing a sample comprising a mixture of vector-free fragments of each of said plurality of chromosomes; (b) sequencing the vector-free fragments to produce a genome sequence comprising a plurality of sequence variants; and (c) phasing the sequence variants. According to one embodiment, such methods comprise phasing at least 70, 75, 80, 85, 90, or 95 percent or more of the sequence variants. According to another embodiment of such methods, the genome sequence has a call rate of at least 70 percent of the genome. According to another embodiment of such methods, the sample comprises from 1 pg to 10 ng of the genome, or from 1 to 20 cells of the individual organism. According to another embodiment of such methods, the genome sequence has fewer than one false single nucleotide variant per megabase.

According to another aspect of the invention, methods are provided for phasing sequence variants of a genome of an individual organism that comprises a plurality of chromosomes, the method comprising: providing a sample comprising fragments of said plurality of chromosomes; sequencing the fragments to produce a whole genome sequence without cloning the fragments in a vector, wherein the whole genome sequence comprises a plurality of sequence variants; and phasing the sequence variants. According to one embodiment of such methods, phasing sequence variants occurs during assembly of the whole genome sequence.

EXAMPLES

Example 1

Comparison of DNA Amplification Methods

Preimplantation Genetic Diagnosis (PGD) is a form of prenatal diagnosis that consists of the genetic screening of in vitro fertilization (IVF)-generated embryos (usually ten on average per cycle) before they are transferred to the future mother. It is usually applied to women of advanced maternal age (>34 years) or for couples at risk of transmitting a genetic disease. Current techniques used for the genetic screening are fluorescence in situ hybridization (FISH), comparative genomic hybridization (CGH), array CGH and SNP arrays for the detection of chromosome abnormalities, and PCR and SNP arrays for the detection of gene defects. PGD for single gene defects currently consists of custom designed assays unique to each patient, often combining specific mutation detection with linkage analysis as a back-up and to control for and monitor contamination. Usually one cell is biopsied from each embryo on day 3 of development and results given on day 5, which is the latest that an embryo can be transferred. Blastocyst biopsy is starting to be applied, which consists of the biopsy of 3-15 cells from the trophectoderm of a blastocyst (a day 5 embryo), followed by embryo freezing. The embryos can remain frozen indefinitely without significant loss of potential, which is suitable for whole genome sequencing, permitting the biopsies to be obtained at one site then transferred to another site for whole genome sequencing. Whole genome sequencing of blastocyst biopsies would make possible a "universal" PGD test for single gene defects and other genetic abnormalities that could be identified by this technology.

Following conventional ovarian stimulation and egg retrieval, eggs were fertilized by intracytoplasmic sperm injection (ICSI) to avoid sperm contamination in the PGD test. Following growth to day 3, embryos were biopsied using fine glass needles and one cell removed from each embryo. Each blastomere was added individually to a clean tube, covered with molecular-grade oil and shipped on ice to a PGD lab. The samples were processed immediately upon arrival using a test designed to amplify the mutation of a CTG repeat expansion in the gene DMPK and two linked markers.

Following clinical PGD testing and embryo transfer, unused embryos were donated to the IVF clinic and used in developing new PGD testing modalities. Eight blastocysts were donated and used in these experiments.

Figure 15:
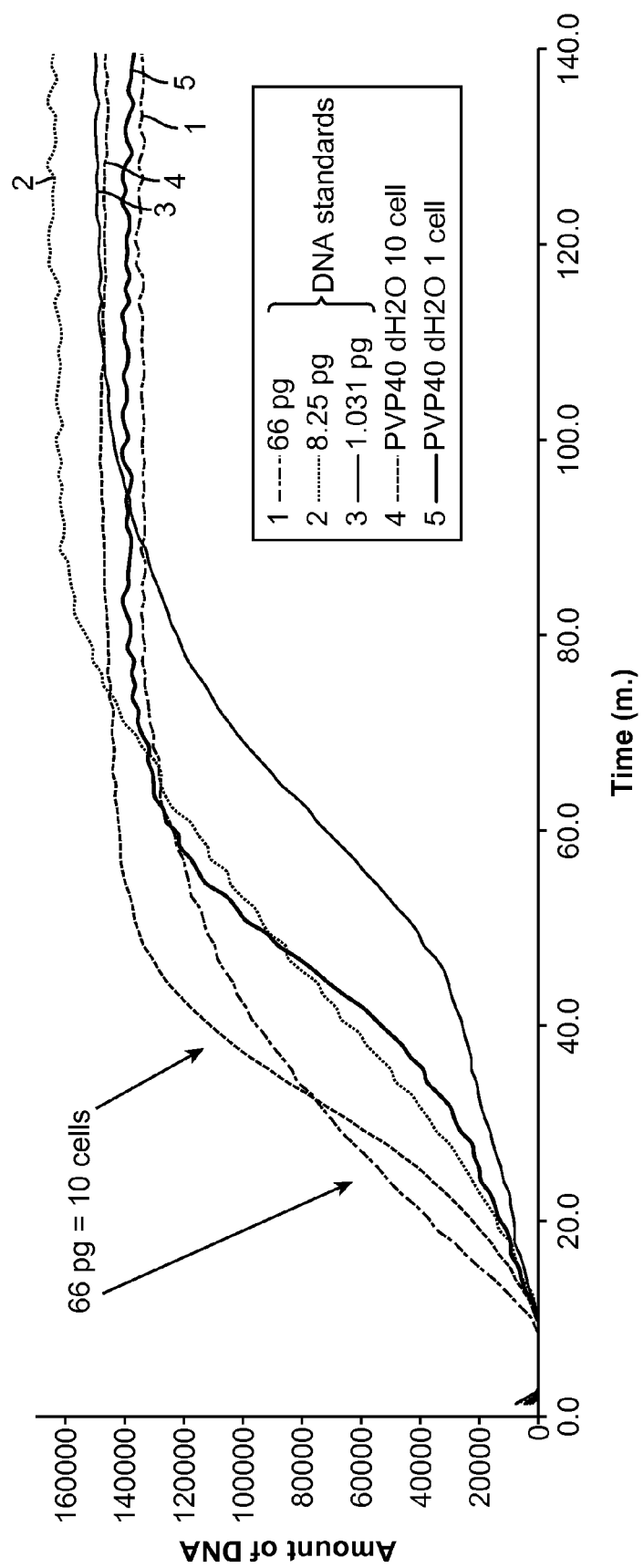
FIG. 15 is a graph showing amplification of purified genomic DNA standards (1.031, 8.25 and 66 picograms [pg]) and one or ten cells of PVP40 using a Multiple Displacement Amplification (MDA) protocol as described in Example 1.

A blastocyst biopsy provides approximately 6.6 picograms (pg) of genomic DNA per cell. Amplification provides sufficient DNA for whole genome sequencing. FIG. 15 shows results of amplification of 1.031 pg, 8.25 pg and 66 pg of purified genomic DNA standards and 1 or 10 cells of PVP40 by MDA using our protocol (as described below). The MDA reaction can be run for as long as necessary (for example, from 30 min to 120 min) to obtain the amount of DNA needed for a particular sequencing method. It is expected that the greater the extent of amplification, the more GC bias will result.

Two DNA amplification methods were compared to identify a method for generating a sufficient quality template DNA for whole genome sequence analysis while minimizing the introduction of GC bias. We compared our protocol with the SurePlex Amplification System (Rubicon Genomics Inc., Ann Arbor, Mich.) is commonly used for array CGH, and a modified MDA.

A biopsy of 10-20 cells was obtained from embryos affected with the R-1MT mutation of Myotonic Dystrophy. The samples were lysed and the DNA denatured in a single tube, then amplified by MDA using our protocol and the SurePlex kit according to the manufacturer's instructions. Approximately 2 ug of DNA were generated by both amplification methods. Prior to whole genome sequence analysis, amplified samples were screened with 96 independent qPCR markers spread across the genome to select samples with the lowest amount of bias. FIG. 16 shows the results. Briefly, we determined the average cycle number across the entire plate and subtracted that from each individual marker to compute a "delta cycle" number. The delta cycle was plotted against the GC content of the 1000 base pairs surrounding each marker in order to indicate the relative GC bias of each sample. To get a sense of the overall "noise" of the samples, the absolute value of each delta cycle was summed to create the "sum of deltas" measurement. A low sum of deltas and a relatively flat plotting of the data against GC content yields a well-represented whole genome sequence in our experience. The sum of deltas was 61 for our MDA method and 287 for the SurePlex-amplified DNA, indicating that our protocol produced much less GC bias than the SurePlex protocol.

Example 2

Complete Genomic Sequencing of Blastocyst Biopsies for Use in Preimplantation Genetic Diagnosis (PGD)

A modified multiple displacement amplification (MDA) (Dean et al. (2002) Proc Natl Acad Sci USA 99, 5261-5266)

was employed to generate sufficient template DNA (approximately 1 pg) for whole genome sequence analysis as described herein. Briefly, 5-20 cells from each five-day-old blastocyst were isolated, frozen, and shipped on dry ice from the laboratory at which they were isolated. Samples were thawed and lysed to release genomic DNA. Without purifying the genomic DNA away from cellular contaminants, the DNA was alkaline denatured with the addition of 1 µl of 400 mM KOH/10 mM EDTA. The embryonic genomic DNA was whole genome amplified using a phi29 polymerase-based Multiple Displacement Amplification (MDA) reaction to generate sufficient quantities of DNA (~1 pg) for sequencing. One minute after alkaline denaturation, thio-protected random eight-mers were added to denatured DNA. The mixture was neutralized after two minutes and a master mix containing final concentrations of 50 mM Tris-HCl (pH 7.5), 10 mM $MgCl_2$, 10 mM $(NH_4)_2SO_4$, 4 mM DTT, 250 µM dNTPs (USB, Cleveland, Ohio), and 12 units of phi29 polymerase (Enzymatics, Beverly, Mass.) was added to make a total reaction volume of 100 ul. The MDA reaction was incubated for 45 minutes at 37° C. and inactivated at 65° C. for 5 minutes. Approximately 2 pg of DNA was generated by the MDA reaction. This amplified DNA was then fragmented and used for library construction and sequencing as described above.

Myotonic dystrophy type 1 (DM1) is an autosomal dominant disease caused by a trinucleotide repeat-expansion, cytosine-thymine-guanine $(CTG)_n$, in the 3'-untranslated region of a gene encoding the myotonic dystrophy protein kinase (DMPK). We examined clone coverage across the DMPK CTG repeat region. The sequencing technology described herein results in 35 bp paired-end reads that typically span about 400 bp. For unaffected individuals and one unknown sample 400 bps is sufficient to span this CTG repeat region of both alleles, resulting in a copy number of approximately two. In affected individuals and one unknown sample a copy number of about one is observed, suggesting that the repeat expansion is too large for the 400 bp paired ends to span; only the unaffected allele has coverage in this region.

Table 1 below provides summary information for mapping and assembly of PGD embryo samples. All variations and mapping statistics are with respect to the National Center for Biotechnology Information (NCBI) version 37 human genome reference assembly. The amplifications of samples 2A, 5B, and 5C were of poorer quality, resulting in less of the genome called and a reduction in the total number of SNPs identified. Samples 5B and 5C are separate biopsies from the same embryo. Sample NA20502 was processed following the standard procedure without any amplification prior to library preparation.

Figure 17:
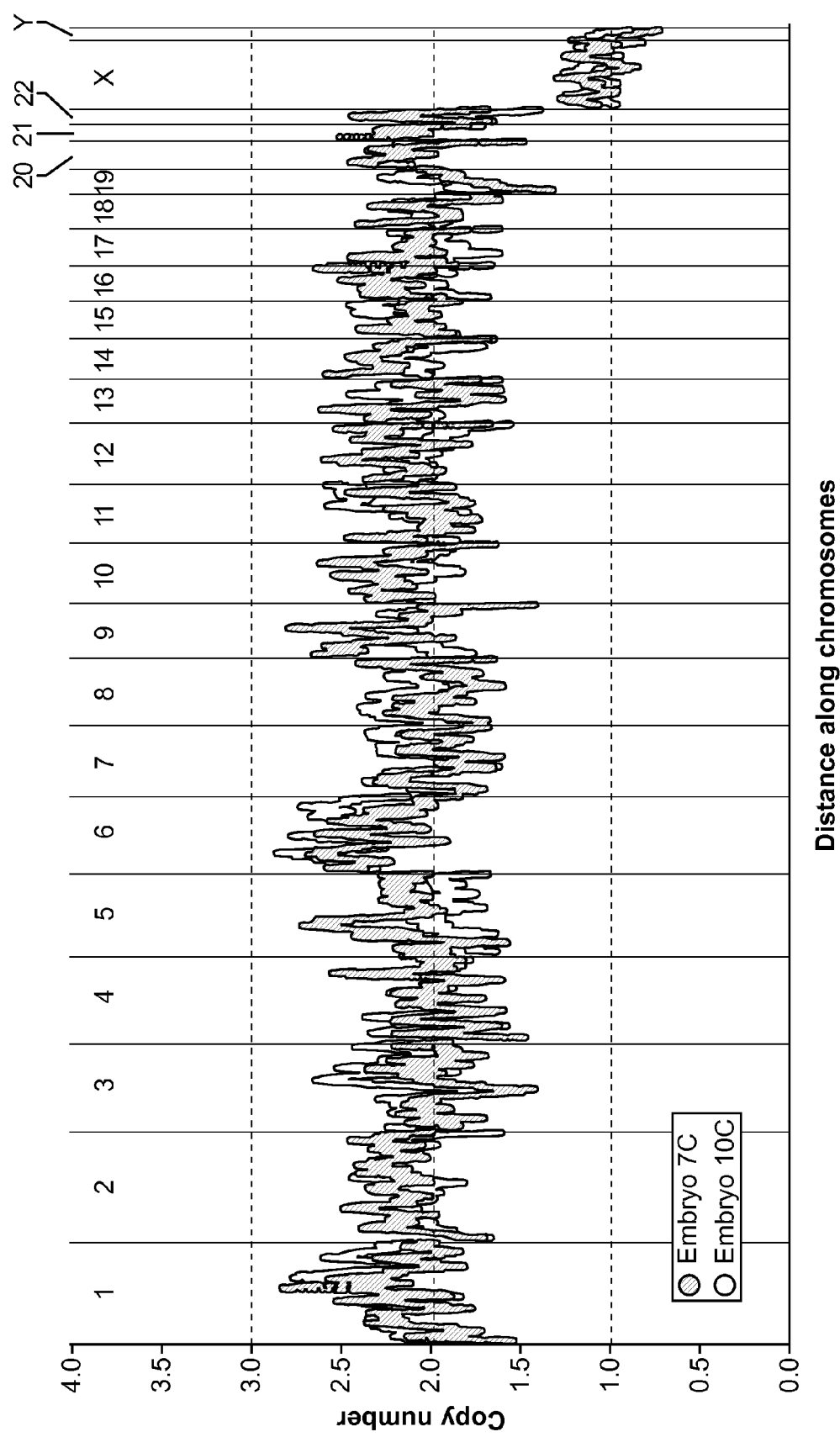
FIG. 17 shows genomic coverage of samples 7C and 10C. Coverage was plotted using a megabase moving average of 100 kilobase coverage windows normalized to haploid genome coverage. Dashed lines at copy numbers 1 and 3 represent haploid and triploid copy numbers respectively. Both embryos are male and have haploid copy number for the X and Y chromosome. No other losses or gains of whole chromosomes or large segments of chromosomes are evident in these samples.

FIG. 17 shows genomic coverage of two samples (7C and 10C). Coverage was plotted using a 10 megabase moving average of 100 kilobase coverage windows normalized to haploid genome coverage. Dashed lines at copy numbers 1 and 3 represent haploid and triploid copy numbers respectively. Both embryos are male and have a haploid copy number for the X and Y chromosome. No other losses or gains of whole chromosomes or large segments of chromosomes were evident in these samples.

The poorest performing samples achieving a genome coverage of 85% and the best samples covering 95% of the genome, a level similar to a standard whole genome sequencing process by the above-described methods using several micrograms of purified, unamplified human genomic DNA ("standard sequencing"). In general, the coverage was "noisy" compared to standard sequencing, but using a moving average of 10 megabases allows for accurate detection of whole chromosome and chromosomal arm amplifications and deletions. We also demonstrate that many polymorphisms can be detected and that the risk for development of certain diseases, aside from the DMPK mutation, can be used for blastocyst implantation selection.

In this Example, the starting genomic DNA was excessively amplified (approximately ten times more than necessary) in order to ensure that ample quantities of genomic DNA was available for sequencing. Reducing the extent of amplification would be expected to improve sequence coverage and sequencing quality. Amplification can also be reduced by permitting biopsied tissue (or other starting material, such as a cancer biopsy or needle aspirate, fetal or cancer cell(s) isolated from the bloodstream, etc.) to grow in culture. This approach adds somewhat to the overall turnaround time for the process. However, culturing the small number of available cells results in high-fidelity "amplification" of the genomic DNA in the cellular process of chromosomal replication.

Because the DMPK mutation is a trinucleotide repeat disease, it is difficult to analyze the mutation using the current sequencing process which employs ~400 bp-long mate-pair reads. Longer mate-pair reads (e.g., one kilobase or longer) may be used to span and therefore sequence across these regions, resulting in an accurate determination of the size of the repeat.

Example 3

Clinically Accurate Genome Sequencing and Haplotyping from 10-20 Human Cells

In this Example, 65-130 pg (10-20 cells) of long human genomic DNA (50% 60-500 kb in length) was split into 384 aliquots, amplified, fragmented and tagged in each aliquot. After sequencing, a diploid (phased) genome was assembled without DNA cloning or separation of metaphase chromosomes. Ten LFR libraries were used to generate ~3.3 terabases (Tb) of mapped reads from seven distinct genomes. Up to 97% of the heterozygous single nucleotide variants (SNVs) were assembled into contigs wherein 50 percent of the covered bases (N50) were in contigs longer than ~500 kb for samples of European ethnicity and ~1 Mb for an African sample. In extensive comparisons between replicate libraries, LFR haplotypes were found to be highly accurate, with one false positive SNV per 10 megabases (Mb). Despite starting with 100 picogram (pg) of DNA and 10.000-fold in vitro amplification, this 20-30-fold increase in accuracy compared to non-LFR genomes (Drmanac et al., Science 327:78, 2010; Roach et al., Am. J. Hum. Genet. 89:382-397, 2011) is achieved because most errors are inconsistent with real haplotypes. We have demonstrated cost-effective and clinically accurate genome sequencing and haplotyping from 10-20 human cells.

LFR technology is a cost effective DNA pre-processing step without cloning or the isolation of whole metaphase chromosomes that allows for the complete sequencing and assembly of separate parental chromosomes at a clinically relevant cost and scale. LFR can be adapted for use as a pre-processing step before any sequencing method, although we employed a short-read sequencing technology as described in detail above.

LFR can generate long-range phased SNPs because it is conceptually similar to single molecule sequencing of fragments 10-1000 kb in length. This is achieved by the stochastic separation of corresponding parental DNA fragments into physically distinct pools, without any DNA cloning steps, followed by fragmentation to generate shorter fragments, a similar to the aliquoting of fosmid clones (Kitzman et al., Nat. Biotechnol. 29:59-63, 2011; Suk et al., Genome Res. 21:1672-1685, 2011). As the fraction of the genome in each pool decreases to less than a haploid genome, the statistical likelihood of having a corresponding fragment from both parental chromosomes in the same pool dramatically diminishes. Likewise, the more individual pools that are interrogated, the greater the number of times a fragment from the maternal and paternal homologs will be analyzed in separate pools.

For example, a 384-well plate with 0.1 genome equivalents in each well yields a theoretical 19× coverage of both the maternal and paternal alleles of each fragment. Such a high initial DNA redundancy of ~19× yields more complete genome coverage and higher variant calling and phasing accuracy than is achieved using strategies that employ fosmid pools, which result in coverage ranging from about 3× (Kitzman et al., Nat. Biotechnol 29:59-63, 2011) to about 6× (Suk et al., Genome Res. 21:1672-1685, 2011).

Figure 18:
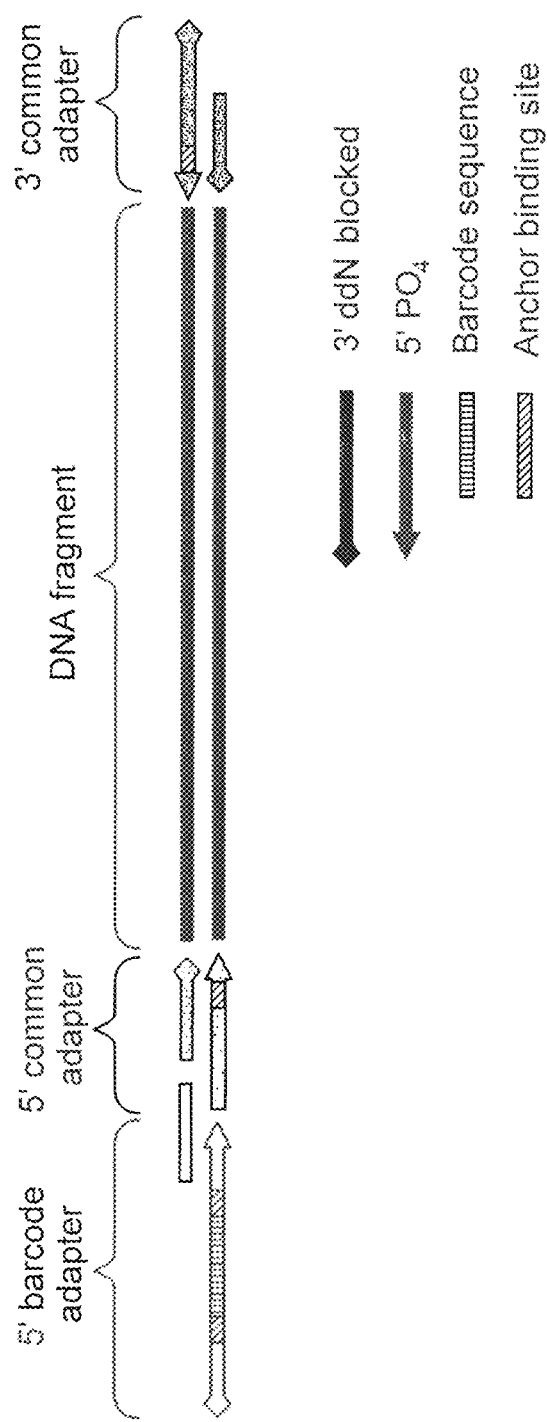
FIG. 18 is a schematic illustration of embodiments of a barcode adapter design for use in methods of the invention. LFR adapters are composed of a unique 5' barcode adapter, a common 5' adapter, and a common 3' adapter. The common adapters are both designed with 3' dideoxy nucleotides that are unable to ligate to the 3' fragment, which eliminates adapter dimer formation. After ligation, the block portion of the adapter is removed and replaced with an unblocked oligonucleotide. The remaining nick is resolved by subsequent nick translation with Taq polymerase and ligation with T4 ligase.

To prepare LFR libraries in a high-throughput manner we developed an automated process that performs all LFR-specific steps in the same 384-well plate. The following is an overview of the process. First, a highly uniform amplification using a modified phi29-based multiple displacement amplification (MDA; Dean et al., Proc. Natl. Acad. Sci. U.S.A. 99:5261, 2002) is performed to replicate each fragment about 10,000 times. Next, through a process of enzymatic steps within each well without intervening purification steps, DNA is fragmented and ligated with barcode adapters. Briefly, long DNA molecules are processed to blunt-ended 300-1,500 bp fragments through Controlled Random Enzymatic fragmenting (CORE). CoRE fragments DNA through removal of uridine bases, which are incorporated at a predefined frequency during MDA by uracil DNA glycosylase and endonuclease IV. Nick translation from the resulting single-base gaps with $E.\ coli$ polymerase 1 resolves the fragments and generates blunt ends. Unique 10-base Reed-Solomon error-correcting barcode adapters (PCT/US2010/023083, published as WO 2010/091107, incorporated herein by reference), which are designed to reduce any bias caused by differences in the sequence and concentration of each barcode (FIG. 18), are then ligated to fragmented DNA in each well using a high-yield, low-chimera formation protocol (Drmanac et al., Science 327:78, 2010). Lastly, all 384 wells are combined and an unsaturated polymerase chain reaction is employed using primers common to the ligated adapters to generate sufficient template for short-read sequencing platforms. The following provides greater detail regarding the LFR protocol that we employed.

High molecular weight DNA was purified from cell lines GM12877, GM12878, GM12885, GM12886, GM12891, GM12892 GM19240, and GM20431 (Coriell Institute for Medical Research, Camden, N.J.) using a RecoverEase DNA isolation kit (Agilent, La Jolla, Calif.) following the manufacturer's protocol. High molecular weight DNA was partially sheared to make it more amenable to manipulation by pipetting 20-40 times using a Rainin P1000 pipette. 200 ng of genomic DNA was analyzed on 1% agarose gel with 0.5×TBE buffer using a BioRad CHEF-DR II with the following parameters: 6V/cm, 50-90 second ramped switch time, and a 20 hour total run. 500 ng of Yeast Chromosome PFG Marker (New England Biolabs, Ipswich, Mass.) and Lambda Ladder PFG Marker (New England Biolabs, Ipswich, Mass.) were used to determine the length of purified genomic DNA.

In addition, immortalized cell line GM19240 (Coriell Institute for Medical Research, Camden, N.J.) was grown in RPMI supplemented with 10% FBS under standard environmental conditions for cell culture. Individual cells were isolated under 200× magnification with a micromanipulator (Eppendorf, Hamburg, Germany) and deposited into a 1.5 ml microtube with 10 ul of $dH_2O$. The cells were denatured with 1 ul of 20 mM KOH and 0.5 mM EDTA. The denatured cells were then entered into the LFR process.

DNA from each of the various cell lines was diluted and denatured at a concentration of 50 pg/ul in a solution of 20 mM KOH and 0.5 mM EDTA. After a one minute incubation at room temperature 120 pg of denatured DNA was removed and added to 32 ul of 1 mM 3' thio protected random octamers (IDT, Coralville, Iowa). After two minutes the mixture was brought to a volume of 400 ul with $dH_2O$ and 1 ul was distributed to each well of a 384 well plate. 1 µl of a 2× phi29 polymerase (Enzymatics Inc., Beverly, Mass.) based multiple displacement amplification (MDA) mix was added to each well to generate approximately 3-10 nanograms of DNA (10,000- to 25.000-fold amplification). The MDA reaction consisted of 50 mM Tris-HCl (pH 7.5), 10 mM $MgCl_2$, 10 mM $(NH_4)_2SO_4$, 4 mM DTT, 250 uM dNTPs (USB, Cleveland, Ohio), 10 uM 2'-deoxyuridine 5'-triphosphate (dUTP) (USB, Cleveland, Ohio), and 0.25 units of phi29 polymerase.

Controlled Random Enzymatic Fragmentation (CORE) was then performed. Excess nucleotides were inactivated and uracil bases were removed by a 120 minute incubation of the MDA reaction with a mixture of 0.031 units of shrimp alkaline phosphatase (SAP) (USB, Cleveland, Ohio), 0.039 units of uracil DNA glycosylase (New England Biolabs, Ipswich, Mass.) and 0.078 units of endonuclease IV (New England Biolabs, Ipswich, Mass.) at 37° C. SAP was heat inactivated at 65° C. for 15 minutes. A 60 minute room temperature nick translation with 0.1 units of $E.\ coli$ DNA polymerase 1 (New England Biolabs, Ipswich, Mass.) in the same buffer with the addition of 0.1 nanomoles of dNTPs (USB, Cleveland, Ohio) resolved the gaps and fragmented the DNA to 300-1,300 base pair fragments. $E.\ coli$ DNA polymerase 1 was heat inactivated at 65° C. for 10 minutes. Remaining 5' phosphates were removed by incubation with 0.031 units of SAP (USB, Cleveland, Ohio) for 60 minutes at 37° C. SAP was heat inactivated at 65° C. for 15 minutes.

Tagged adapter ligation and nick translation were then performed. Ten base DNA barcode adapters, unique for each well, were attached to the fragmented DNA using a two part directional ligation approach. Approximately 0.03 pmol of fragmented MDA product were incubated for 4 hours at room temperature in a reaction containing 50 mM $Tris_LHCl$ (pH 7.8), 2.5% PEG 8000, 10 mM MgCl2, 1 mM rATP, a 100-fold molar excess of $5_L$phosphorylated (5'PO4) and 3' dideoxy terminated (3' dd) common Ad1 (FIG. 18) and 75 units of T4 DNA ligase (Enzymatics, Beverly, Mass.) in a total volume of 7 ul. Ad1 contained a common overhang region for hybridization and ligation to a unique barcode adapter. After four hours, a 200-fold molar excess of unique 5' phosphorylated tagged adapters were added to each well and allowed to incubate 16 hours. The 384 wells were combined to a total volume of ~2.5 ml and purified by the addition of 2.5 ml of AMPure beads (Beckman-Coulter, Brea, Calif.). One round of PCR was performed to create a molecule with a 5' adapter and tag on one side and a 3' blunt end on the other side. The 3' adapter was added in a ligation reaction similar to the 5' adapter as described above. To seal nicks created by the ligation, the DNA was incubated for 5 minutes at 60° C. in a reaction containing 0.33 uM Ad1

PCR1 primers, 10 mM Tris·HCl (pH 78.3), 50 mM KCl, 1.5 mM MgCl2, 1 mM rATP, 100 uM dNTPs, to exchange 3' dideoxy terminated Ad1 oligos with 3'-OH terminated Ad1 PCR1 primers. The reaction was then cooled to 37° C. and, after addition of 90 units of Taq DNA polymerase (New England Biolabs, Ipswich, Mass.) and 21600 units of T4 DNA ligase, was incubated a further 30 minutes at 37° C., to create functional 5'-PO4 gDNA termini by Taq catalyzed nick translation from Ad1 PCR1 primer 3'-OH termini, and to seal the resulting repaired nicks by T4 DNA ligation. At this point the material was incorporated into the standard DNA nanoarray sequencing process.

RNA-Seq data were derived starting from the total RNA, using the Ovation RNA-Seq kit (NuGen, San Carlos, Calif.) and SPRIWork (Beckman-Coulter, Brea, Calif.) to prepare a sequencing library with an average insert size of 150-200 bp. A 75 bp paired-end sequencing reaction was performed on HiSeq 2000 (Illumina, San Diego, Calif.) at the Center for Personalized Genetic Medicine (Harvard Medical School, Boston, Mass.). Paired-end reads were assembled with tophat v1.2.0 (Trapnell et al., Bioinformatics 25:1105-1111, 2009) using bowtie v0.12.7 (Langmead et al., Genome Biol. 10:R25, 2009), and single nucleotide variants (SNVs) were called using the GATK UnifiedGenotyper v1.1 (http://www.broadinstitute.org/gsa/wiki/index.php/GATK_release_1.1) with hg19 for reference and dbSNP version 132 to annotate known SNPs. SNVs were mapped both to genes from RefSeq and to isoforms in the transcriptome as identified by cufflinks v1.0.3 (http://cufflinks.cbcb.umd.edu/tutorial.html).

To identify haplotypes of co-expressed alleles, the data were filtered for heterozygous SNVs that occur both on the same LFR contig and on the same gene with at least one other heterozygous SNV. Where transcripts exhibit allele-specific expression, heterozygous alleles expressed on an LFR-phased haplotype should all have higher, or all have lower read counts than their counterparts on the other haplotype. Here we identify the higher-expressed haplotype as the one for which the majority of its het alleles exhibit higher expression than their counterparts. A heterozygous is counted as "concordant" if its expression agrees with its containing haplotype. In cases of ties, where there is no haplotype majority, half of the heterozygous SNVs are counted as concordant. Additionally, in order to be considered at all, the heterozygous SNV is required to have at least 20-fold RNA-Seq read coverage. The heterozygous SNVs are further filtered for noise from the GATK genotyper by comparing with the probability of choosing the ASE and coverage at random using the binomial test.

For error-correction purposes each DNB was tagged with a ten-base Reed-Solomon code with 1-base error correction capability for the unknown error location, or two-base error correction capability for when the errors positions are known (U.S. patent application Ser. No. 12/697,995, published as US 2010/0199155, which is incorporated herein by reference). These 384 codes were selected from a comprehensive set of 4096 Reed-Solomon codes with the above properties (U.S. patent application Ser. No. 12/697,995, incorporated herein by reference). Each code from this set has a minimum Hamming distance of three to any other code in the set. For this study, the position of the errors is assumed to be unknown.

Results.

To demonstrate the power of LFR to determine an accurate diploid genome sequence we generated three libraries of Yoruban female HapMap sample NA19240. NA19240 was extensively interrogated as part of a trio (NA19240 is the daughter of samples NA19238 and NA19239) in the HapMap Project (Consortium, Nature 437:1299-1320, 2005; Frazer et al., Nature 449:851-861, 2007), the 1,000 Genomes Project (Nature 467:1061-1073, 2010), and our own efforts (www.completegenomics.com/sequence-data/download-data/). As a result, highly accurate haplotype information can be generated for 1.7 million heterozygous SNPs based upon the redundant sequence data for parental samples NA19238 and NA19239. One NA19240 LFR library was made starting with 10 cells (65 pg of DNA) from the corresponding immortalized B-cell line. Based on a total effective read coverage of 60× and using 384 distinct pools or aliquots of fragments, we estimated that the optimal number of starting cells would be 10 if the DNA was denatured before dispensing into wells (equivalent to cells of dsDNA; Table 1 below). Two replicate libraries were made from an estimated 100-130 pg (equivalent to 15-20 cells) of denatured high molecular weight genomic DNA. It was determined that when starting from denatured isolated DNA the optimal amount per library would be ~100 pg. This amount was selected to achieve more uniform genome coverage by minimizing stochastic sampling of fragments.

Figure 19:
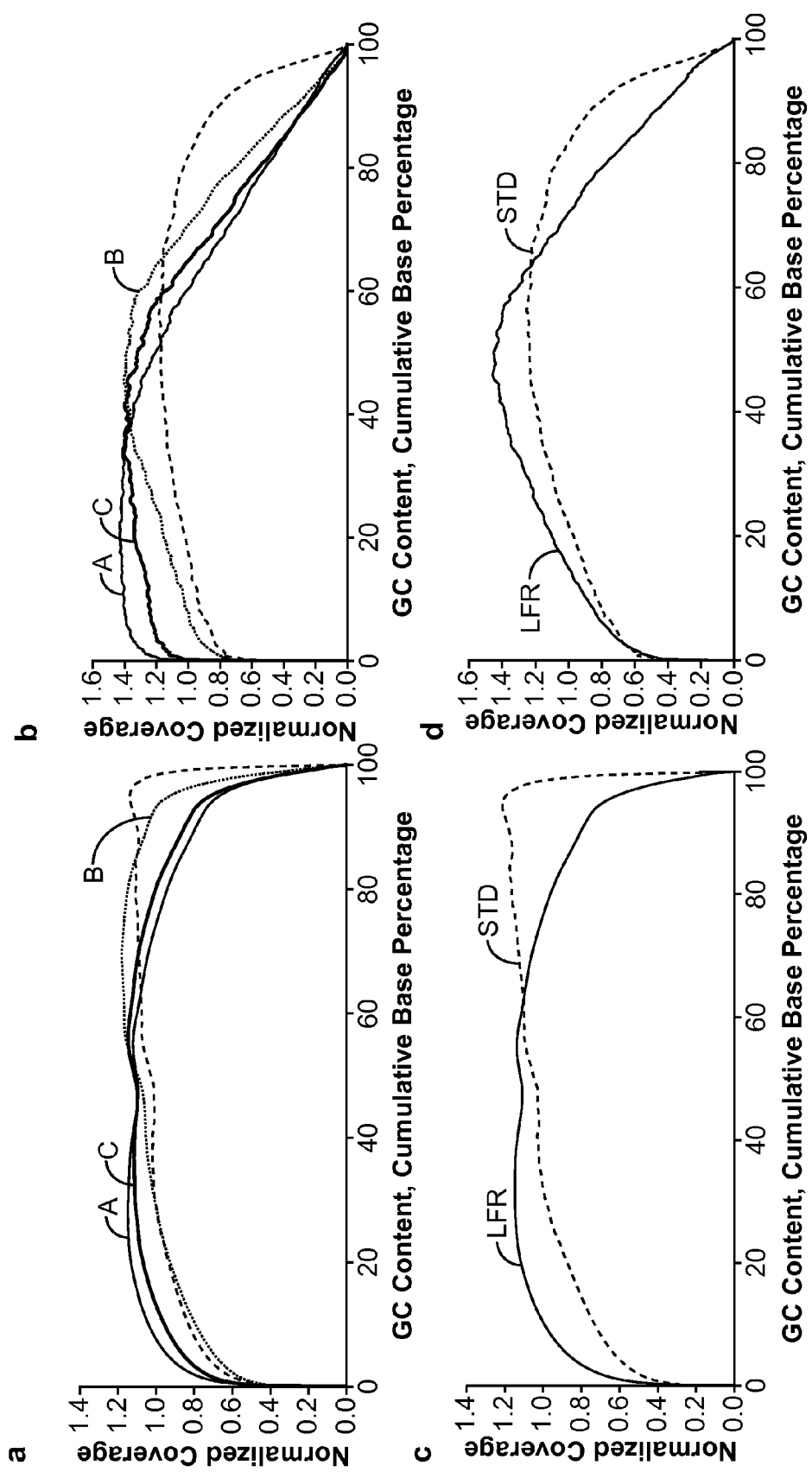
FIG. 19 shows cumulative GC coverage plots. Cumulative coverage of GC was plotted for LFR and standard libraries to compare GC bias differences. For sample NA19240 (a and b), three LFR libraries (Replicate 1, Replicate 2, and 10 cell) and one standard library are plotted for both the entire genome (c) and the coding only portions (d). In all LFR libraries a loss of coverage in high GC regions is evident, which is more pronounced in coding regions (b and d), which contain a higher proportion of GC-rich regions.

All three libraries were analyzed using DNA nanoarray sequencing (Drmanac et al., Science 327:78-81, 2010). 35-base mate-paired reads were mapped to the reference genome using a custom alignment algorithm (Drmanac et al., Science 327:78-81, 2010; Carnevali et al., J. Computational Biol., 19, 2011), yielding on average more than 230 Gbs of mapped data with an average genomic coverage greater than 80× (Table 1 below). Analysis of the mapped LFR data showed two distinct characteristics attributable to MDA: a slight underrepresentation of GC-rich sequences (FIG. 19) and an increase in chimeric sequences. In addition, coverage normalized across 100 kb windows was approximately two-fold more variable. Nevertheless, almost all genomic regions were covered with sufficient reads (five or more), demonstrating that 10.000-fold MDA amplification by our optimized protocol can be used for comprehensive genome sequencing.

Barcodes were used to group mapped reads graphically based on their physical well location within each library, which showed pulses of coverage, i.e., sparse regions of coverage interspersed between long spans with almost no read coverage. On average each well contained between 10-20% of a haploid genome (300-600 Mb) in fragments ranging from 10 kb to over 300 kb in length with N50s of ~60 kb (FIG. 20). Initial fragment coverage was very uniform between chromosomes. As estimated from all detected fragments, the total amount of DNA actually used to make the two libraries from extracted DNA was ~62 pg and 84 pg (equivalent to 9.4 and 12.7 cells, FIG. 20). This is less than the expected 100-130 pg indicating some lost or undetected DNA or imprecision in DNA quantitation. Interestingly, the 10-cell library appeared to be made from ~90 pg (13.6 cells) of DNA, most likely due to some of the cells being in S phase during isolation (FIG. 20).

Figure 21:
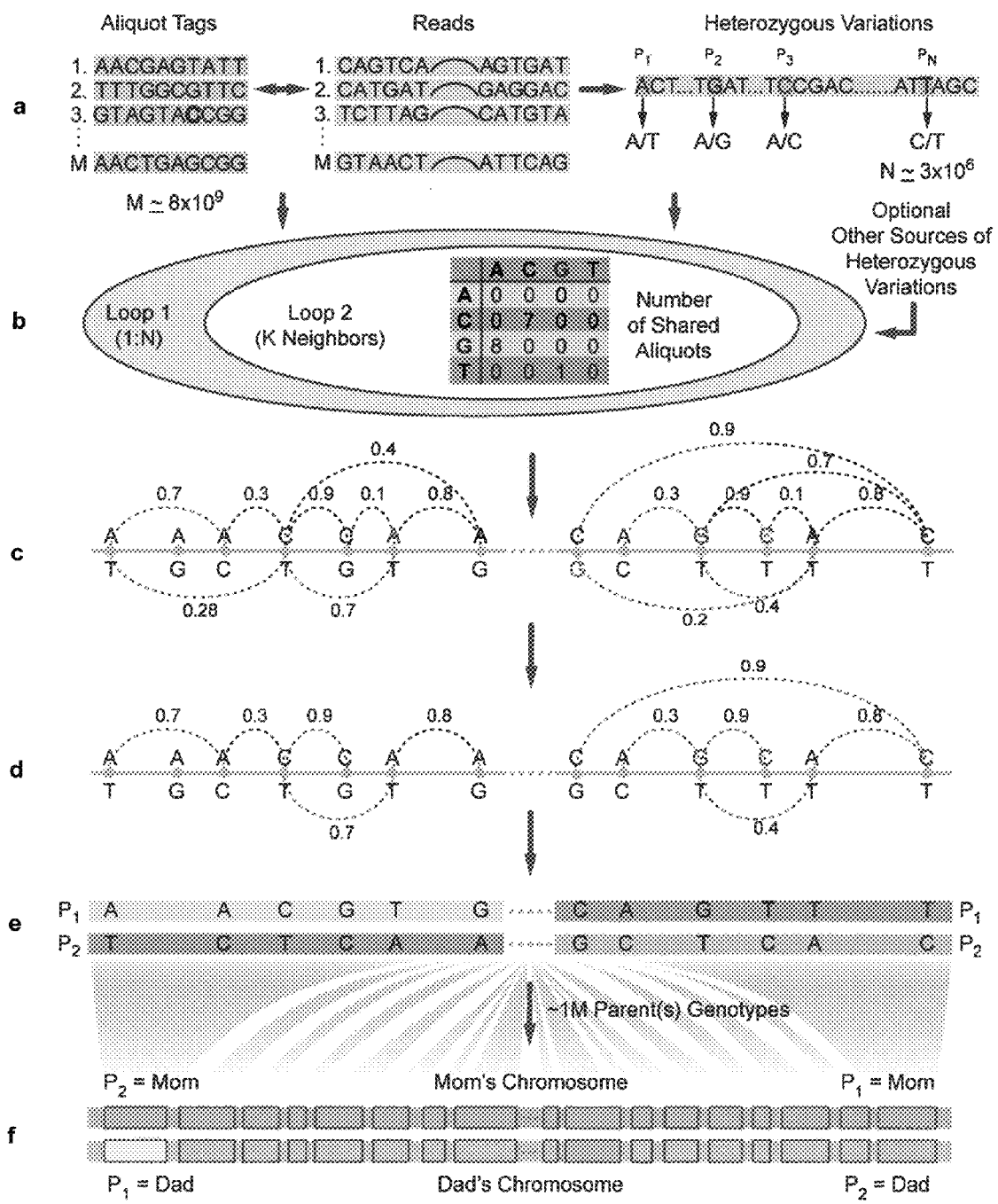
FIG. 21 shows the LFR haplotyping algorithm. (a) Variation extraction: Variations are extracted from the aliquot-tagged reads. The ten-base Reed-Solomon codes enable tag recovery via error correction. Sequences: Aliquot Tag 1 (SEQ ID NO:3); Aliquot Tag 2 (SEQ ID NO:4); Aliquot Tag 3 (SEQ ID NO:5); Aliquot Tag M (SEQ ID NO:6); Reads 1 (SEQ ID NO:7); Reads 2 (SEQ ID NO:8); Reads 3 (SEQ ID NO:9); Reads M (SEQ ID NO:10). (b) Heterozygous SNP-pair connectivity evaluation: The matrix of shared aliquots is computed for each heterozygous SNP-pair within a certain neighborhood. Loop1 is over all the heterozygous SNPs on one chromosome. Loop2 is over all the heterozygous SNPs on the chromosome which are in the neighborhood of the heterozygous SNPs in Loop1. This neighborhood is constrained by the expected number of heterozygous SNPs and the expected fragment lengths. (c) Graph generation: An undirected graph is made, with nodes corresponding to the heterozygous SNPs and the connections corresponding to the orientation and the strength of the best hypothesis for the relationship between those SNPs. (As used herein, a "node" is a datum [data item or data object] that can have one or more values representing a base call or other sequence variant (e.g., a het or indel) in a polynucleotide sequence.) The orientation is binary.

Using a two-step custom haplotyping algorithm that was designed to integrate low-coverage read data (less than 2× coverage) from ~40 individual wells, overlapping heterozygous SNPs from fragments of the same parental chromosome located in different wells were assembled as haplotype contigs (FIG. 21). Unlike other experimental approaches (Kitzman et al., Nat. Biotechnol. 29:59-63, 2011; Suk et al., Genome Res. 21:1672-1685, 2011; Duitama et al., Nucleic Acids Res. 40:2041-2053, 2012) LFR does not define haplotypes for each initial fragment. Instead, LFR assures complete representation of the genome by maximizing the input of DNA fragments for a given read coverage and number of aliquots.

In the first step, heterozygous SNPs from an unphased NA19240 genome assembly (www.completegenomics.com/sequence-data/download-data/) were combined with each LFR library to create a comprehensive set of SNPs for phasing. Next, a network was constructed for each chromosome, where the nodes corresponded to the heterozygous SNP calls and the connections related to the scores of connectivity between each pair of SNPs. Along with the score of the connection, an orientation was also obtained as part of the search for the best hypothesis for each pair of heterozygous SNPs. This highly redundant sparse network of connections was then pruned using domain knowledge and subsequently optimized using Kruskal's minimum-spanning tree (MST) algorithm. This resulted in long contigs with an N50 from 950-1200 kb being obtained for these libraries (FIG. 20).

In total approximately 2.4 million heterozygous SNPs were phased in each library by LFR (FIG. 20). LFR phased approximately 90% of the heterozygous SNPs that it would have been expected to phase in these libraries. The ten-cell library phased over 98% of variants phased by the two libraries made from isolated DNA, demonstrating the potential of LFR to work from a small number of isolated cells. Doubling the number of reads to ~160× coverage further increased the number of phased heterozygous SNPs to over 2.58 million, thereby increasing the phasing rate to 96% (FIG. 20). Combining replicates 1 and 2 (a total of 768 independent wells), each with 80× coverage, resulted in over 2.65 million heterozygous SNPs phased and resulting in a phasing rate of 97%. Using only the SNP loci called in the LFR library for phasing (omitting step one of the LFR algorithm) resulted mostly in a reduction in the total number of phased SNPs of 5-15% (FIG. 20).

Importantly, the number of phased SNPs by LFR only (starting from only 10-20 cells of DNA) was slightly higher than the number of SNPs phased by current fosmid approaches (Kitzman et al., Nat. Biotechnol. 29:59-63, 2011; Suk et al., Genome Res. 21:1672-1685, 2011; Duitama et al., Nucleic Acids Res. 40:2041-2053, 2012). Because a large fraction of variants in children are shared by both parents, this is substantially more than the 81% of heterozygous SNPs that can be phased by using standard parental sequences (Roach et al., Am. J. Hum. Genet. 89:382-397, 2011). Adding parent-derived haplotype data to the 768-well library improves the phasing rate to 98%. About 115,000 (~4%) phased heterozygous SNPs come from the high coverage LFR library and are not called in the standard library, indicating that MDA amplification and 160× coverage helps some regions get enough reads (five or more) to be called correctly. High-coverage LFR phasing rates can be adjusted to balance haplotype completeness versus phasing errors.

Haplotyping of a European Pedigree.

To further our understanding of the performance of LFR we made additional libraries from a pedigree of European ancestry. CEPH family 1463 was chosen because it has three generations of individuals, allowing for comprehensive studies of inheritance. This family has been previously studied as part of a public data release (www.completegenomics.com/sequence-data/download-data/). Libraries were made from individuals in each generation. A total of over 1.6 Tb of sequence data were generated for NA12877, NA12885, NA12886, NA12891, and NA12892. In general, phasing was very high across all samples with approximately 92% of attempted SNPs phased into contigs (FIG. 20). Combining two LFR libraries (FIG. 20) or LFR with parent-based phasing improved the overall rate of phased SNPs to 97%. The N50 contig length across all analysed family members was between 500-600 kb. This length is significantly lower than that of NA19240. An investigation of the distribution of SNPs across the genomes of several different ethnic groups explains this difference.

Origin and Impact of Regions of Low Heterozygosity in Non-African Populations.

There are approximately two-fold more regions of low heterozygosity (RLHs, defined as genomic regions of 30 kb with less than 1.4 heterozygous SNPs per 10 kb, approximately 7 times lower than the median density) of 30 kb-3 Mb in the European pedigree samples than in NA19240, clarifying a previously reported relative excess of homozygotes in non-Africans (Gibson et al., Hum. Mol. Genet. 15:789-795, 2006; Lohmueller et al., Nature 451:994-997, 2008) and further supported by an analysis of 52 complete genomes (Nicholas Schork, personal communication). These regions are barriers to phasing, resulting in a two-fold smaller N50 contig length. Over 90% of the contigs in European genomes end in these RLHs that vary between unrelated individuals.

Approximately 3% of all heterozygous SNPs in non-African genomes (30-60% of all non-phased heterozygous SNPs) belong to these RLHs which cover a very large fraction (30-40%) of these genomes. In Chinese and European genomes, long RLHs cluster around 45 heterozygous SNPs per Mb (the genomic average is approximately 1000 per Mb outside RLHs) indicating they shared a common ancestor around 37,000-43,000 years ago (based on a mutation rate of 60-70 SNPs per 20-year generation; Roach et al., Science 328:636-639, 2010; Conrad et al., Nat. Genet. 43:712-714, 2011). This is probably due to a strong bottleneck at the time of or after the human exodus out of Africa and within a previously determined range from 10,000-65,000 years ago (Li and Durbin, Nature 475:493-496, 2011). Furthermore, an excess of RLHs is observed on the X chromosome in European and Indian women (NA12885, NA12892, and NA20847) when compared to an African woman (NA19240) covering ~50% vs. 17% of this chromosome, respectively (30% vs. 14% for the entire genome in these same individuals). This indicates an even stronger out-of-Africa bottleneck for the X chromosome. A possible explanation is that substantially fewer females left Africa and had offspring with multiple males.

These observations suggest that whole genome variation analyses, including haplotyping, in thousands of diverse genomes will provide a deep understanding of human population genetics and the impact of these extensive "inbred" regions, frequently comprising >100 homozygote variants each, on human disease and other extreme phenotypes. In addition, it shows that about 2,000 RLHs>100 kb in length will be present in all non-African individuals. Populations with limited numbers of high-frequency haplotypes, as can result from recent bottlenecks or in-breeding (Gibson et al., Hum. Mol. Genet. 15:789-795, 2006), can also have long runs of identical heterozygous SNPs present in both parents, limiting use of parents for phasing or assigning shorter LFR contigs. Thus, population history and some reproduction patterns can make phasing challenging, as exhibited by the X chromosome of non-African woman. Regardless of these factors LFR phasing performance is approximately equivalent with up to 97% of heterozygous SNPs phased in both European and African individuals, a result that should translate across all populations. In addition to combining LFR with standard genotyping of one parent as described below (a strategy that will be more limited in some families, as discussed above), using initial DNA fragments longer than 300 kb, for example by entrapping cells or pre-purified DNA in gel blocks (Cook, EMBO J. 3:1837-1842, 1984), would span ~95% of all RLHs and haplotype most of the de novo mutations that occur in these regions. This would not be feasible with current fosmid cloning strategies (Kitzman et al., Nat. Biotechnol. 29:59-63, 2011; Suk et al., Genome Res. 21:1672-1685, 2011) which are limited to 40 kb fragments.

LFR Reproducibility and Phasing Error Rate Analysis.

In an effort to understand the reproducibility of LFR, we compared haplotype data between the two NA19240 replicate libraries. In general, the libraries were very concordant, with only 64 differences per library in ~2.2 million heterozygous SNPs phased by both libraries (FIG. 22). This represents a phasing error rate of 0.003% or 1 error in 44 Mb. LFR was also highly accurate when compared to the conservative but accurate whole chromosome phasing generated from the parental genomes NA19238 and NA19239 previously sequenced by multiple methods. Only ~60 instances in 1.57 million comparable individual loci were found in which LFR phased a variant inconsistent with that of the parental haplotyping (false phasing rate of 0.002% if half of discordances are due to sequencing errors in parental genomes). The LFR data also contained ~135 contigs per library (2.2%) with one or more flipped haplotype blocks (FIG. 22). Extending these analyses to the European replicate libraries of sample NA12877 (FIG. 22) and comparing them with a recent high quality family-based analysis using four children of NA12877 and their mother NA12878 (Roach et al., Am. J. Hum. Genet. 89:382-397, 2011) yielded similar results, assuming each method contributes half of the observed discordance. In both NA19240 and NA12877 libraries several contigs had dozens of flipped segments. The majority of these contigs tend to be located in regions of low heterozygosity (RLHs), low read coverage regions, or repetitive regions observed in an unexpectedly large number of wells (e.g., subtelomeric or centromeric regions).

Assigning Haplotype Contigs to Parental Chromosomes.

Most flipping errors can be corrected by forcing the LFR phasing algorithms to end contigs in these regions. Alternatively, these errors can be removed with the simple, low cost addition of standard high density array genotype data (~1 million or greater SNPs) from at least one parent to the LFR assembly. Additionally, we found that parental genotypes can connect 98% of LFR-phased heterozygous SNPs across full chromosomes. Additionally, this data allows haplotypes to be assigned to maternal and paternal lineages, information that is useful for incorporating parental imprinting in genetic diagnoses. If parental data is unavailable, population genotype data can also be used to connect LFR contigs across full chromosomes, although this approach may increase phasing errors (Browning and Browning, Nat. Rev. Genet. 12:703-714, 2011). Even technically challenging approaches such as metaphase chromosome separation, which have demonstrated full chromosome haplotyping, are unable to assign parental origin without some form of parental genotype data (Fan et al., Nat. Biotechnol. 29:51-57, 2011). This combination of two simple technologies, LFR and parental genotyping, provides accurate, complete, and annotated haplotypes at a low cost.

Phasing De Novo Mutations.

As a demonstration of the completeness and accuracy of our diploid genome sequencing we assessed phasing of 35 de novo mutations recently reported in the genome of NA19240 (Conrad et al., Nat. Genet. 43:712-714, 2011). Thirty-four of these mutations were called in either the standard genome or one of the LFR libraries. Of those, 32 de novo mutations were phased (16 coming from each parent) in at least one of the two replicate LFR libraries. Not surprisingly, the two non-phased variants reside in RLHs. Of these 32 variants, 21 were phased by Conrad et al. (ibid.) and 18 were consistent with LFR phasing results. The three discordances are likely due to errors in the previous study (Matthew Hurles personal communication), confirming LFR accuracy but not affecting the substantive conclusions of the report.

Genome Sequencing and Haplotyping from 100 pg of DNA Using Only LFR Libraries.

The analyses described above incorporated heterozygous SNPs from both a standard and an LFR library. However, it is possible to use only an LFR library, given that full representation of the genome is expected as a result of starting with an amount of DNA equivalent to that found in 10-20 cells. We have demonstrated that MDA provides sufficiently uniform amplification, and with high (80×) overall read coverage an LFR library taken alone allows for detection of up to 93% of heterozygous SNPs without any modifications to our standard library variation-calling algorithms. To demonstrate the potential of using only a LFR library, we phased NA19240 Replicate 1 as well as an additional 250 Gb of reads from the same library (500 Gb total). We observed 15% and 5% reductions, respectively, in the total number of SNPs phased (FIG. 20). This result is not surprising, given that this library was made from 60 pg of DNA instead of the optimal amount of 200 pg (Table 1 below) and also given the previously mentioned GC bias incorporated during in vitro amplification by MDA. Another 285 Gb LFR library called and phased alone 90% of all variants from standard and LFR libraries combined (FIG. 20). Despite the reduction in total SNPs phased, the contig length was largely unaffected (N50>1 Mb).

Error Reduction Enabled by LFR for Accurate Genome Sequencing from 10 Cells.

Substantial error rates (~1 SNV in 100-1,000 called kilobases) are a common attribute of all current massively parallelized sequencing technologies. These rates are probably too high for diagnostic use, and they complicate many studies searching for novel mutations. The vast majority of false positive variations are no more likely to occur on the maternal or paternal chromosome. This lack of consistent connectivity to the surrounding true variations can be exploited by LFR to eliminate these errors from the final assembled haplotypes. Both the Yoruban trio and the European pedigree provide an excellent platform for demonstrating the error reducing power of LFR. We defined a set of heterozygous SNPs in NA19240 and NA12877 (>85% of all heterozygous SNPs) that were reported with high confidence in each of the individual's parents as matching the human reference genome at both alleles. There were about 44,000 heterozygous SNPs in NA19240 and 30,000 in NA12877 that met this criterion. By virtue of their nonexistence in the parental genomes, these variations are de novo mutations, cell-line-specific somatic mutations, or false positive variants. Approximately 1,000-1,500 of these variants were reproducibly phased in each of the two replicate libraries from samples NA19240 and NA12877 (FIG. 23). These numbers are similar to those previously reported for de novo and cell line specific mutations in NA19240 (Conrad et al., Nat. Genet. 43:712-714, 2011). The remaining variants are likely to be initial false positives of which only about 500 are phased per library. This represents a 60-fold reduction of the false positive rate in those variations that are phased. Only ~2,400 of these false variants are present in the standard libraries, of which only ~260 are phased (<1 false positive SNV in 20 Mb; 5700 haploid Mb/260 errors). Each LFR library exhibits a 15-fold increase, compared to a genome sequenced by the standard process, in library-specific false positive calls before phasing. The majority of these false positive SNVs are likely to have been introduced by MDA; sampling of rare cell-line variants may be responsible for a smaller percentage. Despite making LFR libraries from 100 pg of DNA and introducing a large number of errors through MDA amplification, applying the LFR phasing algorithm reduces the overall sequencing error rate to 99.99999% (~600 false heterozygous SNVs/6 Gb), approximately 10-fold lower than error rates observed using the same ligation-based sequencing chemistry (Roach et al., Am. J. Human Genet. 89:382-397, 2011).

Improving Base Calling with LFR Information.

Figure 24:
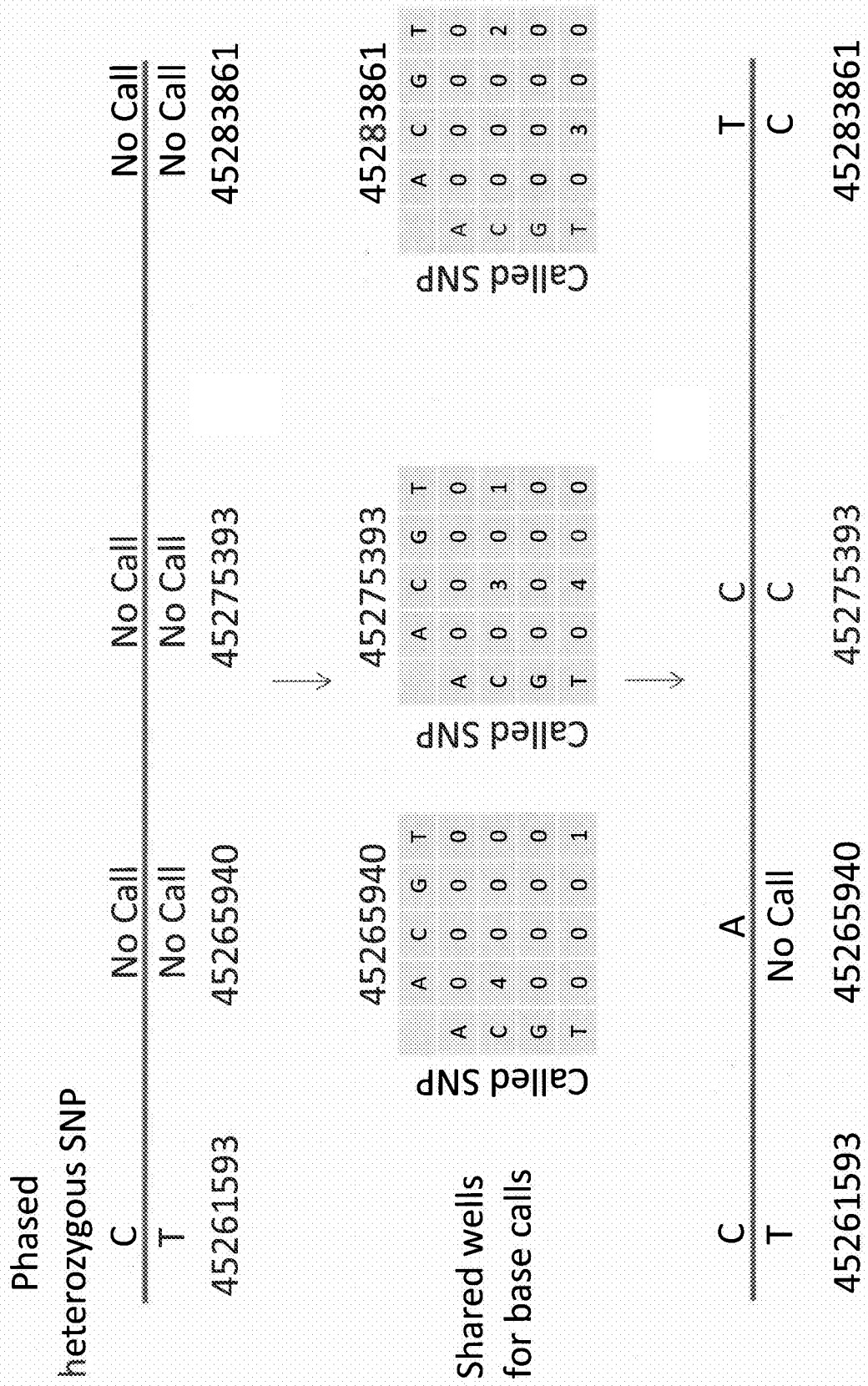
FIG. 24 shows LFR re-calling of no call positions. To demonstrate the potential of LFR to rescue no call positions three example positions were selected on chromosome18 that were uncalled (non-called) by standard software. By phasing them with a C/T heterozygous SNP that is part of an LFR contig, these positions can be partially or fully called. The distribution of shared wells (wells having at least one read for each of two bases in a pair; there are 16 pairs of bases for an assessed pair of loci) allows for the recalling of three N/N positions to A/N, C/C and T/C calls and defines C-A-C-T and T-N-C-C as haplotypes. Using well information allows LFR to accurately call an allele with as few as 2-3 reads if found in 2-3 expected wells, about three-fold less than without having well information.

In addition to phasing and eliminating false-positive heterozygous SNVs, LFR can "rescue" "no-call" positions or verify other calls (e.g., homozygous reference or homozygous variant) by assessing the well origin of the reads that support each base call. As a demonstration we found positions in the genome of NA19240 replicate one that were not called but were adjacent to a neighbouring phased heterozygous SNP. In these examples the position was able to be "recalled" as a phased heterozygous SNP do to the presence of shared wells between the neighbouring phased SNP and the no-call position (FIG. 24). While LFR may not be able to rescue all no-call positions, this simple demonstration highlights the usefulness of LFR in more accurate calling of all genomic positions to reduce no-calls.

Highly Divergent Haplotypes Present in African and Non-African Genomes.

Haplotype analyses, enabled by large scale genotyping studies such as the HapMap project, have been immensely important to understanding population genetics. However, the resolution of the complete haplotypes of individuals has largely been intractable or prohibitively expensive. Highly accurate haplotypes, filtered of clustered false heterozygotes accumulated due to false mapping of repeated regions (Li and Durbin, Nature 475:493-496, 2011; Roach et al., Science 328:636-639, 2010), will help understand many of the population phenomena found within individual genomes. As a demonstration, we scanned the LFR contigs of NA19240 for regions of high divergence between the maternal and paternal copies. Seven thousand 10-kb regions containing >33 SNVs were identified; a three-fold increase over the expected 10 SNVs. Assuming 0.1% standing variation and 0.15% base difference per 1 Myr (based on the 1% divergence of human and chimpanzee genomes evolving from a common ancestor ~6 Myr) our calculations suggest that ~50 Mb of these regions found in this African genome (~2.0% of "non-inbred" genome) may have been evolving separately for over 1.5 million years. This estimate is closer to 1 Myr if the chimpanzee-human separation was less than 5 Myr ago (Hobolth et al., Genome Res. 21:349-356, 2011). This whole genome analysis is in agreement with a recent study by Hammer et al. (Proc. Natl. Acad. Sci. U.S.A. 108:15123-15128, 2011) on a few targeted genomic regions in African populations postulating a possible interbreeding of separate Homo species in Africa. Our analysis shows that 2.1% of European non-inbred genomes also have similarly diverged sequences, mostly at distinct genomic positions. The majority of these were likely introduced prior to the exodus of humans from Africa.

Individual Genomes Contain Many Genes with Inactivating Variations in Both Alleles.

Highly accurate diploid genomes are a necessity for human genome sequencing to be valuable in a clinical setting. To demonstrate how LFR could be used in a diagnostic/prognostic environment we analysed the coding SNP data of NA19240 for nonsense and splicesite disrupting variations. We further analysed all of the missense variations using PolyPhen2 (Adzhubei et al., Nat. Methods 7:248-249, 2010) to select only those variations which coded for detrimental changes. Both "possibly damaging" and "probably damaging" were considered to be detrimental to protein function as were all nonsense mutations. 3485 variants matched these criteria. After phasing and removing false positives, only 1252 variants remained; an important reduction in potentially misleading information. We further reduced the list to examine only those 316 heterozygous variants wherein at least two co-occur in the same gene. Using phasing data we were able to identify 189 variants occurring in the same allele within 79 genes. The remaining 127 SNPs were found to be dispersed across 47 genes with a least one detrimental variation in each allele (FIG. 25). Haplotying NA19240 by combining two LFR libraries increases this number to 65 genes. Extending this analysis to the European pedigree demonstrated that a similar number of genes (32-49 with coding mutations in both alleles) were potentially altered to the point where little to no effective protein product is expressed (FIG. 25). Extending this analysis to variants which disrupt transcription factor binding sites (TFBS) introduces an additional ~100 genes per individual. Many of these are likely to be partial loss or no loss of function changes. Due to the high accuracy of LFR, it is unlikely that these variants are a result of sequencing errors. Many of the discovered detrimental mutations could have been introduced in the propagation of these cell lines. A few of these genes were found in unrelated individuals, suggesting that they could be improperly annotated or the result of a systematic mapping or reference error. The genome of NA19240 contained an additional ~10 genes in the complete loss of function category; this is most likely due to biases introduced by using a European reference genome to annotate an African genome. Nonetheless, these numbers are similar to those found in several recent studies on phased individual genomes (Suk et al., Genome Res. 21:1672-1685, 2011; Lohmueller et al., Nature 451:994-997, 2008) and suggest that most generally healthy individuals probably have a small number of genes, not absolutely required for normal life, which encode ineffective protein products. We have demonstrated that LFR is able to place SNPs into haplotypes over large genomic distances where the phase of those SNPs could cause a potential complete loss of function to occur. This type of information will be critical for effective clinical interpretation of patient genomes and for carrier screening.

TFBS Disruption Linked to Differences in Allelic Expression.

Long haplotypes that encompass both cis-regulatory regions and coding sequences are critical for understanding and predicting expression levels of each allele of a gene. By analysing 5.6 Gbs of non-exhaustive expression data from RNA sequencing of lymphocytes from NA20431 we identified a small number of genes that have significant differences in allele expression. In each of these genes 5 kb of the regulatory region upstream of the transcription start site and 1 kb downstream were scanned for SNVs that significantly alter the binding sites of over 300 different transcription factors (Sandelin et al., 32:D91-D94, 2004). In six examples (FIG. 26), 1-3 bases between the two alleles were found to differ in each gene causing a significant impact to one or more putative binding sites and potentially explaining the observed differential expression between alleles. While this is just one data set and it is not currently clear how large an impact these changes have on transcription factor binding, these results demonstrate that with large scale studies of this type (Rozowsky et al., Mol. Syst. Biol. 7:522, 2011), that become feasible using LFR haplotyping, the consequences of sequence changes to transcription factor binding sites may be elucidated.

Discussion

We have demonstrated the power of LFR to accurately phase up to 97% of all detected heterozygous SNPs in a genome into long contiguous stretches of DNA (N50s 400-1500 kb in length). Even LFR libraries, phased without candidate heterozygous SNPs from standard libraries and thus using only 10-20 human cells, are able to phase 85-94% of the available SNPs in spite of limitations in the current implementation. In several instances, the LFR libraries used in this paper had less than optimal starting input DNA (e.g., NA20431). Phasing-rate improvements seen by combining two replicate libraries (samples NA19240 and NA12877) or starting with more DNA (NA12892) agree with this conclusion. Additionally, underrepresentation of GC-rich sequences resulted in less of the genome being called (90-93% versus >96% for standard libraries). Improvements to the MDA process (e.g., by adding region-specific primers or using less amplification by improving the yield in other steps) or in how we perform base and variant calling in LFR libraries, possibly by using assignments of reads to wells, will help increase the coverage in these regions. Moreover, as the cost of whole genome sequencing continues to fall, higher coverage libraries, which dramatically improve call rates and phasing, will become more affordable.

A consensus haploid sequence is sufficient for many applications; however it lacks two very important pieces of data for personalized genomics: phased heterozygous variants and identification of false positive and negative variant calls. One of the goals of personal genomics is to detect disease causing variants and to be extremely confident in determining whether an individual carries such a variant or has one or two unaffected alleles. By providing sequence data from both the maternal and paternal chromosomes independently, LFR is able to detect regions in the genome assembly where only one allele has been covered. Likewise, false positive calls are avoided because LFR independently, in separate aliquots, sequences both the maternal and paternal chromosomes 10-20 times. The result is a statistically low probability that random sequence errors would repeatedly occur in several aliquots at the same base position on one parental allele. Thus, LFR allows, for the first time, both accurate and cost-effective sequencing of a genome from a few (preferably 10-20) human cells despite using in vitro DNA amplification and the resulting large number of unavoidable polymerase errors. Further, by phasing SNPs over hundreds of kilobases to multiple megabases (or over entire chromosomes by integrating LFR with routine genotyping of one or both parents), LFR is able to more accurately predict the effects of compound regulatory variants and parental imprinting on allele specific gene expression and function in various tissue types. Taken together this provides a highly accurate report about the potential genomic changes that could cause gain or loss of protein function. This kind of information, obtained inexpensively for every patient, will be critical for clinical use of genomic data. Moreover, successful and affordable diploid sequencing of a human genome starting from ten cells opens the possibility for comprehensive and accurate genetic screening of microbiopsies from diverse tissues sources such as circulating tumor cells or pre-implantation embryos generated through in vitro fertilization.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

TABLE 1

| Sample | PGD embryo samples | | | | | Normal Library |
| --- | --- | --- | --- | --- | --- | --- |
| | 2A | 5B | 5C | 7C | 10C | NA20502 |
| Myotonic Dystrophy Diagnosis | Unaffected | Affected | Affected | No diagnosis | No diagnosis | Unaffected |
| Total GB mapped | 155.3 | 164.04 | 154.67 | 162.76 | 187.85 | 143.91 |
| Gender | Female | Male | Male | Male | Male | Female |
| Fully called genome fraction | 0.85 | 0.91 | 0.90 | 0.94 | 0.95 | 0.97 |
| Partially called genome fraction | 0.03 | 0.02 | 0.02 | 0.01 | 0.01 | 0.00 |
| Fully called coding sequence fraction | 0.89 | 0.89 | 0.90 | 0.92 | 0.90 | 0.96 |
| SNP total count | 2,616,243 | 2,917,414 | 2,874,253 | 3,141,507 | 3,124,345 | 3,379,388 |
| Chimera data | | | | | | |
| Pct with mates on different contigs or more than 50 kb apart | 2.17% | 2.20% | 2.79% | 2.85% | 2.43% | 0.95% |

TABLE 1-continued

|  | PGD embryo samples | | | | | Normal Library |
| --- | --- | --- | --- | --- | --- | --- |
| Sample | 2A | 5B | 5C | 7C | 10C | NA20502 |
| Pct with mates within 50 kb on different strands | 1.77% | 2.03% | 2.12% | 1.56% | 1.73% | 0.00% |
| Pct with mates paired | 95.93% | 95.62% | 94.92% | 95.47% | 95.71% | 99.04% |
| Amplification prior to library preparation | 16,500 | 15,700 | 19,500 | 18,000 | 14,000 | 0 |

What is claimed is:

1. A method of analyzing genomic DNA of an organism to produce a phased sequence corresponding to at least a portion of a genome of the organism, the method comprising:

providing a plurality of aliquots of the genomic DNA of the organism;

tagging fragments of genomic DNA in each aliquot with a corresponding aliquot-specific tag sequence;

sequencing the tagged fragments of genomic DNA to obtain a plurality of reads;

receiving, at one or more computing devices, the plurality of reads corresponding to fragments of genomic DNA from the plurality of aliquots, each read comprising a sequence from a fragment of genomic DNA and an aliquot-specific tag sequence, wherein each aliquot contains less than a haploid genome equivalent of genomic DNA;

determining, with the one or more computing devices, the aliquots from which the plurality of reads originate by identifying the aliquot-specific tag sequences;

producing, with the one or more computing devices, the phased sequence from the reads by:

identifying a plurality of heterozygous loci corresponding to at least a portion of the genome of the organism based on numbers of reads having different alleles at each of the plurality of heterozygous loci; and phasing the plurality of heterozygous loci to produce a first haplotype and a second haplotype, the phasing using the aliquots of origin for reads mapping to the plurality of heterozygous loci to determine which alleles at the heterozygous loci are on a same haplotype, wherein reads at different ones of the plurality of heterozygous loci and having the same aliquot of origin are determined to be from the same haplotype, the phased sequence corresponding to the first haplotype and the second haplotype of the at least a portion of the genome of the organism.

2. The method of claim 1, further comprising:
identifying a first sequence variant at a first locus based on reads having a first allele and a second allele at the first locus;
determining which reads correspond to which of the first and second haplotypes based on the aliquots of origin; and
identifying as an error the first sequence variant at the first locus when the aliquots of origin for the reads of the first and second allele are inconsistent with an existence of both the first and second alleles at the first locus.

3. The method of claim 1, wherein at least 70 percent of the heterozygous loci are phased.

4. The method of claim 1, wherein a region of the at least a portion of the genome of the organism comprises a short tandem repeat, the method further comprising:
determining a first number of reads of the first haplotype in the region;
determining a second number of reads of the second haplotype in the region;
comparing the first number with the second number; and
based on the comparison, identifying an expansion of the short tandem repeat in the first haplotype or the second haplotype.

5. The method of claim 1, further comprising:
producing, with the one or more computing devices, a plurality of assembled sequences that align to an overlap region of the genome, each assembled sequence in the overlap region corresponding to a different aliquot, wherein the plurality of heterozygous loci include N heterozygous loci, where N is an integer greater than one;
wherein phasing the plurality of heterozygous loci includes:
clustering the assembled sequences in a space of 2N to 4N possibilities based on the alleles at the N heterozygous loci for the respective assembled sequences, thereby creating a plurality of clusters; and
identifying two clusters with a highest density.

6. The method of claim 5, wherein the phasing further includes:
computing a matrix of N dimensions, each dimension corresponding to a heterozygous locus, where each matrix element corresponds to a number of assembled sequences having a combination of alleles corresponding to the matrix element;
identifying a first matrix element and a second matrix element that are each a center of one of the two clusters;
determining the first haplotype at the N heterozygous loci from the first matrix element; and determining the second haplotype at the N heterozygous loci from the second matrix element.

7. The method of claim 1, wherein the organism is a diploid mammal, the method further comprising:
producing an assembled sequence for the first and second haplotypes using the phased sequence, wherein the assembled sequences comprise a genome call rate of 70% or greater and an exome call rate of 70% or greater.

8. The method of claim 7, wherein the assembled sequence comprises less than one false single nucleotide variant per megabase.

9. The method of claim 7, wherein the assembled sequence comprises less than 600 false single nucleotide variants per gigabase.

10. The method of claim 7, further comprising:
calling a base at a position of the assembled sequence based on preliminary base calls for the position from two or more aliquots; and
identifying the base call as true when the base call is present three or more times in reads from the two or more aliquots.

11. The method of claim 1, wherein phasing the plurality of heterozygous loci includes:
for each of a plurality of pairs of heterozygous loci:
determining a matrix of a number of shared aliquots between alleles at the heterozygous loci of the pair, the heterozygous loci of the pair being located within a specified distance of each other.

12. The method of claim 11, wherein phasing the plurality of heterozygous loci further includes:
using each matrix to calculate a score and an orientation for the respective pair of heterozygous loci; and
using the scores and the orientations to determine the first haplotype and the second haplotype.

13. The method of claim 12, wherein using the scores and the orientations to determine the first haplotype and the second haplotype includes:
optimizing a graph of connections between pairs of heterozygous loci based on the scores and the orientations.

14. The method of claim 1, further comprising:
identifying a phased SNP from the plurality of heterozygous loci, the phased SNP having a first allele and a second allele;
identifying a locus that is a neighbor of the phased SNP, where the locus as a no-call, the locus having reads with a third allele and a fourth allele;
calculating a first number of shared aliquots that include the first allele at the phased SNP and the third allele at the locus; and
determining the third allele to be at the locus based on the first number of shared aliquots.

15. The method of claim 14, further comprising:
determining the third allele is at the locus when the first number of shared aliquots is above a threshold, the threshold being two or more.

16. The method of claim 14, further comprising:
calculating a second number of the shared aliquots that include the second allele at the phased SNP and the third allele at the locus;
calculating a third number of the shared aliquots that include the first allele at the phased SNP and the fourth allele at the locus;
determining the locus to be homozygous for the third allele when the first number and the second number are greater than a threshold, and the third number is less than the threshold.

17. The method of claim 14, further comprising:
  calculating a second number of the shared aliquots that include the second allele at the phased SNP and the fourth allele at the locus; and
  determining the locus to be heterozygous for the third allele and the fourth allele when all of the reads with the third allele share an aliquot with the first allele, and all of the reads with the fourth allele share an aliquot with the second allele.

18. The method of claim 1, further comprising:
  phasing at least 70 percent of the plurality of heterozygous loci.

19. The method of claim 1, wherein each aliquot-specific tag comprises an error-correction code, and wherein each read comprises correct tag sequence data or incorrect tag sequence data that comprises one or more errors, the method further comprising:
  using the error-correction code to correct the incorrect tag sequence data, thereby producing corrected tag sequence data and tag sequence data that cannot be corrected;
  using reads comprising the correct tag sequence data and the corrected tag sequence data in a first computer process that requires the tag sequence data and that produces a first output; and
  using reads comprising the tag sequence data that cannot be corrected in a second computer process that does not require the tag sequence data and that produces a second output.

20. The method of claim 19, wherein said first computer process is selected from a list comprising sample multiplexing, library multiplexing, phasing, and an error correction process that employs the tag sequence data, and wherein the second computer process comprises mapping, assembly, and pool-based statistics.

21. The method of claim 1, wherein the phased sequence is of a first region of the genome of the organism, the first region comprising a short tandem repeat, the method further comprising:
  comparing reads of the first haplotype of the region with reads of the second haplotype; and
  based on the comparison, identifying an expansion of the short tandem repeat in one of the first haplotype or the second haplotype.

22. The method of claim 1, wherein the genomic DNA is from a group consisting of the genome of the organism, an exome of the organism, a mixture of genomes of different organisms that includes the organism, a mixture of genomes of different cell types of the organism, and subsets thereof.

23. The method of claim 1, further comprising:
  amplifying the fragments of genomic DNA in each aliquot.

24. The method of claim 1, wherein the organism is a mammal.

25. The method of claim 1, wherein the organism is a human.

26. A computer-readable non-transitory storage medium storing instructions which, when executed by one or more computing devices, cause the one or more computing devices to analyzing genomic DNA of an organism to produce a phased sequence corresponding to at least a portion of a genome of the organism, the instructions comprising:
  receiving a plurality of reads corresponding to fragments of genomic DNA from a plurality of aliquots, each fragment of genomic DNA being tagged with an aliquot-specific tag sequence, and each read comprising sequence from a fragment of genomic DNA and an aliquot-specific tag sequence, wherein each aliquot contains less than a haploid genome equivalent of genomic DNA, wherein the plurality of reads are obtained by:
    providing the plurality of aliquots of the genomic DNA of the organism;
    tagging the fragments of genomic DNA in each aliquot with the corresponding aliquot-specific tag sequence; and
    sequencing the tagged fragments of genomic DNA to obtain a plurality of reads;
  determining the aliquots from which the plurality of reads originate by identifying the aliquot-specific tag sequences;
  producing the phased sequence from the reads by:
    identifying a plurality of heterozygous loci corresponding to at least a portion of the genome of the organism based on numbers of reads having different alleles at each of the plurality of heterozygous loci; and
    phasing the plurality of heterozygous loci to produce a first haplotype and a second haplotype, the phasing using the aliquots of origin for reads mapping to the plurality of heterozygous loci to determine which alleles at the heterozygous loci are on a same haplotype, wherein reads at different ones of the plurality of heterozygous loci and having the same aliquot of origin are determined to be from the same haplotype, the phased sequence corresponding to the first haplotype and the second haplotype of the at least a portion of the genome of the organism.

27. The computer-readable non-transitory storage medium of claim 25, wherein the instructions further comprise:
  identifying a first sequence variant at a first locus based on reads having a first allele and a second allele at the first locus;
  determining which reads correspond to which of the first and second haplotypes based on the aliquots of origin; and
  identifying as an error the first sequence variant at the first locus when the aliquots of origin for the reads of the first and second allele are inconsistent with an existence of both the first and second alleles at the first locus.

28. The computer-readable non-transitory storage medium of claim 25, wherein a region of the at least a portion of the genome of the organism comprises a short tandem repeat, wherein the instructions further comprise:
  determining a first number of reads of the first haplotype in the region;
  determining a second number of reads of the second haplotype in the region;
  comparing the first number with the second number; and
  based on the comparison, identifying an expansion of the short tandem repeat in the first haplotype or the second haplotype.

29. The computer-readable non-transitory storage medium of claim 25, wherein the instructions further comprise:
  producing a plurality of assembled sequences that align to an overlap region of the genome, each assembled sequence in the overlap region corresponding to a different aliquot, wherein the plurality of heterozygous loci include N heterozygous loci, where N is an integer greater than one;

wherein phasing the plurality of heterozygous loci includes:
  clustering the assembled sequences in a space of 2N to 4N possibilities based on the alleles at the N heterozygous loci for the respective assembled sequences, thereby creating a plurality of clusters; and
  identifying two clusters with a highest density.

30. The computer-readable non-transitory storage medium of claim 29, wherein the phasing further includes:
  computing a matrix of N dimensions, each dimension corresponding to a heterozygous locus, where each matrix element corresponds to a number of assembled sequences having a combination of alleles corresponding to the matrix element;
  identifying a first matrix element and a second matrix element that are each a center of one of the two clusters;
  determining the first haplotype at the N heterozygous loci from the first matrix element; and
  determining the second haplotype at the N heterozygous loci from the second matrix element.

31. The computer-readable non-transitory storage medium of claim 25, wherein the instructions further comprise:
  producing an assembled sequence for the first and second haplotypes using the phased sequence;
  calling a base at a position of the assembled sequence based on preliminary base calls for the position from two or more aliquots; and
  identifying the base call as true when the base call is present three or more times in reads from the two or more aliquots.

32. The computer-readable non-transitory storage medium of claim 25, wherein phasing the plurality of heterozygous loci includes:
  for each of a plurality of pairs of heterozygous loci:
  determining a matrix of a number of shared aliquots between alleles at the heterozygous loci of the pair, the heterozygous loci of the pair being located within a specified distance of each other.

33. The computer-readable non-transitory storage medium of claim 32, wherein phasing the plurality of heterozygous loci further includes:
  using each matrix to calculate a score and an orientation for the respective pair of heterozygous loci; and
  using the scores and the orientations to determine the first haplotype and the second haplotype.

34. The computer-readable non-transitory storage medium of claim 33, wherein using the scores and the orientations to determine the first haplotype and the second haplotype includes:
  optimizing a graph of connections between pairs of heterozygous loci based on the scores and the orientations.

35. The computer-readable non-transitory storage medium of claim 26, wherein the instructions further comprise:
  identifying a phased SNP from the plurality of heterozygous loci, the phased SNP having a first allele and a second allele;
  identifying a locus that is a neighbor of the phased SNP, where the locus as a no-call, the locus having reads with a third allele and a fourth allele;
  calculating a first number of shared aliquots that include the first allele at the phased SNP and the third allele at the locus; and
  determining the third allele to be at the locus based on the first number of shared aliquots.

36. The computer-readable non-transitory storage medium of claim 35, wherein the instructions further comprise:
  determining the third allele is at the locus when the first number of shared aliquots is above a threshold, the threshold being two or more.

37. The computer-readable non-transitory storage medium of claim 35, wherein the instructions further comprise:
  calculating a second number of the shared aliquots that include the second allele at the phased SNP and the third allele at the locus;
  calculating a third number of the shared aliquots that include the first allele at the phased SNP and the fourth allele at the locus;
  determining the locus to be homozygous for the third allele when the first number and the second number are greater than a threshold, and the third number is less than the threshold.

38. The computer-readable non-transitory storage medium of claim 35, wherein the instructions further comprise:
  calculating a second number of the shared aliquots that include the second allele at the phased SNP and the fourth allele at the locus; and
  determining the locus to be heterozygous for the third allele and the fourth allele when all of the reads with the third allele share an aliquot with the first allele, and all of the reads with the fourth allele share an aliquot with the second allele.

39. The computer-readable non-transitory storage medium of claim 26, wherein the phased sequence is of a first region of the genome of the organism, the first region comprising a short tandem repeat, wherein the instructions further comprise:
  comparing reads of the first haplotype of the region with reads of the second haplotype; and
  based on the comparison, identifying an expansion of the short tandem repeat in one of the first haplotype or the second haplotype.

* * * * *

UNITED STATES PATENT AND TRADEMARK OFFICE
CERTIFICATE OF CORRECTION

| | | |
|---|---|---|
| PATENT NO. | : 9,524,369 B2 | Page 1 of 1 |
| APPLICATION NO. | : 13/447087 | |
| DATED | : December 20, 2016 | |
| INVENTOR(S) | : Radoje Drmanac et al. | |

It is certified that error appears in the above-identified patent and that said Letters Patent is hereby corrected as shown below:

In the Claims

Column 74, Claim 27, Line 35: Delete "of claim 25;" and insert --of claim 26,--

Column 74, Claim 28, Line 48: Delete "of claim 25," and insert --of claim 26,--

Column 74, Claim 29, Line 60: Delete "of claim 25," and insert --of claim 26,--

Column 75, Claim 31, Line 24: Delete "of claim 25," and insert --of claim 26,--

Column 75, Claim 32, Line 35: Delete "of claim 25," and insert --of claim 26,--

Signed and Sealed this
Thirtieth Day of May, 2017

Michelle K. Lee
*Director of the United States Patent and Trademark Office*

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: synthetic parental label Mom haplotype contig
      in parent-assisted universal phasing

<400> SEQUENCE: 1
ccgcagtagc ttacgaatcg                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic parental label Dad haplotype contig
      in parent-assisted universal phasing

<400> SEQUENCE: 2
gatttaactg agcacttggc                                              20

<210> SEQ ID NO 3
<211> LENGTH: 10
<212> TYPE: DNA
<213> ORGANISM: Artificial Sequence
<220> FEATURE:
<223> OTHER INFORMATION: synthetic Aliquot Tag 1

<400> SEQUENCE: 3
aacgagtatt                                                         10

<210> SEQ ID NO 4
<211> LENGTH: 10
<212> TYPE: DNA
<213> ORGANISM: Artificial Sequence
<220> FEATURE:
<223> OTHER INFORMATION: synthetic Aliquot Tag 2

<400> SEQUENCE: 4
tttggcgttc                                                         10

<210> SEQ ID NO 5
<211> LENGTH: 10
<212> TYPE: DNA
<213> ORGANISM: Artificial Sequence
<220> FEATURE:
<223> OTHER INFORMATION: synthetic Aliquot Tag 3

```
<400> SEQUENCE: 5
gtagtaccgg                                                              10

<210> SEQ ID NO 6
<211> LENGTH: 10
<212> TYPE: DNA
<213> ORGANISM: Artificial Sequence
<220> FEATURE:
<223> OTHER INFORMATION: synthetic Aliquot Tag M

<400> SEQUENCE: 6
aactgagcgg                                                              10

<210> SEQ ID NO 7
<211> LENGTH: 12
<212> TYPE: DNA
<213> ORGANISM: Artificial Sequence
<220> FEATURE:
<223> OTHER INFORMATION: synthetic aliquot-tagged Read 1

<400> SEQUENCE: 7
cagtcaagtg at                                                           12

<210> SEQ ID NO 8
<211> LENGTH: 12
<212> TYPE: DNA
<213> ORGANISM: Artificial Sequence
<220> FEATURE:
<223> OTHER INFORMATION: synthetic aliquot-tagged Read 2

<400> SEQUENCE: 8
catgatgagg ac                                                           12

<210> SEQ ID NO 9
<211> LENGTH: 12
<212> TYPE: DNA
<213> ORGANISM: Artificial Sequence
<220> FEATURE:
<223> OTHER INFORMATION: synthetic aliquot-tagged Read 3

<400> SEQUENCE: 9
tcttagcatg ta                                                           12

<210> SEQ ID NO 10
<211> LENGTH: 12
<212> TYPE: DNA
<213> ORGANISM: Artificial Sequence
<220> FEATURE:
<223> OTHER INFORMATION: synthetic aliquot-tagged Read M

<400> SEQUENCE: 10
gtaactattc ag                                                           12
```